United States Patent [19]

Krumkalns et al.

[11] Patent Number: 4,874,775

[45] Date of Patent: Oct. 17, 1989

[54] AGRICULTURALLY USEFUL SULFONAMIDES

[75] Inventors: Eriks V. Krumkalns, Indianapolis; David L. Smiley, Greenfield, both of Ind.

[73] Assignee: Eli Lilly and Company, Indianapolis, Ind.

[21] Appl. No.: 743,234

[22] Filed: Jun. 11, 1985

[51] Int. Cl.[4] .................. A61K 31/44; C07D 213/42
[52] U.S. Cl. .................................. 514/357; 514/256; 514/352; 514/358; 544/322; 544/335; 546/312; 546/330; 546/338
[58] Field of Search ................. 546/312, 330, 338; 544/332, 335, 322; 514/256, 352, 357, 358; 71/92, 94

[56] References Cited

U.S. PATENT DOCUMENTS

| | | | |
|---|---|---|---|
| 3,438,980 | 4/1969 | Zimmerman | 544/297 |
| 3,459,742 | 8/1969 | Lehr | 544/319 |
| 3,567,715 | 3/1971 | Larsen | 544/297 |
| 3,766,193 | 10/1973 | Harrington et al. | 71/92 X |
| 3,980,781 | 9/1976 | Snell et al. | 514/272 |
| 3,995,044 | 11/1976 | Kabbe et al. | 514/357 |
| 4,219,558 | 8/1980 | Madsen | 514/352 |
| 4,415,565 | 11/1983 | Wysor | 514/184 |
| 4,457,930 | 7/1984 | Schmitt et al. | 514/238.2 |
| 4,501,746 | 2/1985 | Krumkalns | 514/357 |
| 4,543,413 | 9/1985 | Munro | 546/305 |

FOREIGN PATENT DOCUMENTS

| | | |
|---|---|---|
| 1576378 | 1/1969 | France . |
| 2240217 | 6/1973 | France . |
| 1574477 | 10/1980 | United Kingdom . |
| 2056974 | 3/1981 | United Kingdom . |

OTHER PUBLICATIONS

*Chemical Abstracts*, 64: 19552 e (1966).

*Primary Examiner*—Richard A. Schwartz
*Attorney, Agent, or Firm*—Donald R. Stuart; Leroy Whitaker; Joseph A. Jones

[57] ABSTRACT

A series of novel N-pyrinidyl- and pyrimidinyl sulfonamides are useful as fungicides and herbicides particularly for the protection of plants from phytopathogens.

35 Claims, No Drawings

AGRICULTURALLY USEFUL SULFONAMIDES

Background of the Invention

This invention belongs to the fields of organic and agricultural chemistry, and provides a series of new pyridinyl- and pyrimidinylsulfonamides which are useful as both fungicides and herbicides.

Summary of the Invention

The present invention provides a series of sulfonamides of the formula

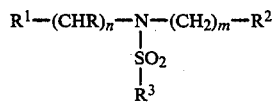

wherein
- n is 0 or 1;
- m is 0, 1 or 2;
- R is hydrogen; $C_1$-$C_4$ alkyl; phenyl; or phenyl monosubstituted with fluoro, chloro, bromo or iodo;
- $R^1$ is pyridinyl; pyridinyl oxide; or 5-pyrimidinyl;
- $R^2$ is $C_3$-$C_8$ cycloalkyl; $C_4$-$C_{10}$ alkyl; cyano; phenyl; phenyl mono- or disubstituted with fluoro, chloro, bromo, iodo, $C_1$-$C_3$ alkyl, $C_1$-$C_3$ (fluoro, chloro or bromo)alkyl, $C_1$-$C_3$ alkoxy, $C_1$-$C_3$ (fluoro, chloro or bromo)alkoxy, $C_1$-$C_3$ alkylthio, hydroxy, nitro, or cyano; or phenyl monosubstituted with $C_3$-$C_8$ cycloalkylmethoxy or phenoxy:
- $R^3$ is $C_1$-$C_6$ alkyl; $C_1$-$C_3$ alkylamino; di($C_1$-$C_3$ alkyl)amino; $C_1$-$C_3$ (fluoro, chloro or bromo)alkyl; phenyl; or phenyl mono- or disubstituted with fluoro, chloro, bromo, iodo, $C_1$-$C_3$ alkyl, or $C_1$-$C_3$ (fluoro, chloro or bromo)alkyl;

provided that $R^2$ is cyano only when m is 1 or 2; or an acid addition salt of compounds wherein $R^1$ is pyridinyl or 5-pyrimidinyl; provided that salts of compounds wherein $R^1$ is 5-pyrimidinyl are only hydrohalides.

The invention also provides a method of reducing the adverse effects of phytopathogens on plants which comprises applying a phytopathogen-inhibiting amount of a compound of the above formula to a plant to be protected from the disease or to the soil in which the plant grows.

The invention further provides agriculturally useful compositions comprising a compound of the above formula and an agriculturally-acceptable inert carrier.

Still further, the invention provides a method of reducing the vigor of weeds which comprises applying to a weed or to the soil in which it grows a compound of the above formula, provided that compounds for herbicidal use do not include those wherein $R^2$ is cyano, or phenyl substituted with $C_1$-$C_3$ (fluoro, chloro or bromo)alkyl, cyano, nitro, cycloalkylmethoxy or phenoxy.

Description of the Preferred Embodiments

Throughout this document, temperatures will be expressed in degrees Celsius. All expressions of concentration, percentage and the like will be in weight units unless otherwise stated.

The general chemical terms used in the present document have their usual meanings. For example, the term "haloalkyl" refers to alkyl groups substituted with any number of fluorine, chlorine or bromine atoms. The term "halophenyl" refers to phenyl rings substituted with fluorine, chlorine, bromine or iodine atoms, as described in the general formula above.

The term "hydrohalide" refers to hydrochloride, hydrobromide, hydrofluoride or hydroiodide.

The term "$C_1$-$C_4$ alkyl" includes, for example, methyl, ethyl, propyl, isopropyl, 1-methylpropyl and t-butyl. The term "$C_3$-$C_8$ cycloalkyl" includes, for example, cyclopropyl, cyclopentyl, cyclohexyl and cyclobutyl. The term "$C_4$-$C_{10}$ alkyl" includes, for example, butyl, 2-methylpropyl, pentyl, hexyl, 3-ethylhexyl, octyl, 1,1-diethylhexyl, nonyl, and decyl.

The term "$C_1$-$C_3$ alkyl" includes methyl, ethyl, propyl and isopropyl. The term "$C_1$-$C_3$ (fluoro, chloro or bromo)alkyl" includes those alkyl groups substituted with any number of the three halogen atoms. The term "$C_1$-$C_3$ alkoxy" includes any of the alkyl groups linked through an oxygen atom, and the term "$C_1$-$C_3$ (fluoro, chloro or bromo)alkoxy" includes those alkyl groups, substituted with any number of halogen atoms and linked through an oxygen. The term "$C_1$-$C_3$ alkylthio" includes those alkyl groups linked through a sulfur atom. The term "$C_1$-$C_3$ alkylamino" includes those alkyl groups linked through an amino nitrogen atom, and the term "di($C_1$-$C_3$ alkyl)amino includes two such alkyl groups, which may be the same or different, linked through a single amino nitrogen.

The term "$C_1$-$C_6$ alkyl" includes, for example, methyl, ethyl, propyl, 2-methylpropyl, pentyl, hexyl, and 3-methylpentyl.

Certain classes of the compounds of the present invention are preferred. Each of the following short descriptions sets out a preferred sub-class of compounds. It will be understood that the limitations which follow may be combined at will to produce further, more limited sub-classes of preferred compounds.

(a) n is 1;
(b) m is 0 or 1;
(c) m is 0;
(d) R is hydrogen or alkyl;
(e) R is hydrogen or methyl;
(f) R is hydrogen;
(g) $R^1$ is pyridinyl or pyridinyl oxide;
(h) $R^1$ is pyridinyl;
(i) $R^1$ is 3-pyridinyl or 3-pyridinyl oxide;
(j) $R^1$ is 5-pyrimidinyl;
(k) $R^2$ is substituted phenyl;
(l) $R^2$ is phenyl substituted with halo, alkyl, haloalkly or haloalkoxy;
(m) $R^2$ is phenyl substituted with halo;
(n) $R^2$ is phenyl substituted with fluoro or chloro;
(o) $R^2$ is phenyl substituted with fluoro or chloro and with alkyl;
(p) $R^2$ is alkyl, alkylamino, dialkylamino or substituted phenyl;
(q) $R^3$ is $C_1$-$C_4$ alkyl, methylamino, dimethylamino or substituted phenyl;
(r) $R^3$ is methyl, methylamino, dimethylamino, or phenyl substituted with halo, methyl or (fluoro, chloro or bromo)methyl;
(s) $R^3$ is methyl;
(t) $R^3$ is methylamino or dimethylamino;
(u) $R^3$ is phenyl substituted with fluoro, chloro, methyl or (fluoro, chloro or bromo)methyl.

While it is believed that the above general formula clearly explains the nature of the compounds of the present invention, a group of exemplary compounds will be named to insure comprehension.

N-(2-cyclopropylethyl)-N-(pyrimidin-5-ylmethyl)ethanesulfonamide

N-cyclopentyl-N-[1-(pyridin-3-yl)propyl]isopropanesulfonamide, oxide

N-cyclooctylmethyl-N-(pyridin-3-yl)-3-methylbutanesulfonamide

N-pentyl-N-[1-(pyridin-2-yl)-2-methylpropyl]hexanesulfonamide

N-hexyl-N-(pyridin-3-ylmethyl)-t-butanesulfonamide, hydrochloride

N-undecyl-N-(pyrimidin-5-ylmethyl)-2-ethylbutanesulfonamide

N-(1,1-dimethylbutyl)-N-[1-(pyrimidin-5-yl)ethyl]methanesulfonamide

N-(1,3-diethylpentyl)-N-(pyridin-4-ylmethyl)methanesulfonamide, oxide

N-cyanomethyl-N'-methyl-N-(pyridin-4-ylmethyl)sulfamide

N-(2,6-difluorophenyl)-N'-propyl-N-(pyridin-3-yl)sulfamide, lactate

N-(3,5-dichlorobenzyl)-N'-isopropyl-N-(pyrimidin-5-ylmethyl)sulfamide

N-(4-bromophenyl)-N',N'-diethyl-N-(pyridin-3-ylmethyl)sulfamide

N-(2,5-dibromophenyl)-N'-ethyl-N'-propyl-N-[1-(pyridin-3-yl)propyl]sulfamide, hydrochloride N-ethyl-N'-(3-iodophenyl)-N-methyl-N'-(pyridin-2-ylmethyl)sulfamide N-[2-(3-fluoro-5-iodophenyl)ethyl]-N-(pyrimidin-5-ylmethyl)-(1,1,2,2-tetrafluoroethane)sulfonamide, hydrobromide N-(2-methylphenyl)-N-(pyrimidin-5-ylmethyl)-(1,2-dichloropropane)sulfonamide N-(2,4-diethylphenyl)-N-[1-(pyridin-2-yl)ethyl-(1,1,1-tribromoisopropane)sulfonamide, oxide N-(4-propylbenzyl)-N-(pyrimidin-5-ylmethyl)-chloromethanesulfonamide N-(3-ethyl-5-methylphenyl)-N-(pyridin-3-ylmethyl)-(2,2-difluoroethane)sulfonamide, butyrate N-(2-isopropyl-4-methylphenyl)-N-[1-(pyridin-3-yl)butyl]-dibromomethanesulfonamide, hydrobromide N-(pyridin-4-ylmethyl)-N-(3-trifluoromethylphenyl)-(1-chloro-2-bromoethane)sulfonamide, N-(4-bromomethylbenzyl)-N-(pyridin-3-ylmethyl)-(3,3,3-trifluoropropane)sulfonamide N-(4-pentabromoethylbenzyl)-N-(pyrimidin-5-yl)benzenesulfonamide N-[1-(pyridin-3-yl)ethyl]-N-(3-heptafluoropropylbenzyl)-(3-fluorobenzene)sulfonamide N-[2-[2-(2,2-dichloroethyl)phenyl]ethyl]-N-(pyridin-2-ylmethyl)-(2,4-difluorobenzene)sulfonamide, hydrochloride N-[4-(1,2,3-tribromoisopropyl)phenyl]-N-(pyridin-2-ylmethyl)-(4-chlorobenzene)sulfonamide N-(pyridin-3-ylmethyl)-N-[2,4-bis(trifluoromethyl)phenyl]-(2,3-dichlorobenzene)sulfonamide, hydrochloride N-[4-(1-chloroethyl)-2-trifluoromethylphenyl]-N-[1-(pyrimidin-5-yl)propyl]-(2-bromobenzene)sulfonamide N-(2-chloromethyl-5-heptafluoropropylphenyl)-N-(pyrdin-3-yl)-(3,5-dibromobenzene)sulfonamide, oxide N-[3,5-bis(bromomethyl)phenyl]-N-(pyridin-4-ylmethyl)-(4-iodobenzene)sulfonamide N-[2,6-bis(fluoromethyl)benzyl]-N-(pyridin-3-ylmethyl)-(2,5-diiodobenzene)sulfonamide, acetate N-(3-methoxyphenyl)-N-(pyridin-2-ylmethyl)-(3-methylbenzene)sulfonamide N-(4-ethoxyphenyl)-N-(pyridin-3-ylmethyl)-(2-propylbenzene)sulfonamide N-(2-isopropoxyphenyl)-N-[1-(pyrimidin-5-yl)ethyl]-(2-ethyl-4-isopropylbenzene)sulfonamide, hydrochloride N-(3,4-diethoxyphenyl)-N-(pyridin-3-ylmethyl)-3-trifluoromethylbenzene)sulfonamide, hydrochloride N-(5-ethoxy-2-methoxyphenyl)-N-(pyridin-3-ylmethyl)-[2-dichloromethyl-4-(1,1,2,2-tetrafluoroethyl)benzene]sulfonamide N-(2,6-dipropoxybenzyl)-N-(pyrimidin-5-ylmethyl)-[3-(2,2,2-tribromoethyl)-5-fluoromethylbenzene]sulfonamide N-[1-(pyridin-2-yl)ethyl]-N-[2-(2-trifluoromethoxyphenyl)ethyl]-(4-chloro-2-fluorobenzene)sulfonamide, oxide N-[2-[4-(1-chloroethoxy)phenyl]ethyl]-N-[1-(pyridin-3-yl)ethyl]-(4-bromo-3-fluorobenzene)sulfonamide, oxide N-(pyridin-4-ylmethyl)-N-(3-heptafluoropropoxyphenyl)-(2-fluoro-5-iodobenzene)sulfonamide N-[4-(1,1,2-tribromoethoxy)phenyl]-N-(pyridin-3-ylmethyl)-(2-ethyl-3-fluorobenzene)sulfonamide, acetate N-[2-(1,1,3-tribromoisopropoxy)phenyl]-N-(pyridin-3-ylmethyl)-(4-fluoro-2-heptafluoropropylbenzene)sulfonamide N-[4-(1,1,2,2-tetrafluoroethoxy)-2-trifluoromethoxyphenyl]-N-(pyridin-3-yl)-(2-chloro-3-iodobenzene)-sulfonamide, hydrobromide N-(2-chloromethoxy-3-pentafluoroethoxyphenyl)N-[1-(pyridin-3-yl)butyl]-(2-chloro-3-iodobenzene)sulfonamide N-3-(2,2-dibromoethoxy)-4-(3-chloropropoxy)phenyl]-N-(pyridin-4-yl)-(3-chloro-4-isopropylbenzene)sulfonamide N-[(2-fluorophenyl)(pyrimidin-5-yl)methyl]-N-(3-methylthiophenyl)-(4-chloro-2-trifluoromethylbenzene)sulfonamide N-(4-ethylthiophenyl)-N-(pyrimidin-5-yl)-(4-bromo-2-iodobenzene)sulfonamide, hydrochloride N-(2-propylthiobenzyl)-N-(pyrimidin-5-ylmethyl)-(3-bromo-4-methylbenzene)sulfonamide N-(3,4-dimethylthiobenzyl)-N-(pyridin-4-ylmethyl)-(2-bromo-5-trichloromethylbenzene)sulfonamide, oxide N-[(3-chlorophenyl)(pyridin-2-yl)methyl]-N-(2,6-diethylthiophenyl)-(2-iodo-4-propylbenzene)sulfonamide, hydroiodide N-[2-(5-isopropylthio-3-methylthiophenyl)ethyl]-N-(pyridin-2-ylmethyl)-(3-pentabromoethyl-4iodobenzene)sulfonamide N-(3-hydroxyphenyl)-N-(pyrimidin-5-ylmethyl)[5(2-bromopropyl)-2-ethylbenzene]sulfonamide N-(2,6-dihydroxyphenyl)-N-(pyridin-4-ylmethyl)methanesulfonamide, methanesulfonate N-(4-nitrophenyl)-N-1-(pyridin-3-yl)propyl]methanesulfonamide N-(3,5-dinitrobenzyl)-N-(pyridin-3-yl)-ethanesulfonamide N-(2-cyanophenyl)-N-(pyridin-3-ylmethyl)-(4trifluoromethylbenzene)sulfonamide, oxide N-(2,4-dicyanophenyl)-N-(pyrimidin-5-ylmethyl)-N',N'-dimethylsulfamide, hydrochloride N-(3-cyclopropylmethoxyphenyl)-N-[(4-bromophenyl)(pyrimidin-5-yl)methyl]-methanesulfonamide N-(4-cyclobutylmethoxyphenyl)-N-[1-(pyridin-2-yl)ethyl]-methanesulfonamide
N-(3-cyclooctylmethoxyphenyl)-N-(pyridin-3-yl)-methanesulfonamide, sulfonate
N-[2-(3-chloro-4-fluorophenyl)ethyl]-N',N'-diethyl-N-(pyridin-3-yl)sulfamide, sulfonate
N-(5-bromo-2-fluorophenyl)-N-(pyridin-3-ylmethyl)-(3-chlorobenzene)sulfonamide
N-(4-fluoro-2-iodophenyl)-N-(pyridin-3-ylmethyl)-methanesulfonamide
N-(3-fluoro-5-methylbenzyl)-N-(pyridin-3-ylmethyl)-(4-fluorobenzene)sulfonamide, oxide
N-[2-fluoro-4-(1,1,2,2-tetrafluoroethyl)phenyl]-N-(pyridin-4-yl)-methanesulfonamide
N-(2-ethoxy-4-fluorophenyl)-N-[2-(pyridinyl)-2-ylmethyl]-methanesulfonamide
N-[3-(2,2-dichloroethoxy)-3-fluorophenyl]-N-(pyrimidin-5-ylmethyl)-(4-bromobenzene)sulfonamide
N-(4-fluoro-2-propylthiobenzyl)-N-[(2-iodophenyl)(pyrimidin-5-yl)methyl]-methanesulfonamide
N-(3-fluoro-4-hydroxyphenyl)-N-(pyridin-3-ylmethyl)-methanesulfonamide, hydrochloride
N-(4-fluoro-2-nitrophenyl)-N-(pyridin-3-ylmethyl)-(4-trifluoromethylbenzene)sulfonamide
N-(3-cyano-4-fluorophenyl)-N-(pyridin-3-ylmethyl)-ethanesulfonamide
N-(4-bromo-3-chlorobenzyl)-N-(pyrimidin-5-ylmethyl)-methanesulfonamide, hydroiodide
N-(2-chloro-5-iodophenyl)-N-(pyridin-4-yl)methanesulfonamide
N-(4-chloro-2-ethylphenyl)-N-(phenyl)(pyridin-3-yl)methyl]-(4-chlorobenzene)sulfonamide
N-(3-chloro-4-trifluoromethylphenyl)-N-[1-(pyridin-3-yl)ethyl]-methanesulfonamide, hydrochloride
N-(2-chloro-5-isopropoxyphenyl)-N-(pyridin-3-yl)-methanesulfonamide, oxide
N-[4-chloro-2-(3-chloropropoxy)phenyl]-N-(pyridin-4-ylmethyl)-hexanesulfonamide, oxide
N-(3-chloro-2-ethylthiophenyl)-N-(pyrimidin-5-yl)-methanesulfonamide
N-(4-chloro-3-hydroxyphenyl)-N-[1-(pyrimidin-5-yl)ethyl]-pentanesulfonamide
N-[2-(2-chloro-4-nitrophenyl)ethyl]-N-(pyridin-3-ylmethyl)-hexanesulfonamide
N-(3-chloro-2-cyanophenyl)-N-(pyridin-3-ylmethyl)-methanesulfonamide, hydrochloride
N-(2-bromo-4-iodophenyl)-N-(pyridin-3-ylmethyl)methanesulfonamide
N-(3-bromo-2-propylphenyl)-N-(pyridin-3-ylmethyl)-methanesulfonamide, oxide
N-[2-bromo-5-(2,2-dichloroethyl)phenyl]-N-(pyridin-3-ylmethyl)-methanesulfonamide, oxide
N-(4-bromo-3-isopropoxyphenyl)-N-(pyridin-4-ylmethyl)-t-butanesulfonamide, acetate
N-[3-bromo-5-(2-bromopropoxy)benzyl]-N-[1-(pyrimidin-5-yl)butyl]-methanesulfonamide
N-(4-bromo-2-methylthiophenyl)-N-(pyrimidin-5-ylmethyl)-methanesulfonamide
N-(3-bromo-2-hydroxyphenyl)-N-(pyridin-3-ylmethyl)-propanesulfonamide, propionate
N-(2-bromo-6-nitrophenyl)-N-(pyridin-2-ylmethyl)-methanesulfonamide
N-(2-bromo-4-cyanophenyl)-N-(pyridin-4-ylmethyl)-(4-bromobenzene)sulfonamide, hydrochloride
N-(3-iodo-5-propylphenyl)-N-[1-(pyrimidin-5-yl)ethyl]-methanesulfonamide
N-[2-(1-bromoethyl)-6-iodophenyl]-N-(pyridin-3-ylmethyl)-methanesulfonamide, oxide
N-(3-iodo-4-propoxyphenyl)-N-(pyridin-3-ylmethyl)-methanesulfonamide, oxide
N-(4-iodo-3-trifluoromethoxybenzyl)-N-(pyridin-3-ylmethyl)-methanesulfonamide
N-[2-(4-ethylthio-2-iodophenyl)ethyl]-N-(pyridin-3-yl)-butanesulfonamide, hydrochloride
N-[(2-fluorophenyl)(pyridin-3-yl)methyl]-N-(2-hydroxy-3-iodophenyl)-methanesulfonamide
N-(2-iodo-4-nitrophenyl)-N-(pyridin-3-ylmethyl)methanesulfonamide
N-(3-cyano-5-iodophenyl)-N-[(phenyl)(pyrimidin-5-yl)methyl]-(3-fluorobenzene)sulfonamide
N-[5-(1-bromoisopropyl)-2-ethylphenyl]-N-(pyridin-3-yl)-methanesulfonamide, oxide
N-(4-ethoxy-3-methylphenyl)-N-[1-(pyrimidin-5-yl)ethyl]-methanesulfonamide
N-[3-(2,2-difluoroethoxy)-4-propylphenyl]-N-(pyridin-4-ylmethyl)-methanesulfonamide
N-(2-isopropyl-4-isopropylthiophenyl)-N-(pyridin-2-ylmethyl)-ethanesulfonamide
N-(3-hydroxy-4-methylphenyl)-N-(pyridin-3-ylmethyl)-(4-chlorobenzene)sulfonamide, acetate
N-(2-nitro-3-propylphenyl)-N-(pyridin-3-ylmethyl)-methanesulfonamide
N-(2-cyano-4-methylphenyl)-N-(pyridin-4-ylmethyl)-(4-fluorobenzene)sulfonamide
N-(2-methoxy-4-trifluoromethylphenyl)-N-[1-(pyrimidin-5-yl)ethyl]-methanesulfonamide, hydrofluoride
N-(3-chloromethyl-5-pentafluoroethoxyphenyl)-N-(pyrimidin-5-yl)-methanesulfonamide
N-[4-(3,3,3-tribromopropyl)-2-isopropylthiophenyl]-N-(pyridin-3-ylmethyl)-methanesulfonamide, oxide
N-[3-(1,2-dichloroethyl)-2-hydroxybenzyl]-N-[(phenyl)(pyridin-3-yl)methyl]-methanesulfonamide, nitrate
N-(3-dichloromethyl-4-nitrophenyl)-N-(pyridin-3-yl)-propanesulfonamide, oxide
N-[5-(1,3-dibromoisopropyl)-2-cyanophenyl]-N-(pyrimidin-5-ylmethyl)-t-butanesulfonamide, hydrochloride
N-(5-heptafluoropropoxy-2-methoxyphenyl)-N-(pyrimidin-5-ylmethyl)-methanesulfonamide
N-(4-ethoxy-2-ethylthiophenyl)-N-[1-(pyrimidin-5-yl)butyl]-propanesulfonamide
N-(3-hydroxy-5-propoxyphenyl)-N-(pyridin-3-yl)-isopropanesulfonamide
N-(3-isopropoxy-4-nitrobenzyl)-N-(pyridin-2-yl)-(4-methylbenzene)sulfonamide
N-(3-cyano-2-methoxybenzyl)-N-(pyridin-4-ylmethyl)-(3-chlorobenzene)sulfonamide
N-(4-methylthio-2-trifluoromethoxyphenyl)-N-(pyridin-2-ylmethyl)-methanesulfonamide, oxide
N-[2-hydroxy-4-(2,2,2-trichloroethoxy)phenyl]-N-[1-(pyrimidin-5-yl)ethyl]-methanesulfonamide
N-[(2,2-dibromoethoxy)-4-nitrophenyl]-N-(pyrimidin-5-ylmethyl)-methanesulfonamide
N-(2-cyano-3-fluoromethoxybenzyl)-N-(pyrimidin-5-yl)-benzenesulfonamide, hydrobromide
N-[(3-fluorophenyl)(pyrimidin-5-yl)methyl]-N-(3-hydroxy-2-methylthiobenzyl)-N',N'-dimethylsulfamide
N-(3-ethylthio-5-nitrophenyl)-N'-propyl-N-(pyridin-4-ylmethyl)sulfamide, oxide
N-2-(4-cyano-3-propylthiophenyl)ethyl]-N-(pyridin-3-ylmethyl)-methanesulfonamide
N,N-diethyl-N'-(2-hydroxy-4-nitrophenyl)-N'-(pyrimidin-5-ylmethyl)sulfamide N-(2-cyano-3-hydroxyphenyl)-N-(pyrimidin-5-ylmethyl)-methanesulfonamide N-(4-cyano-2-nitrobenzyl)-N-(pyrimidin-5-ylmethyl)-benzenesulfonamide.

The compounds of the present invention are made by processes which are analogous to processes for preparing similar, known compounds. The final step in the most convenient synthetic scheme is the sulfonation of a substituted amine of the formula $$R^1\text{-}(CHR)_n\text{-}NH\text{-}(CH_2)_m\text{-}R^2 \quad (A)$$

The substituted amine is sulfonated with an active form of the sulfonic acid of the formula $$R^3\text{-}SO_2OH \quad (B)$$

Most conveniently, the sulfonic acid of formula B is used in the form of its sulfonyl halide, especially the sulfonyl chloride or bromide. When a sulfonyl halide is used, it is advisable to include in the reaction mixture a hydrohalide scavenger. Preferably, moderately strong bases are used for that purpose; the alkali metal carbonates, bicarbonates and hydroxides are quite convenient as hydrohalide scavengers. However, other bases can be used if necessary, including hydrides of alkali and alkali earth metals, and tertiary amines, such as triethylamine, triethanolamine and the like.

Another convenient form of the sulfonic acid of formula B is its anhydride, either formed by condensing two molecules of the sulfonic acid or by condensing that acid with another acid. When the anhydride is used as the sulfonating agent, it is not necessary to include an acid scavenger or other reaction initiator or catalyst in the mixture.

Sulfonations are most conveniently carried out in an inert organic solvent, preferably a solvent whose boiling point provides a convenient reflux temperature. It has been found that halogenated alkane solvents are particularly convenient; dichloromethane, chloroform and the like are particularly mentioned. However, any organic solvent which does not react with the amine or the sulfonic acid, and which is stable at the desired reaction temperature, may be used. For example, aromatics, amides, ketones and the like can be used and may be preferred for the synthesis of some particular compounds.

In general, the sulfonations are carried out at moderate temperatures in the range from the ambient temperature to about 100°. Most preferably, the reactions are carried out at moderately elevated temperatures from about 30° to about 70°. As usual, the most advantageous temperature for a given synthesis must be found experimentally, taking into account the throughput of the equipment and the desired percentage yield of the product.

The sulfonations go reasonably well with equimolar quantities of the reactants. As usual, however, if one reactant is particularly expensive or hard to obtain, a substantial excess of the other reactant should be used to assure complete consumption of the critical reactant.

The substituted amine of formula A is prepared, most preferably, by reacting an aldehyde or ketone of the formula $$\begin{array}{c} R \\ | \\ R^1\text{—}C\text{=}O \end{array} \quad (C)$$

with an amine of the formula $$H_2N\text{-}(CH_2)_m\text{-}R^2 \quad (D)$$

The reactions go readily, most preferably at the reflux temperature, with a water trap to drive the equilibrium toward the reaction product of the formula $$\begin{array}{c} R \\ | \\ R^1\text{—}C\text{=}N\text{—}(CH_2)_m\text{—}R^2 \end{array}$$

The condensation of the aldehyde or ketone and the amine is preferably carried out in a water-immiscible solvent of high boiling point, such as xylene or toluene, and in the presence of a very small amount of an initiator such as toluenesulfonic acid.

The imine of formula E is readily reduced by either chemical or catalytic methods to form the amine of formula A. It is preferred to reduce the imine chemically, as by reduction with a borohydride or cyanoborohydride. Such reactions are conventionally carried out in an alcohol solvent at moderate temperatures in the range of from the ambient temperature to about 100°.

The amine of formula A, wherein m and n are not 0, is also readily prepared by the reaction of an amine with a halogenated derivative, as shown below.

$$R^1\text{-}(CHR)_n\text{-}NH_2 + X\text{-}(CH_2)_m\text{-}R^2 \rightarrow (A) \quad (F)$$

$$R^1\text{-}(CHR)_n\text{-}X + H_2N\text{-}(CH_2)_m\text{-}R^2 \rightarrow (A) \quad (G)$$

In the above equations F and G, X is halogen, preferably chlorine or bromine, or is another convenient "leaving group", such as a sulfonate group or the like. Such reactions are carried out in the presence of acid scavengers similar to those used in the sulfonation, discussed above, which forms the compounds of the present invention.

Further, the amine of formula A is readily made by reacting an acyl halide of the formula $$\begin{array}{c} O \\ \| \\ R^1\text{—}C\text{—}X^1 \end{array} \quad (H)$$

where $X^1$ is fluoro, chloro or bromo, with an amine of the formula $$H_2N\text{-}(CH_2)_m\text{-}R^2 \quad (I)$$

to prepare an amide of the formula $$\begin{array}{c} O \\ \| \\ R^1\text{—}C\text{—}NH\text{—}(CH_2)_m\text{—}R^2. \end{array} \quad (J)$$

That amide is reduced to prepare the amine of formula A wherein n is 1 and R is hydrogen. The above reaction of the acyl halide and amine are carried out in the presence of an acid scavenger, as discussed above, and at moderately elevated temperatures in inert solvents such as halogenated alkanes, aromatics, amides, ketones and the like. The amide is reduced chemically, preferably with lithium aluminum hydride in an ether solvent at ambient or moderately elevated temperatures.

When a pyridine oxide is the desired product, the pyridine group is oxidized as a final step with a strong oxidizing agent. Chloroperbenzoic acid is conventionally used for such oxidations and is preferred. Other strong oxidizing agents are of course also useful, and may be used when necessary.

The acid addition salts of the present compounds are easily formed by mere contact of the product with the appropriate acid. Such acids as hydrochloric, hydrobromic, hydroiodic, acetic, propionic, butyric, lactic, hexanoic, sulfuric, nitric, phosphoric, orthophosphoric, and the like can be used as desired to form acid addition salts. Preferably, such salts are prepared by dissolving the free base form of the compound in a suitable solvent, which may be an aromatic such as benzene or toluene, or a halogenated alkane, most preferably, and adding an excess amount of the desired acid. It is convenient to add an acid, such as hydrochloric acid, in the gas form by bubbling it through the solution with good agitation.

The following examples further illustrate the synthesis and isolation of the compounds of the present invention.

Preparation 1

3-(4-chlorophenylaminomethyl)pyridine

A 63.8 g. portion of 4-chloroaniline was dissolved in 250 ml. of toluene and 47.2 ml. of 3-pyridinecarboxaldehyde was added. A very small amount of p-toluenesulfonic acid was added, and the mixture was then heated to boiling and refluxed for 6 hours, collecting the water which evolved in a trap. About 8.5-9 ml. of water was collected. The mixture was then cooled, and the solvent was removed under vacuum. The residue was triturated well with petroleum ether and filtered, and the solids were washed with additional petroleum ether and dried to obtain 88.6 g. of impure product, which was dissolved in warm methanol. The precipitate which formed upon cooling was triturated with additional methanol, and the suspension was filtered. The solids were washed with additional cold methanol and petroleum ether, and air-dried to obtain 49.6 g. of 3-(4-chlorophenyliminomethyl)pyridine, m.p. 65°-68°.

The above product was dissolved in ethanol, and 8.9 g. of sodium borohydride was added slowly. The mixture was stirred overnight at ambient temperature, the ethanol was evaporated. The residue was dissolved in ethyl acetate, and the solution was extracted several times with water. The organic solution was dried over magnesium sulfate, with charcoal, and filtered, and the filtrate was evaporated under vacuum. The residue was taken up in ethyl acetate, and applied to a silica gel column in additional ethyl acetate. The product-containing fractions were combined and evaporated under vacuum to obtain 23.1 g. of the desired product, m.p. 95°-98°.

EXAMPLE 1 b 4-chlorophenyl)-N-(pyridin-3-ylmethyl)-(3-chloropropane)sulfonamide

A 1.9 g. portion of the product of Preparation 1 was dissolved in dichloromethane with stirring, and to it were added 1.4 g. of potassium carbonate and 1.2 ml. of 3-chloropropanesulfonyl chloride. The mixture was stirred at ambient temperature for several days, and was then extracted twice with water. The organic layer was dried over magnesium sulfate, filtered and evaporated to an oily residue. The residue was dissolved in chloroform and was chromatographed over a silica gel column, eluting with chloroform. The product-containing fractions were combined and evaporated under vacuum to obtain 0.4 g. of the desired product, having the following elemental analysis.

Theory: C, 50.15; H, 4.49; N, 7.80; Found: C, 49.90; H, 4.42; N, 7.57.

EXAMPLE 2

N-(2,6-diethylphenyl)-N-(pyridin-3-ylmethyl)methanesulfonamide

A 3.9 g. portion of 3-(2,6-diethylphenylaminomethyl)pyridine was suspended in about 10 ml. of methanesulfonyl chloride, and the mixture stood at ambient temperature for 3 days. It was then diluted with water, and made basic to about pH 10 with aqueous sodium hydroxide. It was extracted twice with 15 ml. portions of ethyl acetate, and the combined organic layers were washed twice with 15 ml. portions of water, and dried. The organic solution was evaporated under vacuum to obtain 4.5 g. of oily product. It was dissolved in ethyl acetate and purified over a short silica gel column in ethyl acetate. The product-containing fractions were combined and evaporated to obtain 3.5 g. of impure product. It was dissolved in 10 ml. of dichloromethane, and to it were added 1.26 ml. of triethylamine and 0.7 ml. of methanesulfonyl chloride. The mixture was stirred at ambient temperature for 3 days, and was then filtered, and the filtrate was evaporated under vacuum. The residue was dissolved in chloroform and purified over a silica gel column, eluting with 19:1 chloroform:methanol. The product-containing fractions were combined and evaporated under vacuum to obtain 3.7 g. of product, which was still only about 60% pure.

EXAMPLE 3

N-(4-fluorophenyl)-N-[1-(pyridin-3-yl)ethyl]methanesulfonamide

A 10.8 g. portion of 3-[1-(4-fluorophenylamino)ethyl]pyridine was dissolved in 50 ml. of dichloromethane and 10.4 g. of potassium carbonate was added, followed by 5.9 ml. of methanesulfonyl chloride. The mixture was stirred for two days at ambient temperature, 1.8 ml. more methanesulfonyl chloride was added, and the mixture was then stirred under gentle reflux for four days. It was then cooled, extracted twice with water, dried and concentrated to an oil. The oil was dissolved in dichloromethane and chromatographed on silica gel, eluting with dichloromethane, then with chloroform, and finally with chloroform:acetone to obtain 10.7 g. of oily product. It crystallized upon seeding, m.p. 82°-85°.

Theory: C, 57.13; H, 5.14; N, 9.52; Found: C, 56,83; H, 5.44; N, 9.38.

EXAMPLE 4

N-(4-chlorophenyl)-N-(pyridin-3-ylmethyl)chloromethanesulfonamide

A 2.6 g. portion of 3-(4-chlorophenylaminomethyl)pyridine was dissolved in dichloromethane with stirring, and to the solution was added 2.1 g. of potassium carbonate and 2.25 g. of chloromethanesulfonyl chloride. The mixture was stirred at ambient temperature for several days, and was then worked up as described in Example 3 to obtain 0.6 g. of the desired product, m.p. 98°–100°.

Theory: C, 47.14; H, 3.65; N, 8.46; Found: C, 47.25; H, 3.57; N, 8.45.

EXAMPLE 5

N-(4-chlorophenyl)-N-(pyridin-3-ylmethyl)methanesulfonamide

A 5.5 g. portion of 3-(4-chlorophenylaminomethyl)pyridine was dissolved in 50 ml. of dichloromethane and 3.8 g. of potassium carbonate was added. To it was added, dropwise with stirring, 2.4 ml. of methanesulfonyl chloride. The mixture was stirred at ambient temperature for several days, and it was then washed twice with water, dried and concentrated to a solid. It was triturated with petroleum ether and dried to obtain 7.1 g. of the desired product, m.p. 137.5°–140.5°. It was further triturated with diethyl ether and dried to obtain 7.0 g. of purified product, m.p. 137°–141°.

Theory: C, 52.61; H, 4.42; N, 9.44; Found: C, 52.39; H, 4.32; N, 9.27.

EXAMPLE 6

N-(2,4-dichlorophenyl)-N-(pyridin-3-ylmethyl)methanesulfonamide

A 2.7 g. portion of 3-(2,4-dichlorophenylaminomethyl)pyridine was dissolved in dichloromethane and reacted with 0.9 ml. of methanesulfonyl chloride in the presence of 1.4 g. of potassium carbonate at ambient temperature for several days. The reaction mixture was worked up as described in Example 4 to obtain 3.2 g. of oil, which was triturated with petroleum ether and then diethyl ether and filtered to obtain 2.8 g. of solid. The solid was triturated with chloroform, filtered and dried to obtain 0.9 g. of the desired product, m.p. 180°–186°. Its elemental analysis was as follows.

Theory: C, 47.14; H, 3.65; N, 8.46; Found: C, 47.42; H, 3.43; N, 8.72.

EXAMPLE 7

N-(4-chlorophenyl)-N-(pyridin-3-ylmethyl)(4-methylbenzene)sulfonamide

A 1.9 g. portion of 3-(4-chlorophenylaminomethyl)pyridine was dissolved in dichloromethane and reacted with 1.91 g of p-toluenesulfonyl chloride in the presence of 1.4 g. of potassium carbonate at ambient temperature overnight. The mixture was then worked up as described in Example 4 to obtain an oil, which was dissolved in chloroform and purified over a silica gel column, eluting first with chloroform and then with 19:1 chloroform:ethyl acetate. The product-containing fractions were combined and evaporated under vacuum to obtain 1.2 g. of oily solid, which was triturated in diethyl ether and petroleum ether, filtered and dried to obtain 0.9 g. of the desired product, m.p. 90°–91°. Its elemental analysis was as follows.

Theory: C, 61.20; H, 4.60; N, 7.51; Found: C, 61.16; H, 4.47; N, 7.70.

EXAMPLE 8

N-(4-chlorophenyl)-N',N'-dimethyl-N-(pyridin-3-ylmethyl)sulfamide

A 2.8 g. portion of 3-(4-chlorophenylaminomethyl)pyridine was dissolved in dichloromethane, and to it was added 2.1 g. of potassium carbonate and 1.6 ml. of dimethylsulfamoyl chloride. The mixture was stirred at ambient temperature for 1 day, and was then stirred under gentle heating for 3 days. The solvent was then evaporated under vacuum, and the oily residue was purified by chromatography on silica gel in chloroform to obtain 3.9 g. of the desired product. Its elemental analysis was as follows.

Theory: C, 51.61; H, 4.95; N, 12.97; Found: C, 51.37; H, 4.92; N, 12.60.

EXAMPLE 9

N-(4-chlorophenyl)-N-(pyridin-3-ylmethyl)isopropanesulfonamide

A 3.3 g. portion of 3-(4-chlorophenylaminomethyl)pyridine was dissolved in chloroform and reacted with 2.4 g. of isopropanesulfonyl chloride in the presence of 2.3 g. of potassium carbonate for several days at ambient temperature. The reaction mixture was worked up as described in Example 4, and the oily product was dissolved in chloroform and purified over silica gel, eluting with chloroform, to obtain 0.6 g. of the desired product, the elemental analysis which was as follows.

Theory: C, 55.46; H, 5.28; N, 8.62; Found: C, 55.18; H, 5.45; N, 8.91.

EXAMPLE 10

N-(1-methylhexyl)-N-(pyridin-3-ylmethyl)methanesulfonamide

A 3.1 g. portion of 3-(1-methylhexylaminomethyl)pyridine was dissolved in dichloromethane with stirring, and to it were added 2.1 g. of potassium carbonate and 1.16 ml. of methanesulfonyl chloride with cooling in an ice bath. The mixture was stirred at ambient temperature for 4 days. The reaction mixture was then extracted twice with 15 ml. portions of water, and the organic layer was dried over magnesium sulfate, filtered and evaporated under vacuum. The residue was dissolved in ethyl acetate and purified by chromatography over silica gel in ethyl acetate. The product-containing fractions were combined to obtain 1.7 g. of the desired product. Elemental analysis:

Theory: C, 59.12; H, 8.51; N, 9.85; Found: C, 58.86; H, 8.33; N, 9.57.

EXAMPLE 11

N-(4-phenoxyphenyl)-N-(pyridin-3-ylmethyl)methanesulfonamide

A 5.5 g. portion of 3-(4-phenoxyphenylaminomethyl)pyridine was dissolved in dichloromethane, and reacted with 1.7 ml. of methanesulfonyl chloride in the presence of 3 g. of potassium carbonate. The mixture was stirred at ambient temperature for several days. It was diluted with dichloromethane, extracted with water, dried over magnesium sulfate, and evaporated under vacuum. The residue was triturated in diethyl ether and petroleum ether, filtered and dried to obtain 6.4 g. of the desired product, m.p. 139°–140°.

Theory: C, 64.39; H, 5.12; N, 7.90; Found: C, 64.63; H, 4.89; N, 7.69.

EXAMPLE 12

N-(2,4-dichlorobenzyl)-N-(pyridin-3-ylmethyl)methanesulfonamide

A 3.2 g. portion of 3-(2,4-dichlorobenzylaminomethyl)pyridine was dissolved in 15 ml. of dichloromethane, and to it was added 2 g. of potassium carbonate and 1.16 ml. of methanesulfonyl chloride. The mixture was stirred at ambient temperature for several days, and was then extracted twice with 15 ml. portions of water, dried, filtered, and evaporated under vacuum to an oil. The residue was dissolved in chloroform and purified over silica gel, eluting first with chloroform and then with 9:1 chloroform:acetone. The product-containing fractions were combined and evaporated under vacuum to obtain 2.9 g. of impure product, which was triturated with petroleum ether to obtain 2.1 g. of the desired product, m.p. 78°–80°.

Theory: C, 48.71; H, 4.09; N, 8.11; Found: C, 48.79; H, 4.17; N, 8.24.

EXAMPLE 13

N-(2,4-difluorophenyl)-N-(pyridin-3-ylmethyl)methanesulfonamide

A 8.9 g. portion of 3-(2,4-difluorophenylaminomethyl)pyridine was dissolved in 30 ml. of dichloromethane, and to it was added 6.9 g. of potassium carbonate and 3.9 ml. of methanesulfonyl chloride. The mixture was stirred at ambient temperature for several days, and then was heated and stirred at the reflux temperature overnight. It was then cooled, extracted with aqueous sodium bicarbonate, dried over magnesium sulfate and evaporated to a small volume. The residue was chromatographed over silica gel, eluting first with dichloromethane and then with 9:1 dichloromethane:ethyl acetate. The product-containing fractions were combined and evaporated to obtain impure product, which was triturated with diethyl ether and dried to obtain 5.6 g. of the desired product, m.p. 132°–135°.

Theory: C, 52.34; H, 4.05; N, 9.39; Found: C, 52.42; H, 4.15; N, 9.58.

EXAMPLE 14

N-(4-cyanophenyl)-N-(pyridin-3-ylmethyl)methanesulfonamide

A 4.2 g. portion of 3-(4-cyanophenylaminomethyl)pyridine was dissolved in 25 ml. of dichloromethane, and 4.1 g. of potassium carbonate and 2.4 ml. of methanesulfonyl chloride were added. The mixture was stirred at ambient temperature for 4 days, and was then diluted with 30 ml. of dichloromethane. It was then extracted with 20 ml. of water, dried over magnesium sulfate, and evaporated to an oily residue. The residue was applied to a silica gel column and eluted with dichloromethane. The product-containing fractions were combined and evaporated, and the residue was triturated with diethyl ether to obtain 1 g. of the desired product, m.p. 73°–75°.

Theory: C, 58.52; H, 4.56; N, 14.62; Found: C, 58.25; H, 4.73; N, 14.40.

EXAMPLE 15

N-(pyridin-3-ylmethyl)-N-[4-(2,2,2-trifluoroethoxy)phenyl]-methanesulfonamide

A 4.2 g. portion of 3-[4-(2,2,2-trifluoroethoxy)phenylaminomethyl]pyridine was dissolved in 15 ml. of dichloromethane, and to it were added 2.7 g. of potassium carbonate and 1.6 ml. of methanesulfonyl chloride. The mixture was stirred at ambient temperature for 3 days, and it was then diluted with dichloromethane, extracted with 25 ml. of water, dried over magnesium sulfate and evaporated to an oil. The residue was taken up in diethyl ether, and the insoluble portion was separated. The product slowly crystallized upon standing, and the solids were triturated with petroleum ether and washed with diethyl ether and petroleum ether to obtain 3.7 g. of the desired product, m.p. 69°–70°.

Theory: C, 50.00; H, 4.20; N, 7.77; Found: C, 49.96; H, 4.15; N, 7.64.

EXAMPLE 16

N-(4-fluorophenyl)-N-[1-(pyridin-3-yl)pentyl]methanesulfonamide

A 5.5 g. portion of 3-[1-(4-fluorophenylamino)pentyl]pyridine was dissolved in 40 ml. of dichloromethane, and to it were added 3.4 g. of potassium carbonate and 1.9 ml. of methanesulfonyl chloride. The mixture was stirred at ambient temperature overnight, and then an additional 1.9 ml. of methanesulfonyl chloride was added and the mixture was stirred for 3 days with gentle heating. It was then cooled and extracted with aqueous sodium bicarbonate solution, and then with water, and it was then dried over magnesium sulfate and evaporated under vacuum. The residue was dissolved in chloroform and was purified over silica gel, eluting with chloroform, to obtain 0.7 g. of the desired product.

Theory: C, 60.69; H, 6.29; N, 8.33; Found: C, 60.97; H, 6.00; N, 8.06.

EXAMPLE 17

N-(4-chlorophenyl)-N-(pyridin-3-ylmethyl)ethanesulfonamide

A 4.37 g. portion of 3-(4-chlorophenylaminomethyl)pyridine was dissolved in 20 ml. of dichloromethane, and 4.1 g. of potassium carbonate and 3.8 g. of ethanesulfonyl chloride were added. The mixture was stirred under gentle reflux overnight, and was then allowed to stand for several days at ambient temperature. The mixture was extracted with water, dried over magnesium sulfate and filtered. The residue was taken up in chloroform and purified over silica gel, eluting with chloroform. The product-containing fractions were collected and evaporated under vacuum to obtain 1 g. of the desired product, m.p. 104°–106°.

Theory: C, 54.10; H, 4.86; N, 9.01; Found: C, 54.31; H, 4.65; N, 8.89.

EXAMPLE 18

N-(4-fluorobenzyl)-N-(pyridin-3-ylmethyl)methanesulfonamide

A 3.24 g. portion of 3-(4-fluorobenzylaminomethyl)pyridine was dissolved in 15 ml. of dichloromethane, and 2.96 g. of methanesulfonic anhydride was added. The mixture boiled briefly, and a precipitate formed. Fifteen ml. of additional dichloromethane was added, and the mixture stood at ambient temperature for 2 days. It was then diluted with 20 ml. of aqueous sodium bicarbonate solution and 5 ml. of aqueous sodium hydroxide solution, and the organic layer was washed with water, dried over magnesium sulfate and evaporated to an oil. The oil was dissolved in chloroform and purified over silica gel, eluting first with chloroform and then with chloroform:ethyl acetate. The product-containing fractions were collected and evaporated to obtain 1.2 g. of oil, which was rechromatographed to obtain 0.95 g. of the desired product.

Theory: C, 57.13; H, 5.14; N, 9.52; Found: C, 56.86; H, 5.21; N, 9.39.

EXAMPLE 19

N-(4-cyclohexylmethoxyphenyl)-N-(pyridin-3-ylmethyl)-methanesulfonamide

A 3.5 g. portion of 3-(4-cyclohexylmethoxyphenylaminomethyl)pyridine was dissolved in 15 ml. of dichloromethane, and 2.76 g. of potassium carbonate and 1.55 ml. of methanesulfonyl chloride were added. The mixture was stirred with gentle heating for 20 hours, and was then extracted with aqueous sodium bicarbonate, dried over magnesium sulfate and evaporated under vacuum. The residue was dissolved in chloroform and chromatographed over silica gel, eluting with chloroform. The product-containing fractions were combined and evaporated, and the residue was triturated with diethyl ether, filtered and dried to obtain 2.33 g. of impure product, which was further washed with diethyl ether to obtain 1.88 g. of the desired product, m.p. 36°-140°.

Theory: C, 64.14; H, 7.00; N, 7.48; Found: C, 63.93; H, 6.76; N, 7.53.

EXAMPLE 20

N-(2,4-difluorophenyl)-N-(pyridin-3-ylmethyl)trifluoromethanesulfonamide

A 3.7 g. portion of 3-(2,4-difluorophenylaminomethyl)pyridine was dissolved in dichloromethane with stirring, and cooled to −15°. To it were added 2.76 g. of potassium carbonate and, dropwise, 3.4 ml. of trifluoromethanesulfonic anhydride. The mixture was stirred overnight while it warmed to ambient temperature, and it was then extracted with aqueous sodium bicarbonate, dried over magnesium sulfate, and evaporated under vacuum. The residue was dissolved in chloroform and chromatographed over silica gel, eluting with chloroform. The product-containing fractions were collected and evaporated, and the residue was re-chromatographed over silica gel, eluting with chloroform, to obtain 1.43 g. of the desired product.

Theory: C, 44.32; H, 2.58; N, 7.95; Found: C, 44.48; H, 2.85; N, 7.91.

EXAMPLE 21

N-[2-(2,2,2-trifluoroethoxy)phenyl]-N-(pyridin-3-ylmethyl)-methanesulfonamide

A 3 g. portion of 3-[2-(2,2,2-trifluoroethoxy)phenylaminomethyl]pyridine was dissolved in 15 ml. of dichloromethane and 2.6 g. of methanesulfonic anhydride was added. The mixture was stirred at ambient temperature for 2 days, and was then diluted with 20 ml. of aqueous sodium bicarbonate, and extracted with dichloromethane. The organic solution was washed with water, dried over magnesium sulfate and partially evaporated under vacuum. The residual solution was applied to a silica gel column and eluted with ethyl acetate. The product-containing fractions were combined and evaporated under vacuum to obtain 0.54 g. of the desired product, m.p. 80°-84°.

Theory: C, 50.00; H, 4.20; N, 7.77; Found: C, 50.07; H, 4.05; N, 7.89.

EXAMPLE 22

N-(4-phenoxyphenyl)-N-(pyridin-3-ylmethyl)ethanesulfonamide

A 2.8 g. portion of 3-(4-phenoxyphenylaminomethyl)pyridine was dissolved in 100 ml. of acetonitrile, and to it were added 2 g. of potassium carbonate and 1.3 g. of ethanesulfonyl chloride. The mixture was stirred at ambient temperature for 2 days, and it was then filtered and concentrated under vacuum. The oily residue was chromatographed on silica gel, eluting with 4.1 toluene-:acetone. The product-containing fractions were evaporated under vacuum, and the residue was taken up in diethyl ether. Upon standing, a precipitate formed, which was shown to be 2.0 g. of the desired product, m.p. 79°-80°.

Theory: C, 65.20; H, 5.47; N, 7.60; Found: C, 65.42; H, 5.46; N, 7.55.

Preparation 2

5-(2,4-difluorophenylaminomethyl)pyrimidine

A 26.7 g. portion of 5-chloromethylpyrimidine was dissolved in 25 ml. of dimethylformamide, and 9.4 g. of 2,4-difluoroaniline was added, followed by 6.1 g. of sodium bicarbonate. The mixture was stirred for several days with gentle heating. It was then diluted with water and extracted with ethyl acetate. The organic layer was washed with water, dried over magnesium sulfate, and evaporated under vacuum to obtain 13.75 g. of oil. The oil was dissolved in dichloromethane and purified over silica gel, eluting with dichloromethane, to obtain 4.9 g. of the desired intermediate product.

EXAMPLE 23

N-(2,4-difluorophenyl)-N-(pyrimidin-5-ylmethyl)-methanesulfonamide

The product of Preparation 2 was dissolved in 20 ml. of dichloromethane with stirring, and to it was added 4.3 g. of methanesulfonic anhydride. The mixture was stirred at ambient temperature for several days, and it was then extracted with aqueous sodium bicarbonate and with water. The organic solution was dried over magnesium sulfate and partially evaporated, and purified over silica gel, eluting first with dichloromethane and then with chloroform. The product-containing fractions were combined to obtain 1.8 g. of the desired product, m.p. 142°-145°.

Theory: C, 48.16; H, 3.70; N, 14.04; Found: C, 48.39; H, 3.60; N, 13.88.

EXAMPLE 24

N-(2-cyanoethyl)-N-(pyridin-3-ylmethyl)-(4-chlorobenzene)sulfonamide

A 2.4 g. portion of 3-(2-cyanoethylaminomethyl)pyridine was dissolved in 15 ml. of dichloromethane with stirring, and to it were added 2.7 g. of potassium carbonate and 3.8 g. of 4-chlorobenzenesulfonyl chloride. The mixture was stirred at ambient temperature for several days, and was then diluted with water. The solids were separated by filtration and were washed with water and with diethyl ether and dried to obtain 3.25 g. of impure product. It was dissolved in hot ethyl acetate and filtered, and the filtrate was partially evaporated and diluted with diethyl ether. The resulting solids were separated by filtration and dried to obtain 2.59 g. of the desired product, m.p. 127°-129°.

Theory: C, 53.65; H, 4.20; N, 12.51;
Found: C, 53.85; H, 3.90; N, 12.54.

EXAMPLE 25

N-(2,4-difluorophenyl)-N-[1-(pyridin-3-yl)ethyl]-
methanesulfonamide

A 3.5 g. portion of 3-[1-(2,4-difluorophenylamino)e-
thyl]pyridine was dissolved in 15 ml. of dichlorometh-
ane with stirring, and 2.6 g. of methanesulfonic anhy-
dride was added. The mixture was stirred at ambient
temperature for several days, and was then extracted
with aqueous sodium bicarbonate. The organic solution
was then dried over magnesium sulfate, filtered and
evaporated to an oil. The oil was taken up in dichloro-
methane and was chromatographed over silica gel,
eluting first with dichloromethane and then with chlo-
roform. The product-containing fractions were com-
bined and evaporated under vacuum to obtain 2.79 g. of
the desired product, m.p. 76°–78°.

Theory: C, 53.84; H, 4.52; N, 8.97;
Found: C, 54.05; H, 4.38; N, 8.98.

EXAMPLE 26

N-[2-(4-chlorophenyl)ethyl]-N-(pyridin-3-ylmethyl)-
methanesulfonamide

A 2.04 g. portion of 3-[2-(4-chlorophenyl)-
ethylaminomethyl]pyridine was dissolved in 15 ml. of
dichloromethane, and 1.74 g. of methanesulfonic anhy-
dride was added. The mixture boiled briefly, and was
then stirred at ambient temperature for several days. It
was diluted with aqueous sodium bicarbonate and ex-
tracted with dichloromethane. The organic layer was
washed with aqueous sodium bicarbonate, dried over
magnesium sulfate and evaporated under vacuum. The
residue was dissolved in ethyl acetate and chromato-
graphed over silica gel, eluting with ethyl acetate. The
product-containing fractions were evaporated under
vacuum to obtain 0.78 g. of the desired product, m.p.
77°–78°.

Theory: C, 55.46; H, 5.28; N, 8.62;
Found: C, 55.59; H, 5.37; N, 8.65.

EXAMPLE 27

N-(2,4-dimethylphenyl)-N-(pyridin-3-ylmethyl)-
butanesulfonamide

A 4.2 g. portion of 3-(2,4-dimethylphenylaminome-
thyl)pyridine chloromethane, and to it were added 4.1
g. of potassium carbonate and 4.7 g. of butanesulfonyl
chloride. The mixture was stirred at ambient tempera-
ture for 4 days, and then was stirred under gentle reflux
for several days more. It was then diluted with aqueous
sodium bicarbonate and extracted with dichlorometh-
ane, and the organic layer was dried over magnesium
sulfate and evaporated to an oil. The oil was applied to
a silica gel column and eluted with dichloromethane
and then with chloroform to obtain 0.75 g. of the de-
sired product.

Theory: C, 65.03; H, 7.28; N, 8.43;
Found: C, 64.87; H, 7.41; N, 8.17.

EXAMPLE 28

N-[2-(4-chlorophenyl)ethyl]-N-(pyridin-4-ylmethyl)-
methanesulfonamide

A 7.4 g. portion of 4-[2-(4-chlorophenyl)e-
thylaminomethyl]pyridine was dissolved in 50 ml. of
dichloromethane, and to it were added 4 g. of potassium
carbonate and 4 g. of methanesulfonyl chloride. The
mixture was stirred at ambient temperature overnight,
and then 100 ml. of additional dichloromethane was
added, followed by 200 ml. of water. The organic phase
was separated, washed with water, dried and concen-
trated under vacuum. The residue was chromato-
graphed on silica gel, using acetone as the eluant. The
product-containing fractions were combined and evap-
orated, and the residue crystallized upon standing. The
solids were triturated with petroleum ether and filtered
and dried to obtain 4.0 g. of the desired product, m.p.
96°–99°.

Theory: C, 55.46; H, 5.27; N, 8.62;
Found: C, 55.55; H, 5.34; N, 8.58.

EXAMPLE 29

N-(2,4-difluorophenyl)-N-(pyridin-3-ylmethyl)me-
thanesulfonamide, oxide

A 3.0 g. portion of the compound of Example 13 was
dissolved in 15 ml. of chloroform and was cooled to 0°
with stirring. To it was added 2.1 g. of chloroperben-
zoic acid and the mixture was stirred for 30 minutes. It
was then held at 0° overnight, and was then extracted
with aqueous potassium carbonate and dried over mag-
nesium sulfate. The solvent was removed under vacuum
to obtain an oil, which was triturated with diethyl ether.
A solid formed, and was recovered by filtration to ob-
tain 2 g. of impure product, which was dissolved in
chloroform and chromatographed over a silica gel col-
umn to obtain 0.89 g. of the desired product, m.p.
139°–141°.

Theory: C, 49.68; H, 3.85; N, 8.91;
Found: C, 49.56; H, 4.04; N, 8.69.

EXAMPLE 30

N-(2-phenylethyl)-N-(pyridin-3-ylmethyl)methanesul-
fonamide

A 4.4 g. portion of 3-(2-phenylethyl)aminomethyl-
pyridine was reacted with 2.4 g. of methanesulfonyl
chloride in the presence of 4 g. of potassium carbonate
in 60 ml. of dichloromethane at ambient temperature for
several days. The mixture was then diluted with 100 ml.
of dichloromethane and extracted with 50 ml. of water.
The organic layer was dried over magnesium sulfate
and concentrated under vacuum. The residue was taken
up in toluene and chromatographed on silica gel, eluting
with 9:1 toluene:acetone. The product-containing frac-
tions were combined and evaporated under vacuum,
and the residue solidified on standing. The solids were
triturated in ether and dried to obtain 1.8 g. of the de-
sired product, m.p. 94°–95°.

Theory: C, 62.04; H, 6.25; N, 9.65;
Found: C, 61.77; H, 6.19; N, 9.62.

EXAMPLE 31

N-(2,4-difluorophenyl)-N-(pyridin-3-ylmethyl)-
butanesulfonamide

A 4.4 g. portion of 3-(2,4-difluorophenylaminome-
thyl)pyridine was dissolved in 15 ml. of dichlorometh-
ane, and to it were added 4.1 g. of potassium carbonate
and 4.7 g. of butanesulfonyl chloride. The mixture was
stirred under gentle reflux for several days, and was
then cooled and diluted with 20 ml. of aqueous sodium
bicarbonate and 5 ml. of aqueous sodium hydroxide.
Some additional dichloromethane was added, and the
suspension was shaken and the organic layer separated.
It was washed with aqueous sodium bicarbonate and
dried over magnesium sulfate, and it was then evapo-
rated to a smaller volume and was chromatographed on a silica gel column, eluting with dichloromethane. The chromatography was repeated twice to obtain 0.38 g. of the desired product.

Theory: C, 56.46; H, 5.33; N, 8.23;
Found: C, 56.26; H, 5.10; N, 8.23.

EXAMPLE 32

N-(4-chlorophenyl)-N-(pyridin-2-ylmethyl)methanesulfonamide

A 3.3 g. portion of 2-(4-chlorophenylaminomethyl)-pyridine was dissolved in 15 ml. of dichloromethane, and 2.7 g. of potassium carbonate and 1.5 ml. of methanesulfonyl chloride were added. The mixture was stirred overnight at ambient temperature, and then was stirred for 1 day under gentle reflux. Another 0.5 ml. of methanesulfonyl chloride was added, and the reflux was continued for several hours. Then the mixture was cooled and filtered, and the filtrate was chromatographed on a silica gel column, eluting with chloroform. The product-containing fractions were combined and evaporated to obtain 1 g. of the desired product.

Theory: C, 52.61; H, 4.42; N, 9.44;
Found: C, 52.85; H, 4.59; N, 9.49.

EXAMPLE 33

N-(4-chlorophenyl)-N-[1-(pyridin-3-yl)ethyl](4-chlorobenzene)sulfonamide

A 3.5 g. of 3-[1-(4-chlorophenylamino)ethyl]pyridine was dissolved in dichloromethane, and 2.7 g. of potassium carbonate and 4.2 g. of 4-chlorobenzene sulfonyl chloride were added. The mixture was stirred at ambient temperature for 3 days, and then under reflux overnight. The mixture was cooled and extracted with water, and the organic layer was dried over magnesium sulfate, filtered, and evaporated to an oil. The oil was taken up in dichloromethane and chromatographed on a silica gel column, eluting with dichloromethane. The product-containing fractions were combined and evaporated, and the residue was crystallized from diethyl ether/petroleum ether to obtain 2.7 g. of the desired product, m.p. 114°–116°.

Theory: C, 56.03; H, 3.96; N, 6.88;
Found: C, 56.08; H, 3.84; N, 6.81.

EXAMPLE 34

N-(4-chlorophenyl)-N-(pyridin-4-ylmethyl)methanesulfonamide

A 3.3 g. portion of 4-(4-chlorophenylaminomethyl)-pyridine was dissolved in 15 ml. of dichloromethane, and 2.7 g. of potassium carbonate and 1.6 ml. of methanesulfonyl chloride were added. The mixture was stirred at ambient temperature for several days, adding another 0.5 ml. of methanesulfonyl chloride in the process. The mixture was then diluted with dichloromethane, extracted with aqueous sodium bicarbonate and with water, dried over magnesium sulfate and evaporated. The residue was taken up in dichloromethane and chromatographed over silica gel, eluting first with dichloromethane and then with 9:1 dichloromethane:ethyl acetate. The product-containing fractions were combined and evaporated, and the residue was triturated with petroleum ether and diethyl ether to obtain 2.1 g. of the desired product.

Theory: C, 52.61; H, 4.42; N, 9.44;
Found: C, 52.79; H, 4.60; N, 9.42.

EXAMPLE 35

N-(4-chlorophenyl)-N',N'-dimethyl-N-[1-(pyridin-3-yl)ethyl]sulfamide

A 3.5 g. portion of 3-[1-(4-chlorophenylamino)ethyl]-pyridine was dissolved in dichloromethane and 2.7 g. of potassium carbonate and 2.9 g. of dimethylsulfamoyl chloride were added. The mixture was stirred at ambient temperature for 3 days, and was then diluted with 25 ml. of additional dichloromethane and was extracted with water. The organic layer was dried over magnesium sulfate and evaporated to an oil, which was taken up in dichloromethane and chromatographed over silica gel, eluting with chloroform. The product-containing fractions were combined and evaporated to obtain about 0.3 g. of the desired product.

Theory: C, 53.01; H, 5.34; N, 12.36;
Found: C, 53.29; H, 5.52; N, 12.40.

EXAMPLE 36

N-dodecyl-N-(pyridin-3-ylmethyl)-methanesulfonamide

A 4.1 g. portion of 3-dodecylaminomethylpyridine was dissolved in 15 ml. of dichloromethane, and 2.7 g. of potassium carbonate and 1.6 ml. of methanesulfonyl chloride were added. The mixture was stirred for 3 days at ambient temperature, and was then diluted with dichloromethane and extracted with water. The organic layer was dried and evaporated to an oil, which was dissolved in dichloromethane and chromatographed over silica gel, eluting with dichloromethane. The product-containing fractions were combined and evaporated to obtain 3.5 g. of oil which crystallized on standing, and was triturated with cold petroleum ether and diethyl ether. The solids were dried to obtain 3.2 g. of the desired product, m.p. 43°–44°.

Theory: C, 64.36; H, 9.67; N, 7.90;
Found: C, 64.24; H, 9.60; N, 7.62.

EXAMPLE 37

N-dodecyl-N-(pyridin-3-ylmethyl)-(4-chlorobenzene)-sulfonamide

A 3.8 g. portion of 3-dodecylaminomethylpyridine was dissolved in 10 ml. of dichloromethane, and 1.9 g. of potassium carbonate and 2.95 g. of 4-chlorobenzenesulfonyl chloride were added. The mixture was stirred overnight at ambient temperature, and was then extracted with water, and 20 ml. of additional dichloromethane was added. The organic phase was separated and dried, and was evaporated to an oil, which was dissolved in dichloromethane and chromatographed over silica gel, eluting first with dichloromethane and then with 9:1 dichloromethane:ethyl acetate. The product-containing fractions were combined and evaporated to obtain 4.5 g. of the desired product.

Theory: C, 63.91; H, 7.82; N, 6.21;
Found: C, 63.74; H, 7.59; N, 6.32.

EXAMPLE 38

N-cyclohexyl-N-(pyridin-3-ylmethyl)-methanesulfonamide

A 2.85 g. portion of 3-cyclohexylaminomethylpyridine was dissolved in 15 ml. of dichloromethane, and 2.8 g. of potassium carbonate and 1.6 ml. of methanesulfonyl chloride were added. The mixture boiled vigorously for a short time, and was then stirred at ambient temperature overnight. The mixture was diluted with 25 ml. of additional dichloromethane, and was extracted with 20 ml. of water and dried over magnesium sulfate. The organic solution was reduced in volume and chromatographed over silica gel, eluting first with dichloromethane and then with 9:1 dichloromethane:ethyl acetate. The product-containing fractions were evaporated under vacuum, and the residue was triturated with petroleum ether and diethyl ether to obtain 0.8 g. of the desired product.
Theory: C, 58.18; H, 7.57; N, 10.44;
Found: C, 58.40; H, 7.67; N, 10.63.

EXAMPLE 39

N-(pyridin-3-ylmethyl)-N-(3-trifluoromethylphenyl)-methanesulfonamide

A 3.8 g. portion of 3-(3-trifluoromethylphenylaminomethyl)pyridine was dissolved in 15 ml. of dichloromethane and to it was added 2.7 g. of potassium carbonate and 1.6 ml. of methanesulfonyl chloride. The mixture was stirred at ambient temperature overnight, and at a gentle reflux for another day. Another 1.6 ml. of methanesulfonyl chloride was added, and the mixture was stirred under reflux for 3 days more. It was then cooled, and diluted with 20 ml. of aqueous sodium bicarbonate. The organic phase was separated, washed with water, dried and evaporated under vacuum. The residue was triturated with diethyl ether and petroleum ether, and dried to give 4.7 g. of the desired product, m.p. 106°-110°.
Theory: C, 50.91; H, 3.97; N, 8.48;
Found: C, 51.16; H, 3.79; N, 8.77.

EXAMPLE 40

N-cyclohexyl-N-(pyridin-3-ylmethyl)-chloromethanesulfonamide

A 2.85 g. portion of 3-(cyclohexylaminomethyl)pyridine was dissolved in 20 ml. of dichloromethane, and 2.7 g. of potassium carbonate was added, followed by 3.5 g. of chloromethanesulfonyl chloride. The mixture was stirred at ambient temperature for 2 days, another 2 g. of chloromethanesulfonyl chloride was added, and the mixture was stirred for 3 days more. It was then diluted with 20 ml. of water, and the organic phase was separated, dried over magnesium sulfate and evaporated to an oil. The oil was dissolved in dichloromethane and chromatographed over silica gel, eluting with 9:1 dichloromethane:ethyl acetate. The product-containing fractions were combined and evaporated to obtain 1.4 g. of product, initially an oil, which crystallized spontaneously. M.P. 67°-72°.
Theory: C, 51.56; H, 6.32; N, 9.25;
Found: C, 51.84; H, 6.54; N, 9.29.

EXAMPLE 41

N-(4-methylthiophenyl)-N-(pyridin-3-ylmethyl)-chloromethanesulfonamide

A 3.4 g. portion of 3-(4-methylthiophenylaminomethyl)pyridine was dissolved in 25 ml. of dichloromethane, and 4.1 g. of potassium carbonate and 4.5 g. of chloromethanesulfonyl chloride were added. The mixture was stirred at ambient temperature for 4 days, and then 20 ml. of aqueous sodium bicarbonate was added. The mixture was extracted with 15 ml. of dichloromethane, and the organic phase was washed with aqueous sodium bicarbonate, dried and evaporated to an oil. The oil was dissolved in dichloromethane and chromatographed on silica gel, eluting with dichloromethane. Combination of the product-containing fractions gave 1.6 g. of the desired product.
Theory: C, 49.04; H, 4.41; N, 8.17;
Found: C, 49.19; H, 4.50; N, 7.94.

EXAMPLE 42

N-(3,4-dichlorophenyl)-N-(pyridin-3-ylmethyl)-(3-trifluoromethylbenzene)sulfonamide A 3.8 g. portion of 3-(3,4-dichlorophenylaminomethyl)pyridine was dissolved in 15 ml. of dichloromethane and 2.7 g. of potassium carbonate was added, followed by 4.9 g. of 3-trifluoromethylbenzenesulfonyl chloride. The mixture was stirred at ambient temperature for 4 days, an additional 2 g. of the sulfonyl chloride was added, and the mixture was stirred for 3 days more at the reflux temperature. The mixture was then diluted with 20 ml. of dichloromethane and extracted with 20 ml. of aqueous sodium bicarbonate. The organic layer was dried over magnesium sulfate and evaporated to a small volume. The residue was applied to a silica gel column and eluted with dichloromethane to obtain 1.7 g. of the desired product, m.p. 101°-103°.
Theory: C, 49.47; H, 2.84; N, 6.07;
Found: C, 49.25; H, 2.88; N, 5.94.

EXAMPLE 43

N-(2,4-difluorophenyl)-N-(pyridin-3-ylmethyl)methanesulfonamide, hydrochloride

A 11 g. portion of 3-(2,4-difluorophenylaminomethyl)pyridine was dissolved in 50 ml. of dichloromethane, and 4.6 ml. of methanesulfonyl chloride was added. The mixture was stirred at ambient temperature overnight. A solid had formed, which was filtered from the mixture. The filtrate was partially evaporated under vacuum, producing more solid which was removed and discarded. The filtrate was chromatographed over silica gel, eluting first with dichloromethane, then with dichloromethane:ethyl acetate, and finally with dichloromethane:methanol. The product-containing fractions were combined and evaporated to produce 1.9 g. of the desired product in the free base form. That product was dissolved in dichloromethane, with stirring, and hydrogen chloride was bubbled through the solution. Some solid formed. The mixture was diluted with 250 ml. of diethyl ether and filtered. The solids were washed with diethyl ether and dried under vacuum to obtain 2 g. of the desired product, m.p. 203°-206°.
Theory: C, 46.64; H, 3.91; N, 8.37; Cl, 10.59;
Found: C, 46.94; H, 4.15; N, 8.60; Cl, 10.81.

EXAMPLE 44

N-(4-chloro-2-methylphenyl)-N-(pyridin-3-yl-methyl)-methanesulfonamide

A 2.4 g. portion of 3-(4-chloro-2-methylphenylaminomethyl)pyridine was dissolved in 15 ml. of dichloromethane, and 2.1 g. of potassium carbonate and 2 ml. of methanesulfonyl chloride were added. The mixture was stirred at ambient temperature for several days, and then under reflux for another day. It was then cooled and diluted with 20 ml. of aqueous sodium bicarbonate and 5 ml. of 2N sodium hydroxide, 20 ml. of dichloromethane was added, and the organic layer was washed with aqueous sodium bicarbonate, dried and evaporated to an oil. The oil was dissolved in dichloromethane and chromatographed over silica gel, eluting first with dichloromethane and then with dichloromethane:ethyl acetate. The product-containing fractions were combined to obtain 1.8 g. of the desired product.

Theory: C, 54.10; H, 4.86; N, 9.01;
Found: C, 54.17; H, 5.04; N, 9.04.

EXAMPLE 45

N-(2-methylphenyl)-N-(pyridin-3-ylmethyl)methanesulfonamide.

A 10 g. portion of 3-(2-methylphenylaminomethyl)pyridine was dissolved in 100 ml. of dichloromethane, and 10 g. of potassium carbonate and 8 g. of methanesulfonyl chloride were added. The mixture was stirred at ambient temperature for 3 days, and was then diluted with 200 ml. of dichloromethane and extracted twice with 100 ml. portions of water. The organic phase was dried over magnesium sulfate and evaporated to an oil, which was chromatographed over silica gel with 1:4 acetone:toluene. The product-containing fractions were combined and evaporated, and the residue solidified upon standing and was recrystallized from hot diethyl ether to obtain 2.9 g. of the desired product, m.p. 97°–98°.

EXAMPLE 46

N-(2,4-difluorophenyl)-N-(pyridin-4-ylmethyl)methanesulfonamide

A 4.7 g. portion of 4-(2,4-difluorophenylaminomethyl)pyridine was dissolved in 15 ml. of chloroform, and 4.1 g. of potassium carbonate was added, followed by 2.3 ml. of methanesulfonyl chloride. The mixture was stirred under reflux overnight, and then for several days at ambient temperature. It was then diluted with 20 ml. of dichloromethane and 20 ml. of aqueous sodium bicarbonate, and 5 ml. of 2N sodium hydroxide was added. The organic phase was then washed with aqueous sodium bicarbonate, dried and evaporated. The residue was dissolved in dichloromethane and chromatographed over silica gel, to obtain 0.5 g. of impure product, which was triturated with diethyl ether to obtain 0.29 g. of the desired product, m.p. 101°–105°.

Theory: C, 52.34; H, 4.05; N, 9.39;
Found: C, 52.16; H, 3.84; N, 9.36.

EXAMPLE 47

N-(2,4-difluorophenyl)-N',N'-dimethyl-N-(pyridin-3-ylmethyl)sulfamide

A 3.3 g. portion of 3-(2,4-difluorophenylaminomethyl)pyridine was dissolved in 15 ml. of dichloromethane, and 2.8 g. of potassium carbonate and 3.6 g. of dimethylsulfamoyl chloride were added. The mixture was stirred at ambient temperature for several days, and was then stirred under reflux for 4 hours. The mixture was then cooled, and extracted with 20 ml. of aqueous sodium bicarbonate and with 20 ml. of water, and was dried and evaporated to an oil. The oil was dissolved in dichloromethane and chromatographed over silica gel, eluting with 9:1 dichloromethane:ethyl acetate to obtain 2.1 g. of the desired product.

Theory: C, 51.37; H, 4.62; N, 12.84;
Found: C, 51.42; H, 4.51; N, 12.96.

EXAMPLE 48

N-(2-fluorobenzyl)-N-(pyridin-4-ylmethyl)methanesulfonamide

A 4.2 g. portion of 4-(2-fluorobenzylaminomethyl)pyridine was dissolved in 50 ml. of dichloromethane, and to it was added 3 g. of potassium carbonate and 2.5 g. of methanesulfonyl chloride. The mixture was stirred at ambient temperature for 4 days, and was then diluted with 50 ml. of water and extracted with 150 ml. of dichloromethane. The organic phase was dried over magnesium sulfate, and concentrated under vacuum. The oily residue was chromatographed on silica gel, eluting with 3:2 toluene:acetone. The product-containing fractions were evaporated to obtain an oil which solidified upon standing, and was triturated with petroleum ether to obtain 3.25 g. of the desired product, m.p. 69°–70°.

Theory: C, 57.13; H, 5.14; N, 9.52;
Found: C, 57.04; H, 5.30; N, 9.52.

EXAMPLE 49

N-(4-fluorobenzyl)-N-(pyridin-3-yl)-methanesulfonamide

A 4.04 g. portion of 3-(4-fluorobenzylamino)pyridine was dissolved in 15 ml. of dichloromethane and 3.5 g. of methanesulfonic anhydride was added. The mixture was stirred at ambient temperature for 1 day, and was then stirred under reflux for 1 day more. It was then cooled and extracted with 25 ml. of aqueous sodium bicarbonate and with 20 ml. of water. The organic phase was dried and evaporated under vacuum. The residue was dissolved in dichloromethane and chromatographed over silica gel, eluting with dichloromethane. The product-containing fractions were combined and evaporated, and the residue was triturated with petroleum ether and diethyl ether to obtain 1.96 g. of the desired product, m.p. 93°–95°.

Theory: C, 55.70; H, 4.67; N, 9.99;
Found: C, 55.51; H, 4.42; N, 10.14.

EXAMPLE 50

N-(2,4-difluorophenyl)-N-(pyridin-3-ylmethyl)ethanesulfonamide

A 4.4 g. portion of 3-(2,4-difluorophenylaminomethyl)pyridine chloromethane, and 4.1 g. of potassium carbonate and 3.9 g. of ethanesulfonyl chloride were added. The mixture was stirred under reflux for several days. It was then diluted with 20 ml. of aqueous sodium bicarbonate and 20 ml. of dichloromethane, and the organic phase was dried and evaporated to an oil. The oil was dissolved in dichloromethane and chromatographed over silica gel, eluting with dichloromethane, to obtain 1.2 g. of the desired product, after triturating with diethyl ether and petroleum ether. M.P. 91°–92°.

Theory: C, 53.84; H, 4.52; N, 8.97;
Found: C, 53.81; H, 4.38; N, 8.92.

EXAMPLE 51

N-(2,4-difluorophenyl)-N-(pyridin-3-ylmethyl)(4-chlorobenzene)sulfonamide

A 4.4 g. portion of 3-(2,4-difluorophenylaminomethyl)pyridine was dissolved in 20 ml. of dichloromethane, and 4.1 g. of potassium carbonate and 6.3 g. of 4-chlorobenzenesulfonyl chloride were added. The mixture was stirred at ambient temperature for 4 days, and was then diluted with 20 ml. of dichloromethane and extracted with 25 ml. of aqueous sodium bicarbonate. The organic phase was dried and concentrated to an oil, which was dissolved in dichloromethane and applied to a silica gel column, eluting with dichloromethane and then with 9:1 dichloromethane:ethyl acetate. The product-containing fractions were combined and evaporated, and the residue was triturated with petroleum ether to obtain 3.1 g. of the desired product, m.p. 140°-143°.

Theory: C, 54.76; H, 3.32; N, 7.10;
Found: C, 54.89; H, 3.43; N, 6.99.

Preparation 3

3-(4-hydroxyphenylaminomethyl)pyridine

Five g. of 3-(4-hydroxyphenyliminomethyl)pyridine was prepared according to the process of Preparation 1, and was dissolved in 50 ml. of ethanol. One g. of palladium on carbon hydrogenation catalyst was added, and the mixture was agitated under 40 psig. hydrogen pressure for 1 hour. The catalyst was then removed by filtration, and the filtrate was evaporated to dryness. The residue consisted in large part of the desired intermediate product.

EXAMPLE 52

N-(4-hydroxyphenyl)-N-(pyridin-3-ylmethyl)methanesulfonamide

The residue from Preparation 3 was dissolved in 20 ml. of dichloromethane, and to it were added 10.5 g. of potassium carbonate and 5.8 ml. of methanesulfonyl chloride. The mixture was stirred at ambient temperature for 3 days, and was then stirred under reflux for 3 hours. It was cooled, diluted with 20 ml. of water and filtered. The solids were washed with water, and with diethyl ether, and dried to obtain 5.1 g. of N-(4-methanesulfonyloxyphenyl)-N-(pyridin-3-ylmethyl)methanesulfonamide. It was suspended in ethanol, heated and cooled, and filtered and dried to obtain 4.4 g. of the purified intermediate, m.p. 207°-210°.

The above product was suspended in 25 ml. of 4:1 acetone:ethanol and heated. It was then filtered, and the filtrate was evaporated under vacuum. The residue was triturated with diethyl ether, filtered and dried to obtain 2.7 g. of the desired compound, m.p. 208°-210°.

Theory: C, 56.10; H, 5.07; N, 10.06;
Found: C, 54.81; H, 4.80; N, 9.67.

EXAMPLE 53

N-(2,4-difluorophenyl)-N-[(pyridin-3-yl)(4fluorophenyl)methyl]-methanesulfonamide A 4.7 g. portion of N-[(4-fluorophenyl)(pyridin-3-yl)methyl]-2,4-difluoroaniline was dissolved in 15 ml. of dichloromethane and 2.8 g. of methanesulfonic anhydride was added. The mixture was stirred at ambient temperature for 1 day, and it was then extracted with aqueous sodium bicarbonate, and dried. It was then applied to a silica gel column and eluted with dichloromethane and then with 9:1 dichloromethane:ethyl acetate. The product-containing fractions were combined, evaporated under vacuum and crystallized to obtain 1.8 g. of the desired product.

Theory: C, 58.16; H, 3.85; N, 7.14;
Found: C, 58.14; H, 4.07; N, 6.90.

EXAMPLE 54

N-(4-methylphenyl)-N-(pyridin-3-ylmethyl)methanesulfonamide

A 3.5 g. portion of 3-(4-methylphenylaminomethyl)pyridine was dissolved in 15 ml. of dichloromethane, and 2.7 g. of potassium carbonate and 2 ml. of methanesulfonyl chloride were added. The mixture was stirred overnight under reflux, and was then extracted with 20 ml. of water and evaporated under vacuum. The residue was triturated with diethyl ether and dried to obtain 4.5 g. of the desired product, m.p. 143°-146°.

Theory: C, 60.85; H, 5.84; N, 10.14;
Found: C, 60.65; H, 5.54; N, 9.97.

EXAMPLE 55

N-(3-nitrophenyl)-N-(pyridin-3-ylmethyl)methanesulfonamide

A 3.2 g. portion of 3-(3-nitrophenylaminomethyl)pyridine was dissolved in 15 ml. of toluene, and 2.7 g. of potassium carbonate and 1.6 ml. of methanesulfonyl chloride were added. The mixture was heated to a gentle boil and stirred overnight under reflux. Twenty-five ml. of water and 25 ml. of ethyl acetate were added, and the organic phase was dried and evaporated under vacuum. The residue was triturated with diethyl ether, filtered and dried to obtain 2.4 g. of the desired product, m.p. 131°-133°.

Theory: C, 50.81; H, 4.26; N, 13.67;
Found: C, 51.01; H, 4.25; N, 13.43.

EXAMPLE 56

N-(2-fluorophenyl)-N-(pyridin-3-ylmethyl)methanesulfonamide

A 6 g. portion of 3-(2-fluorophenylaminomethyl)pyridine was dissolved in 50 ml. of acetone, and 5 g. of potassium carbonate and 5 g. of methanesulfonyl chloride were added. The mixture was stirred at ambient temperature overnight, and then under reflux for 6 hours. The mixture was cooled and filtered, and the filtrate was concentrated under vacuum to obtain 7.4 g. of an oil, which was chromatographed on silica gel, eluting with 1:4 acetone:toluene. Combination of the product-containing fractions and evaporation gave 9.7 g. of the desired product, m.p. 120°.

Theory: C, 55.70; H, 4.67; N, 9.99;
Found: C, 55.51; H, 4.44; N, 9.81.

EXAMPLE 57

N-phenyl-N-(pyridin-3-ylmethyl)-methanesulfonamide

A 3.7 g. portion of 3-(phenylaminomethyl)pyridine was dissolved in 20 ml. of dichloromethane, and to it was added 4.1 g. of potassium carbonate and 2.5 ml. of methanesulfonyl chloride. The mixture was stirred under reflux overnight, and was then diluted with 20 ml. of aqueous sodium bicarbonate and 20 ml. of dichloromethane. The organic phase was separated, washed with 20 ml. of water, dried over magnesium sulfate and evaporated under vacuum. The residue was triturated with diethyl ether and dried to give 4.9 g. of impure product. It was dissolved in 10 ml. of dichloromethane and 20 ml. of ethyl acetate and filtered. The filtrate was evaporated under vacuum, and the residue was triturated with petroleum ether, filtered and dried to obtain 4.4 g. of the desired product, m.p. 104°-105°.

Theory: C, 59.52; H, 5.38; N, 10.68;
Found: C, 59.31; H, 5.22; N, 10.43.

EXAMPLE 58

N-(2,4-dimethoxyphenyl)-N-(pyridin-3-ylmethyl)methanesulfonamide

A 7.3 g. portion of 3-(2,4-dimethoxyphenylaminomethyl)pyridine was dissolved in 25 ml. of dichloromethane, and 5.5 g. of potassium carbonate and 3.1 ml. of methanesulfonyl chloride were added. The mixture was stirred under reflux overnight. Then it was cooled, diluted with 25 ml. of dichloromethane and washed with 25 ml. of aqueous sodium bicarbonate. The organic layer was separated, washed with water, dried over magnesium sulfate and evaporated under vacuum. The residue was suspended in ethyl acetate, and filtered. The filtrate was evaporated, and the residue was triturated with diethyl ether, filtered and dried under vacuum to obtain 6.7 g. of the desired product, m.p. 117°–119°.

Theory: C, 55.89; H, 5.63; N, 8.69;
Found: C, 55.82; H, 5.63; N, 8.81.

EXAMPLE 59

N-(4-fluorophenyl)-N-(pyridin-3-ylmethyl)methanesulfonamide

A 2.3 g. portion of 3-(4-fluorophenylaminomethyl)pyridine was dissolved in 15 ml. of dichloromethane, and 2.1 g. of potassium carbonate and 1.2 ml. of methanesulfonyl chloride were added. The mixture was stirred under reflux for 2 days, and was then cooled and diluted with 20 ml. of aqueous sodium bicarbonate and 5 ml. of 2N sodium hydroxide. The organic phase was washed again with aqueous sodium bicarbonate, dried over magnesium sulfate and evaporated under vacuum. The residue was triturated with hot diethyl ether, and the solids were filtered and dried to obtain 2.6 g. of the desired product, m.p. 112°–113°.

Theory: C, 55.70; H, 4.67; N, 9.99;
Found: C, 55.47; H, 4.60; N, 9.94.

EXAMPLE 60

N-(2,4-dimethylphenyl)-N-(pyridin-3-ylmethyl)methanesulfonamide

A 4.2 g. portion of 3-(2,4-dimethylphenylaminomethyl)pyridine was dissolved in 20 ml. of dichloromethane and 4.1 g. of potassium carbonate and 2.5 ml. of methanesulfonyl chloride were added. The mixture was stirred over the week-end under reflux, and was then extracted with 20 ml. of aqueous sodium bicarbonate. The organic phase was dried and evaporated under vacuum. The residue was dissolved in diethyl ether and the solution was separated from insolubles and evaporated under vacuum. The oil was dissolved in chloroform and chromatographed over silica gel, eluting with chloroform:ethyl acetate to obtain 2.5 g. of the desired product, m.p. 62°–65°.

Theory: C, 62.04; H, 6.25; N, 9.65;
Found: C, 61.84; H, 6.05; N, 9.49.

EXAMPLE 61

N-(4-chlorophenyl)-N-[1-(pyridin-3-yl)ethyl](4-methylbenzene)sulfonamide

A 3.5 g. portion of 3-[1-(4-chlorophenylamino)ethyl]methane, and 2.7 g. of potassium carbonate and 3.8 g. of p-toluenesulfonyl chloride were added. The mixture was stirred overnight at ambient temperature, and then under reflux for 3 hours. After cooling, 20 ml. of water was added, and the organic layer was extracted with 20 ml. of aqueous sodium bicarbonate, dried over magnesium sulfate and evaporated under vacuum. The oily residue was dissolved in dichloromethane and chromatographed over silica gel, eluting first with dichloromethane and then with chloroform. Combination of the product-containing fractions and evaporation gave 1.47 g. of oil, which soon crystallized. The solids were triturated with petroleum ether to obtain 1.1 g. of the desired product, m.p. 101°–103°.

Theory: C, 62.09; H, 4.95; N, 7.24;
Found: C, 62.17; H, 4.76; N, 7.26.

EXAMPLE 62

N-(4-chloro-2-methoxyphenyl)-N-(pyridin-3-ylmethyl)methanesulfonamide

A 2.5 g. portion of 3-(4-chloro-2-methoxyphenylaminomethyl)pyridine was dissolved in 20 ml. of dichloromethane, and to it were added 2.1 g. of potassium carbonate and 1.2 ml. of methanesulfonyl chloride. The mixture was stirred with gentle heating for 2 days, and was then extracted with aqueous sodium bicarbonate. The organic phase was dried and evaporated under vacuum, and the residue was redissolved in dichloromethane and 2.6 g. of methanesulfonic anhydride was added. The mixture was stirred at ambient temperature for several days, and another 2.6 g. of the anhydride was added, together with 2.5 g. of additional starting amine. The mixture was stirred at ambient temperature for several days more, and was then diluted with 20 ml. of aqueous sodium bicarbonate and 15 ml. of dichloromethane, and the organic phase was dried over magnesium sulfate and evaporated to an oil. The oil was taken up in chloroform and chromatographed over silica gel, eluting with chloroform, to obtain 1.17 g. of the desired compound, m.p. 121°–123°.

Theory: C, 51.45; H, 4.63; N, 8.57;
Found: C, 51.72; H, 4.78; N, 8.43.

EXAMPLE 63

N-(4-chlorophenyl)-N-(phenyl)(pyridin-3yl)methyl]-(4-chlorobenzene)sulfonamide

A 2.8 g. portion of N-[(phenyl)(pyridin-3yl)methyl]-4-chloroaniline was dissolved in 15 ml. of dichloromethane, and to it were added 2.76 g. of potassium carbonate and 4.22 g. of 4-chlorobenzenesulfonyl chloride. The mixture was stirred for 2 days at about 40°. It was then diluted with 20 ml. of aqueous sodium bicarbonate, and the organic layer was separated, washed with water, dried and evaporated to an oil. The oil was taken up in dichloromethane, and an additional 2.7 g. of potassium carbonate and 4.2 g. of 4-chlorobenzenesulfonyl chloride were added. The mixture was stirred over the weekend under reflux, and was then worked up as above. The oil was taken up in chloroform and was chromatographed over silica gel, eluting with chloroform, to obtain a residue, which was triturated with petroleum ether to obtain 1.15 g. of the desired product, m.p. 98°–105°. That product was recrystallized from diethyl ether/petroleum ether to obtain 0.7 g. of purified product, m.p. 109°–112°.

Theory: C, 61.41; H, 3.87; N, 5.97;
Found: C, 61.62; H, 4.06; N, 5.84.

EXAMPLE 64

N-(2-chloro-4-methylphenyl)-N-(pyridin-3-ylmethyl)methanesulfonamide

A 3.5 g. portion of 3-(2-chloro-4-methylphenylaminomethyl)pyridine was dissolved in 15 ml. of dichloromethane, and 2.8 g. of potassium carbonate and 3.5 g. of methanesulfonic anhydride were added and the mixture stirred at ambient temperature for 3 days. Another 3.5 g. of methanesulfonic anhydride was added. The next day the mixture was diluted with 20 ml. of aqueous sodium bicarbonate and the organic phase was dried over magnesium sulfate and evaporated under vacuum to a residue, which was dissolved in dichloromethane. The solution was chromatographed over a silica gel column, eluting first with dichloromethane and then with chloroform. The product-containing fractions were combined and evaporated to obtain 3.1 g. of the desired product.

Theory: C, 54.10; H, 4.86; N, 9.01;
Found: C, 53.82; H, 4.86; N, 8.74.

EXAMPLE 65

N-(4-chlorophenyl)-N-[1-(pyridin-3-yl)ethyl]benzenesulfonamide

A 3.5 g. portion of 3-[1-(4-chlorophenylamino)ethyl]-pyridine was dissolved in dichloromethane, and 2.7 g. of potassium carbonate and 2.55 ml. of benzenesulfonyl chloride were added. The mixture was stirred at ambient temperature for 1 day, and was then diluted with 10 ml. of dichloromethane and extracted with 20 ml. of aqueous sodium bicarbonate and 20 ml. of water. The organic layer was dried over magnesium sulfate and evaporated under vacuum to an oil. The oil was dissolved in diethyl ether, and the insolubles were separated. The solvent was then evaporated away under vacuum, and the resulting oil was taken up in chloroform and chromatographed over a silica gel column, eluting with chloroform. The product-containing fractions were evaporated to obtain 3.1 g. of the desired product.

Theory: C, 61.20; H, 4.60; N, 7.51;
Found: C, 60.92; H, 4.53; N, 7.26.

Representative compounds of the present invention have been tested in standardized agricultural chemical test systems to determine the range of their efficacy. The following reports of tests are illustrative.

Test I

The test compounds were formulated for application by dissolving 48 mg. of a selected compound in 1.2 ml. of solvent. The solvent was prepared by mixing 100 ml. of Tween 20 (a nonionic surfactant) with 500 ml. of acetone and 500 ml. of ethanol. The solvent/compound solution was finally diluted to 120 ml. with deionized water.

The formulated test compounds were applied by both soil drench and foliar methods. In the foliar spray application method, the following plant pathogens and their corresponding host plants were employed:

*Erysiphe graminis tritici* (powdery mildew) on dry bean
*Colletotrichum lagenarium* (anthracnose) on cucumber
*Pyricularia oryzae* (rice blast) on rice
*Botrytis cinerea* (gray mould) on grape *berry*
*Helminthosporium sativum* (leaf spot) on wheat
*Puccinia recondita tritici* (leaf rust) on wheat

*Phytophthora infestans* (late blight) on tomato

The foliar applications were made at a parts per million (ppm.) test compound concentration by either of two methods. In the Botrytis test, the formulated compound was sprayed onto the berries with a small atomizer at approximately 8 pounds per square inch (psi). In the remaining tests, the formulated test compounds were sprayed by hand in a fume hood. Single pots of plants were placed on raised, revolving pedestals in the hood. Using a spray gun, all test solutions were applied by hand at 40 psi. As the spray was delivered, the pedestals were rotated to expose all plant surfaces to the spray pattern and the spray was applied to the run-off point. All treatments were allowed to dry and the host plants were inoculated with the pathogens 24 hours later.

In the soil drench application method, the following plant pathogens and host plants were employed:

*Xanthomonas oryzae* (bacterial leaf blight) on rice
Maize dwarf mosaic virus on corn *Rhizoctonia solani* (damping-off) on cotton
*Meloidogyne incognito* (root knot nematode) on cucumber The soil drench application was made by removing 10 ml. of the prepared formulation and uniformly syringing it over the surface of each pot, containing 14-day-old rice plants, 10-day-old corn, 10-day-old cucumber, or newly seeded cotton. The pot size at soil surface was 2.5 inches in diameter. Thus, the application of 10 ml. of a 400 ppm. solution equaled an 11 pounds per acre (lb./A.) broadcast dosage or 12.3 kilograms per hectare (kg./ha.). The Rhizoctonia test was conducted in a smaller pot and 20 ml. of the formulation was applied. Thus, this dosage equaled 35 lb./A. (39.2 kg./ha.). The rice and corn plants were inoculated 24 hours after treatment; the cotton and cucumber plants were inoculated the same day as treatment.

The effectiveness of test compounds in controlling the foregoing plant diseases was rated on a scale of 1 to 5. On this scale "1" indicates severe disease (or no control), "2" is moderate disease, "3" is slight disease, "4" is very slight disease, and "5" indicates no disease or 100% control. A "+" symbol indicates a slightly higher rating. Also a phytotoxicity rating was recorded, where phytotoxicity was present, using a scale from 1 to 5 with 1 indicating no toxicity and 5 indicating death to the plant. Finally, when phytotoxicity was present, a letter rating was given to the plant indicating the type of injury caused to the plant. These injuries were coded as follows:

G=General necrosis
W=Wilting
S=Stunting
C=Chlorosis
F=Formative

Table I presents the activity of typical compounds of the present invention when evaluated in the foliar and soil drench application methods described above.

TABLE I

| | FOLIAR APPLICATION | | | | | | | SOIL APPLICATION | | | |
|---|---|---|---|---|---|---|---|---|---|---|---|
| EX. NO. | POWD MDEW | ANTH NOSE | RICE BLAS | BOTR YTIS | HELM SPOR | LEAF RUST | LATE BLIT | BACT BLIT | MAZE DWRF | RHIZ TONA | ROOT KNOT |
| 1 | 4 | 43G | 1 | 1 | 1 | 1 | | 1 | 1 | 1 | 1 |
| 3 | 5 | 1 | 1 | 1 | 4 | 1 | 1 | 1 | 1 | 5 | 1 |
| 4 | 5 | 4 | 1 | 1 | 4 | 1 | 1 | 1 | 1 | 4 | 1 |
| 5 | 5 | 3 | 1 | 1 | 4 | 3 | | 1 | 1 | 1 | 13S |
| 6 | 5 | 1 | 1 | 1 | 4 | 1 | 1 | 1 | 1 | 4 | 1 |
| 7 | 1 | 4 | 1 | 1 | 1 | 1 | | 1 | 1 | 1 | 1 |

TABLE I-continued

| EX. NO. | FOLIAR APPLICATION | | | | | | | SOIL APPLICATION | | | |
|---|---|---|---|---|---|---|---|---|---|---|---|
| | POWD MDEW | ANTH NOSE | RICE BLAS | BOTR YTIS | HELM SPOR | LEAF RUST | LATE BLIT | BACT BLIT | MAZE DWRF | RHIZ TONA | ROOT KNOT |
| 8 | 52G | 1 | 1 | 1 | 4 | 1 | 1 | 1 | 1 | 3 | 1 |
| 9 | 5 | 1 | 1 | 1 | 1 | 1 | 1 | 1 | 1 | 4 | 1 |
| 10 | 1 | 1 | 1 | 1 | 1 | 1 | 1 | 1 | 1 | 4 | 1 |
| 11 | 1 | 1 | 1 | 1 | 4 | 1 | 1 | 1 | 12S | 1 | 1 |
| 12 | 4 | −5 | 1 | 1 | 4 | 4 | 1 | 1 | 1 | 4 | 1 |
| 13 | 4 | 1 | 1 | 1 | 1 | 4 | 1 | 1 | 1 | 1 | 13G |
| 14 | 42F | 1 | 1 | 1 | 4 | 1 | 1 | 1 | 1 | 3 | 1 |
| 15 | 5 | | 1 | 1 | 4+ | 1 | 1 | | | 1 | 1 |
| 17 | 4 | 1 | 1 | 1 | 5 | 4 | 1 | 1 | 1 | 3 | 1 |

Test II

Compounds tested in this plant disease foliage test were formulated in the same manner as described above for Test I. A 400 ppm. concentration was serially diluted with water containing 0.05% Tween 20 (a nonionic surfactant) to obtain formulations having lower concentrations of test compound. The plants were treated and inoculated in the same manner as described above for foliar application. The pathogens and their corresponding host plants in this experiment were as follows:

*Erysiphe graminis tritici* (powdery mildew) on dry bean
*Phytophthora infestans* (late blight) on tomato
*Venturia inaequalis* (scab) on apple
*Colletotrichum lagenarium* (anthracnose) on cucumber
*Pyricularia oryzae* (rice blast) on rice Plasmopara viticola (downy mildew) on grape
*Cercospora beticola* (leaf spot) on sugar beet After a suitable incubation period, when disease symptoms appeared on untreated control plants, treatments were rated for disease severity according to the rating system described above. The results are recorded in Table II.

TABLE II

| EX. NO. | PPM | BEAN MDEW | LATE BLIT | APPL SCAB | ANTH NOSE | RICE BLAS | GRAP MDEW | CERC SPOR |
|---|---|---|---|---|---|---|---|---|
| 3 | 400 | 5 | | 52G | 3 | | | 5 |
| | 400 | 5 | 1 | 52G | 4 | 1 | 1 | 5 |
| | 100 | 3 | | | | | | 5 |
| | 100 | 5 | | 3 | 1 | | | 5 |
| | 25 | 1 | | | | | | 4 |
| | 25 | 5 | | 1 | 1 | | | 4 |
| | 6 | 1 | | | | | | 1 |
| 4 | 400 | 1 | 4 | 3 | 13G | 1 | 4 | 5 |
| | 400 | 5 | 3 | | | | 4 | 5 |
| | 100 | 4 | 1 | | | | 4 | 4 |
| | 100 | 5 | | | | | 1 | 4 |
| | 25 | 4 | | | | | 1 | 1 |
| | 25 | 4 | 1 | | | | 1 | 1 |
| | 6 | 3 | | | | | 1 | 1 |
| 5 | 400 | 5 | | | | | | 5 |
| | 400 | 5 | 1 | 1 | 1 | 1 | 1 | 5 |
| | 400 | 5 | 1 | 5 | 3 | 1 | 1 | 4 |
| | 400 | 52G | | 4 | | | | 3 |
| | 100 | 5 | | | | | | 4 |
| | 100 | 5 | | | | | | 5 |
| | 100 | 52F | | | | | | |
| | 100 | 52G | | 3 | | | | 4 |
| | 25 | 4 | | | | | | 4 |
| | 25 | 4 | | | | | | |
| | 25 | 5 | | 3 | | | | 1 |
| | 6 | 1 | | | | | | 4 |
| | 6 | 1 | | | | | | |
| 6 | 400 | 5 | | 5 | | | | 4 |
| | 400 | 5 | 1 | | 1 | 1 | 3 | 4 |
| | 100 | 5 | | 4 | | | | |
| | 100 | 5 | | 5 | | | | 3 |
| | 25 | 5 | | 4 | | | | |
| | 25 | 5 | | 5 | | | | 1 |
| | 6 | 5 | | 4 | | | | |
| 8 | 400 | 5 | | 52G | | | | |
| | 400 | 5 | 1 | 52G | 1 | 1 | 1 | 1 |
| | 100 | 5 | | | | | | |
| | 100 | 5 | | 1 | | | | |
| 8 | 25 | 5 | | | | | | |
| | 25 | 5 | | 1 | | | | |
| | 6 | 3 | | | | | | |
| 9 | 400 | 5 | 1 | 5 | | | | |
| | 400 | 52C | 4 | 5 | 1 | 1 | 1 | 3 |
| | 100 | 5 | | 5 | | | | |
| | 100 | 5 | 1 | 5 | | | | |
| | 25 | 4 | | 4 | | | | |

TABLE II-continued

| EX. NO. | PPM | BEAN MDEW | LATE BLIT | APPL SCAB | ANTH NOSE | RICE BLAS | GRAP MDEW | CERC SPOR |
|---|---|---|---|---|---|---|---|---|
| | 25 | 5 | 1 | 4 | | | | |
| | 6 | 1 | | 1 | | | | |
| 11 | 400 | 3 | | | | | | |
| | 400 | 4 | 1 | 1 | 1 | 1 | 1 | 1 |
| | 100 | 1 | | | | | | |
| | 25 | 1 | | | | | | |
| 12 | 400 | 4 | | | | | | 3 |
| | 400 | 4 | 1 | 3 | −5 | 1 | 3 | 4 |
| | 100 | 3 | | | | | | 1 |
| | 25 | 1 | | | | | | 1 |
| 15 | 100 | | | | | | | 4 |
| | 25 | | | | | | | 3 |
| | 6 | | | | | | | 1 |
| | 400 | 5 | | 4 | | | | 4 |
| | 400 | 5 | 1 | 5 | 1 | 1 | 1 | 4 |
| | 100 | 3 | | 1 | | | | 4 |
| | 25 | 1 | | 1 | | | | 4 |
| 17 | 400 | 5 | | | | | | 3 |
| | 400 | 5 | 1 | 3 | 1 | 1 | 1 | 4 |
| | 100 | 4 | | | | | | 3 |
| | 100 | 5 | | | | | | |
| | 25 | 3 | | | | | | 1 |
| | 25 | 4 | | | | | | |
| | 6 | 3 | | | | | | |

Test III

Certain compounds provided by this invention were further tested for control of various cereal grain diseases. The compounds tested were formulated as described above and applied by both foliar spray and soil drench methods. The soil drench applications provided a type of systemic control evaluation. The soil drench was applied by syringing 10 ml. of test formulation uniformly over the soil surface of a pot containing 6-day-old wheat plants, providing a treatment rate of 11 lb./acre, when 400 ppm formulations were used. Lower concentrations were also used as indicated in the table. Both foliar and drench treated plants were inoculated 24 hours after treatment. The diseases and host plants employed in this test were as follows:

Erysiphe graminis tritici (powdery mildew)
Puccinia recondita (leaf rust)
Helminthosporium sativum (leaf spot)
Septoria tritici (leaf blotch)

After a suitable incubation period when disease symptoms had appeared on untreated plants, the treated plants were rated for disease severity. The results of the foliar and soil drench tests appear in Table III.

TABLE III

| | | FOLIAR APPLICATION | | | | SOIL APPLICATION | | | |
|---|---|---|---|---|---|---|---|---|---|
| EX. NO. | PPM | WHET MDEW | LEAF RUST | HELM SPOR | SEPT ORIA | POWD MDEW | LEAF RUST | HELM SPOR | SEPT ORIA |
| 1 | 400 | 1 | 1 | 1 | 1 | 1 | 1 | 1 | 1 |
| 3 | 400 | 3 | | 4 | 53S | 53S | | | 53S |
| | 400 | 42G | 1 | 5 | 53S | 52S | 32S | 1 | 53S |
| | 100 | 1 | | 3 | 53S | 52S | | | 5 |
| | 25 | 1 | | 1 | 1 | 5 | | | 1 |
| 4 | 400 | 42G | 3 | 3 | 4 | 1 | | 1 | 4 |
| | 400 | 42G | 4 | 5 | 4 | 5 | 1 | 5 | 5 |
| | 100 | 4 | 3 | 1 | 4 | 1 | | 1 | 1 |
| | 25 | 3 | 1 | 1 | 1 | 1 | | 1 | 1 |
| 5 | 400 | | 1 | 4 | | | 33S | | 42S |
| | 100 | | 1 | 1 | | | 12S | | 42S |
| | 25 | | 1 | 1 | | | 1 | | 1 |
| | 400 | 1 | | | | 52C | | | |
| | 400 | 4 | 4 | 4 | 1 | 52S | 33S | 1 | 43S |
| | 100 | 1 | | | | 1 | | | |
| | 25 | 1 | | | | 1 | | | |
| 6 | 100 | | | | 4 | | | | |
| | 25 | | | | 3 | | | | |
| | 6 | | | 1 | 1 | | | | |
| | 400 | 4 | 3 | 5 | 4 | 1 | 1 | 1 | 1 |
| | 400 | 53G | 3 | 5 | 5 | | | | |
| | 100 | 1 | 1 | 4 | 5 | | | | |
| | 25 | 1 | 1 | 1 | 5 | | | | |
| 7 | 400 | 1 | 1 | 1 | 1 | 1 | 1 | 1 | 1 |
| 8 | 400 | | | 5 | 5 | | | | 1 |
| | 100 | | | 1 | 5 | | | | |
| | 100 | | | 4 | 5 | | | | 1 |
| | 25 | | | 1 | 4 | | | | |
| | 25 | | | 1 | 4 | | | | 1 |
| | 6 | | | 1 | 4 | | | | |
| | 400 | 1 | 1 | 4 | 4 | 3 | 1 | 1 | 42S |
| 11 | 400 | | | 5 | 4 | | | | |
| | 100 | | | 3 | | | | | |

TABLE III-continued

| EX. NO. | PPM | FOLIAR APPLICATION | | | | SOIL APPLICATION | | | |
|---|---|---|---|---|---|---|---|---|---|
| | | WHET MDEW | LEAF RUST | HELM SPOR | SEPT ORIA | POWD MDEW | LEAF RUST | HELM SPOR | SEPT ORIA |
| | 100 | | | 4 | 1 | | | | |
| | 25 | | | | 1 | | | | |
| | 25 | | | 3 | 1 | | | | |
| | 6 | | | | 1 | | | | |
| | 400 | 1 | 1 | 4 | 4 | 1 | 1 | 1 | 1 |
| 12 | 400 | 42G | 4 | 4 | 5 | 3 | 1 | 1 | 1 |
| | 400 | 42G | 42G | 5 | 5 | 1 | | | |
| | 100 | 1 | | 4 | 5 | | | | |
| | 100 | 4 | 1 | 4 | 5 | 1 | | | |
| | 25 | 1 | | 1 | 4 | | | | |
| | 25 | 3 | 1 | 1 | 4 | 1 | | | |
| | 6 | 1 | | 1 | 3 | | | | |
| 13 | 400 | 5 | 4 | 5 | 5 | 52G | 42G | 4 | 52G |
| | 400 | 52G | 4 | 5 | 5 | 52G | 53S | 12S | 53S |
| | 100 | 4 | | 3 | 4 | 42S | 42C | | 52S |
| | 100 | 5 | 1 | 4 | 4 | 52G | 52S | 12S | 52S |
| | 25 | 4 | | 1 | 1 | 3 | 3 | | 5 |
| | 25 | 5 | 1 | 4 | 1 | 5 | 5 | 1 | 42G |
| | 6 | 3 | | 1 | 1 | 1 | 1 | | 4 |
| 14 | 100 | | | 1 | 4 | 42S | | | 1 |
| | 25 | | | 1 | 1 | 32S | | | 1 |
| | 6 | | | 1 | 1 | 1 | | | 1 |
| | 400 | 32G | | 5 | 5 | 52S | | | 4 |
| | 400 | 32G | 3 | 5 | 4 | 52G | 3 | 1 | 4 |
| | 100 | 1 | | 4 | 5 | 52S | | | 4 |
| | 25 | 1 | | 3 | 4 | 42S | | | 1 |
| 15 | 100 | | | | 1 | | | | |
| | 25 | | | | 1 | | | | |
| | 6 | | | | 1 | | | | |
| | 400 | | | 52G | 4 | | | | 52C |
| | 100 | | | 4 | 5 | | | | 52C |

Test IV

Certain compounds of this invention also have been evaluated in soil drench tests to demonstrate their antifungal activity. Test compounds were formulated by dissolving 57 mg. of compound in 1 ml. of a fifty percent volume per volume (v/v) solution of acetone and ethanol. A 0.1 percent aqueous solution of Tween 20 was added to bring the final volume to 16 ml.

Pathogen-infested soil was placed in 8-ounce paper cups. A depression was made in the surface of the soil and 3 g. of Celatom MP-78 absorbent granules was placed in the depression. A 4 ml. aliquot of compound formulation, equivalent to a rate of 40 lb./A. (44.8 kg./ha.), was added to the granules and the cups were then covered with lids. The containers were shaken by hand for about 10 seconds and then placed on a roller about 10 minutes to thoroughly incorporate the test compound into the soil. After the treated soil was transferred to a 2.5-inch round plastic pot, seeds of the host plant were added and covered with additional treated soil. The pathogens and their host plants were as follows:

Rhizoctonia solani (damping-off) on cotton
Pythium aphanodermatum (damping-off) on cotton
Fusarium solani phaseoli (root rot) on dry bean
Verticillium albo-atrum (wilt) on cotton When disease symptoms had appeared on untreated control plants, the effect of the test compounds was observed on the treated plants and was rated on the scale of 1 to 5. The results of these evaluations are presented in Table IV.

TABLE IV

| EX. NO. | LB/A | SOIL DISEASES | | | |
|---|---|---|---|---|---|
| | | RHIZOCTONIA | PYTHIUM | FUSARIUM | VERTICILLIUM |
| 3 | 40 | 4 | | 4 | 1 |
| | 40 | 4 | | 4 | 1 |
| | 40 | 5 | 1 | 5 | 5 |
| | 10 | 4 | | 4 | |
| | 10 | 4 | | 4 | 1 |
| | 5 | 1 | | 4 | |
| | 2.5 | 1 | | 4 | |
| 4 | 40 | 4 | 3 | 5 | 1 |
| | 40 | 5 | | | |
| | 20 | 5 | | | |
| | 10 | 4 | | | |
| 5 | 40 | 4 | | | |
| | 40 | 4 | | | |
| | 40 | 4 | 1 | 1 | 1 |
| | 20 | 3 | | | |
| | 20 | 3 | | | |
| | 10 | 3 | | | |
| | 10 | 3 | | | |
| 8 | 40 | 4 | | | |
| | 40 | 4 | 1 | 1 | 1 |
| | 20 | 4 | | | |

TABLE IV-continued

| EX. NO. | LB/A | SOIL DISEASES | | | |
|---|---|---|---|---|---|
| | | RHIZOCTONIA | PYTHIUM | FUSARIUM | VERTICILLIUM |
| | 10 | 4 | | | |
| | 5 | 5 | | | |
| | 2.5 | 5 | | | |
| 9 | 40 | 4 | | | |
| | 40 | 4 | 1 | 1 | 1 |
| | 20 | 5 | | | |
| | 10 | 3 | | | |
| | 10 | 4 | | | |
| | 5 | 4 | | | |
| | 2.5 | 3 | | | |
| 10 | 40 | 4 | 4 | 5 | 1 |
| | 40 | 5 | 1 | | |
| | 20 | 3 | 1 | | |
| | 10 | 1 | | | |
| | 10 | 5 | 1 | | |
| | 5 | 1 | | | |

TEXT V

Certain compounds were applied by foliar spray, after they were formulated as described above. The diseases and host plants employed in this test were as follows:

*Erysiphe graminis tritici* (powdery mildew) on wheat
*Pyricularia oryzae* (rice blast) on rice
*Puccinia recondita tritici* (leaf rust) on wheat
*Botrytis cinerea* (gray mold) on grape berry
*Pseudoperonospora cubensis* (downy mildew) on squash
*Venturia inaequalis* (scab) on apple
*Septoria tritici* (leaf blotch) on wheat
*Cercospora beticola* (leaf spot) on sugar beet The effectiveness of the test compounds was rated on a scale of 1 to 9:

| 1 | 0–19% control |
|---|---|
| 2 | 20–29% |
| 3 | 30–39% |
| 4 | 40–59% |
| 5 | 60–74% |
| 6 | 75–89% |
| 7 | 90–96% |
| 8 | 97–99% |
| 9 | 100% control, no disease |

Phytotoxicity was recorded on a 1–5 scale, as described above.

TABLE V

| EX. NO. | PPM | FOLIAR DISEASES | | | | | | | |
|---|---|---|---|---|---|---|---|---|---|
| | | WHET MDEW | RICE BLAS | LEAF RUST | BOTR YTIS | SQUA MDEW | APPL SCAB | SEPT ORIA | CERC BEET |
| 6 | 400 | 92C | | 82C | 9 | | | | |
| | 100 | 8 | | 7 | 2 | | 52G | 8 | |
| | 100 | 8 | | 6 | | | | 8 | |
| | 25 | 7 | | 5 | | | | 7 | |
| | 6.25 | 5 | | 5 | | | | 2 | |
| | 400 | 92G | 4 | 82G | 8 | 1 | | | |
| | 25 | 7 | | 5 | 1 | | | | |
| 16 | 400 | 93G | | | | | | | |
| | 100 | 92G | | | | | 5 | 7 | |
| | 100 | 72G | | | | | | 7 | |
| | 25 | 5 | | | | | | 1 | |
| | 6.25 | 2 | | | | | | 1 | |
| | 400 | 72G | 1 | 62C | 1 | 1 | | | |
| | 25 | 6 | | | | | | | |
| 18 | 400 | 82C | | | | | | | |
| | 100 | 8 | | | | | 1 | 4 | |
| | 100 | 62G | | | | | | | |
| | 25 | 4 | | | | | | | |
| | 6.25 | 1 | | | | | | | |
| | 400 | 72G | 1 | 1 | 1 | 1 | | | |
| | 25 | 6 | | | | | | | |
| 19 | 400 | 5 | 1 | 1 | 1 | 1 | | | |
| 20 | 400 | 92G | | | 9 | | | | |
| | 100 | 6 | | | 9 | | 2 | 5 | |
| | 400 | 82G | 1 | 42G | 9 | 1 | | | |
| | 25 | 2 | | | 1 | | | | |
| 21 | 400 | 62G | | | | | | | |
| | 100 | 22C | | | | | 1 | 12G | |
| | 25 | 1 | | | | | | | |
| | 400 | 72G | 1 | 1 | 1 | 1 | | | |
| 22 | 400 | | | 6 | | 9 | | | |
| 22 | 100 | | | 2 | | 2 | 1 | 1 | |
| | 25 | | | 1 | | 1 | | | |
| | 400 | 5 | 1 | 7 | 1 | 9 | | | |
| 23 | 400 | 92G | | | | | | | |
| | 100 | 82S | | | | | 4 | | |
| | 100 | 82G | | | | | 8 | 5 | |

TABLE V-continued

| | | FOLIAR DISEASES | | | | | | | |
|---|---|---|---|---|---|---|---|---|---|
| EX. NO. | PPM | WHET MDEW | RICE BLAS | LEAF RUST | BOTR YTIS | SQUA MDEW | APPL SCAB | SEPT ORIA | CERC BEET |
| | 25 | 6 | | | | | 2 | | |
| | 6.25 | 2 | | | | | 1 | | |
| | 400 | 82G | 1 | 4 | 1 | 1 | | | |
| | 25 | 6 | | | | | | | |
| 24 | 400 | 5 | 1 | 1 | 1 | 1 | | | |
| 25 | 400 | 92C | | 82G | | | | | |
| | 100 | 8 | | 82G | | | 82G | 9 | |
| | 100 | 72C | | 3 | | | 82G | 7 | |
| | 100 | 1 | | 1 | | | 1 | 1 | |
| | 25 | 6 | | 1 | | | 3 | 5 | |
| | 25 | 1 | | 1 | | | 1 | 1 | |
| | 6.25 | 2 | | 1 | | | 1 | 3 | |
| | 6.25 | 1 | | 1 | | | 1 | 1 | |
| | 400 | 82C | 1 | 72G | 1 | 1 | | | |
| | 25 | 7 | | 4 | | | | | |
| 26 | 400 | 72G | | | | | | | |
| | 100 | 62G | | | | | 3 | 8 | |
| | 100 | | | | | | | 6 | |
| | 25 | | | | | | | 2 | |
| | 6.25 | | | | | | | 1 | |
| | 25 | 4 | | | | | | | |
| | 400 | 7 | 1 | 1 | 1 | 1 | | | |
| 27 | 400 | 8 | | | | | | | |
| | 100 | 82G | | | | | | | |
| | 100 | 7 | | | | | 1 | 1 | |
| | 25 | 5 | | | | | | | |
| | 6.25 | 3 | | | | | | | |
| | 400 | 8 | 3 | 2 | 1 | 1 | | | |
| | 25 | 5 | | | | | | | |
| 28 | 400 | 32G | 1 | 12C | 1 | 1 | | | |
| 29 | 400 | 92G | | | | | | | |
| | 100 | 92G | | | | | | 6 | |
| | 100 | 8 | | | | | 5 | 7 | |
| | 25 | 7 | | | | | | 3 | |
| | 25 | 6 | | | | | | 6 | |
| | 6.25 | 3 | | | | | | 4 | |
| | 1.56 | 2 | | | | | | 1 | |
| | 400 | 92G | 1 | 42G | 1 | 1 | | | |
| | 25.00 | 8 | | | | | | | |
| | 6.25 | 2 | | | | | | 1 | |
| 30 | 400 | 62G | | | | | | | |
| | 100 | 2 | | | | | 1 | 1 | |
| | 25 | 1 | | | | | | | |
| | 400 | 72G | 1 | 1 | 1 | 1 | | | |
| 31 | 400 | 92G | | 82G | | | | | |
| | 100 | 92G | | | | | | 5 | |
| | 100 | 9 | | 6 | | | 6 | 7 | |
| | 25 | 7 | | | | | | 3 | |
| | 6.25 | 3 | | | | | | 1 | |
| | 400 | 92G | 1 | 72C | 1 | 1 | | | |
| | 25 | 7 | | 1 | | | | | |
| 32 | 400 | 1 | 6 | 12G | 1 | −5 | | | |
| 33 | 400 | | | | | 4 | | | |
| | 100 | | | | | 2 | 1 | 7 | |
| | 100 | | | | | | | 4 | |
| | 25 | | | | | | | 1 | |
| | 6.25 | | | | | | | 1 | |
| | 400 | 5 | 1 | 1 | 1 | 8 | | | |
| | 25 | | | | | 1 | | | |
| 34 | 400 | | | | | 32G | | | |
| | 100 | | | | | 1 | 1 | 5 | |
| | 25 | | | | | 1 | | | |
| 34 | 400 | 12C | 3 | 1 | 1 | 92G | | | |
| 36 | 400 | 93C | | 92C | | | | | |
| | 100 | 82G | | 8 | | | 52G | 6 | |
| | 25 | 6 | | 2 | | | | | |
| | 400 | 92G | 1 | 6 | 1 | 62G | | | |
| 37 | 400 | 8 | | | | | | | |
| | 100 | 7 | | | | | 1 | 1 | |
| | 25 | 6 | | | | | | | |
| | 400 | 7 | 1 | 1 | 1 | 1 | | | |
| 38 | 400 | 82G | | | | | | | |
| | 100 | 7 | | | | | 1 | 4 | |
| | 25 | 5 | | | | | | | |
| | 400 | 72G | 1 | 5 | 1 | 1 | | | |
| 39 | 400 | 92G | | | | | | | |
| | 100 | 6 | | | | | 1 | 7 | |
| | 100 | | | | | | | 4 | |
| | 25 | | | | | | | 3 | |

TABLE V-continued

| | | FOLIAR DISEASES | | | | | | | |
|---|---|---|---|---|---|---|---|---|---|
| EX. NO. | PPM | WHET MDEW | RICE BLAS | LEAF RUST | BOTR YTIS | SQUA MDEW | APPL SCAB | SEPT ORIA | CERC BEET |
| | 6.25 | | | | | | | 2 | |
| | 400 | 72G | 1 | 1 | 1 | 1 | | | |
| | 25 | 4 | | | | | | | |
| 40 | 400 | 82G | | 7 | | | | | |
| | 100 | 7 | | 4 | | | 1 | 6 | |
| | 25 | 5 | | 2 | | | | | |
| | 400 | 8 | 1 | 7 | 1 | 13G | | | |
| 41 | 400 | 8 | | | | | | | |
| | 100 | 7 | | | | | 1 | 4 | |
| | 25 | 4 | | | | | | | |
| | 400 | 7 | 1 | 1 | 1 | 1 | | | |
| 42 | 400 | 1 | 1 | 5 | 1 | | | | |
| 43 | 400 | 92G | | 82C | | | | | |
| | 100 | 92G | | 6 | | | 72G | 8 | |
| | 100 | 92G | | | | | 82G | 92C | |
| 43 | 25 | 8 | | | | | 5 | 82C | |
| | 6.25 | 7 | | | | | 3 | 4 | |
| | 400 | 92G | 1 | 82G | 1 | 1 | | | |
| | 25 | 8 | | 1 | | | | | |
| 44 | 400 | 92G | | 72G | 6 | | | | |
| | 100 | 83G | | | | | 62G | 82G | |
| | 100 | 72C | | 62G | 1 | | 72G | 8 | |
| | 25 | 72G | | | | | 52G | 8 | |
| | 6.25 | 7 | | | | | 4 | 7 | |
| | 400 | 82G | 1 | 82G | 7 | 1 | | | |
| | 25 | 7 | | 2 | 1 | | | | |
| 45 | 400 | 72G | | | | | | | |
| | 100 | 6 | | | | | 1 | 1 | |
| | 25 | 3 | | | | | | | |
| | 400 | 82G | 1 | 1 | 1 | 1 | | | |
| 46 | 400 | 62G | | | | | | | |
| | 100 | 2 | | | | | 5 | 4 | |
| | 25 | 1 | | | | | | | |
| | 400 | 72G | 1 | 1 | 1 | 1 | | | |
| 47 | 400 | 93G | | 82G | | | | | |
| | 100 | 92G | | 5 | | | 52G | 8 | |
| | 100 | 82G | | | | | | 8 | |
| | 25 | 7 | | | | | | 7 | |
| | 6.25 | 5 | | | | | | 4 | |
| | 400 | 83G | 4 | 73G | 1 | 1 | | | |
| | 25 | 8 | 2 | | | | | | |
| 48 | 400 | 62G | 1 | 1 | 1 | 1 | | | |
| 49 | 400 | 52G | | | | | | | |
| | 100 | 2 | | | | | 1 | 1 | |
| | 25 | 1 | | | | | | | |
| | 400 | 72G | 1 | 5 | 1 | 1 | | | |
| 50 | 400 | 92G | | 72G | | | | | |
| | 100 | 9 | | 5 | | | 7 | 8 | |
| | 100 | 9 | | | | | 72G | 8 | |
| | 25 | 7 | | | | | 4 | 5 | |
| 50 | 6.25 | 4 | | | | | 1 | 1 | |
| | 400 | 82G | 1 | 72C | 1 | 1 | | | |
| | 25 | 7 | | 2 | | | | | |
| 51 | 400 | 1 | 1 | 1 | 1 | 1 | | | |
| 52 | 400 | 7 | 1 | 1 | 1 | 1 | | | |
| | 25 | 2 | | | | | | | |
| | 100 | 5 | | | | | 1 | 1 | |
| | 400 | 7 | | | | | | | |
| 53 | 400 | 8 | 5 | 5 | 1 | 1 | | | |
| | 25 | 6 | | | | | | | |
| | 100 | 7 | | | | | 1 | 7 | |
| | 400 | 9 | | | | | | | |
| | 6.25 | 5 | | | | | | 4 | |
| | 25 | 6 | | | | | | 5 | |
| | 100 | 8 | | | | | | 82G | |
| 54 | 400 | 82G | 1 | 1 | 1 | 1 | | | |
| | 25 | 6 | | | | | | | |
| | 100 | 7 | | | | | 1 | 7 | |
| | 400 | 8 | | | | | | | |
| | 6.25 | 3 | | | | | | 1 | |
| | 25 | 5 | | | | | | 3 | |
| | 100 | 7 | | | | | | 42G | |
| 55 | 400 | 6 | 1 | 1 | 1 | 1 | | | |
| 56 | 400 | 82G | 1 | 5 | 1 | 1 | | | |
| | 25 | 7 | | | | | | | |
| | 100 | 82G | | | | | 5 | 7 | |
| | 400 | 92G | | | | | | | |
| | 6.25 | 4 | | | | | | 1 | |
| | 25 | 7 | | | | | | 1 | |

TABLE V-continued

| EX. NO. | PPM | WHET MDEW | RICE BLAS | LEAF RUST | BOTR YTIS | SQUA MDEW | APPL SCAB | SEPT ORIA | CERC BEET |
|---|---|---|---|---|---|---|---|---|---|
|  | 100 | 82G |  |  |  |  |  | 6 |  |
| 57 | 400 | 72G | 1 | 1 | 1 | 1 |  |  |  |
|  | 25 | 5 |  |  |  |  |  |  |  |
|  | 100 | 72G |  |  |  |  | 1 | 5 |  |
|  | 400 | 82G |  |  |  |  |  |  |  |
|  | 6.25 | 2 |  |  |  |  |  |  |  |
|  | 25 | 5 |  |  |  |  |  |  |  |
|  | 100 | 72G |  |  |  |  |  |  |  |
| 58 | 400 | 72G | 1 | 12G | 1 | 1 |  |  |  |
|  | 25 | 1 |  |  |  |  |  |  |  |
|  | 100 | 4 |  |  |  |  | 1 | 1 |  |
|  | 400 | 82G |  |  |  |  |  |  |  |
| 59 | 400 | 92G | 1 | 62G | 1 | 12C |  |  |  |
|  | 25 | 8 |  |  |  |  |  |  |  |
|  | 100 | 82G |  |  |  |  | 7 | 7 |  |
|  | 400 | 92G |  |  |  |  |  |  |  |
|  | 6.25 | 7 |  |  |  |  | 1 | 1 |  |
|  | 25 | 8 |  |  |  |  | 3 | 7 |  |
|  | 100 | 92G |  |  |  |  | 6 | 8 |  |
|  | 1.56 | 1 |  |  |  |  | 1 | 1 |  |
|  | 6.25 | 2 |  |  |  |  | 2 | 1 |  |
|  | 25 | 6 |  |  |  |  | 5 | 3 |  |
| 60 | 400 | 92G | 1 | 12C | 1 | 1 |  |  |  |
|  | 25 | 7 |  |  |  |  |  |  |  |
|  | 100 | 82G |  |  |  |  | 7 | 8 |  |
|  | 400 | 82G |  |  |  |  |  |  |  |
|  | 6.25 | 7 |  |  |  |  | 1 | 5 |  |
|  | 25 | 8 |  |  |  |  | 4 | 8 |  |
|  | 100 | 92G |  |  |  |  | 82G | 8 |  |
|  | 1.56 | 1 |  |  |  |  | 1 | 1 |  |
|  | 6.25 | 4 |  |  |  |  | 1 | 1 |  |
|  | 25 | 7 |  |  |  |  | 1 | 4 |  |
| 61 | 400 | 8 | 1 | 1 | 1 | 1 |  |  |  |
|  | 25 | 4 |  |  |  |  |  |  |  |
|  | 400 | 7 |  |  |  |  |  |  |  |
|  | 100 | 5 |  |  |  |  | 12G | 7 | 8 |
|  | 100 |  |  |  |  |  |  | 1 | 4 |
|  | 25 |  |  |  |  |  |  | 1 | 3 |
|  | 6.25 |  |  |  |  |  |  | 1 | 1 |
| 62 | 400 | 72G | 1 | 12G | 1 | 5 |  |  |  |
|  | 400 | 72G | 1 | 12G | 1 | 5 |  |  |  |
| 64 | 400 | 72G | 1 | 4 | 1 | 1 |  |  |  |
|  | 400 | 72G | 1 | 4 | 1 | 1 |  |  |  |
| 65 | 400 | 6 | 1 | 7 | 1 | 12F |  |  |  |
|  | 100 | 5 |  | 5 |  |  | 1 | 5 | 8 |
|  | 400 | 6 |  | 8 |  |  |  |  |  |
|  | 25 | 2 |  | 1 |  |  |  |  |  |
|  | 6.25 |  |  |  |  |  |  |  | 3 |
|  | 100 |  |  |  |  |  |  |  | 8 |
|  | 25 |  |  |  |  |  |  |  | 6 |

Test VI

Certain compounds of the invention were further tested in the greenhouse against a number of plant pathogens, using a test method in which the time of application of the compound and the time of inoculation with the pathogen were varied with respect to each other, to evaluate treatments for protective and curative disease control. In the tables below, the time of application is described as the number of hours before inoculation of the test plants with the pathogen. Thus, a negative time means that the pathogen was inoculated before treatment.

In these tests, the compounds were formulated for application at various rates, set out in the tables below as parts per million of the spray composition, as described in Test II above. All compounds were applied as foliar sprays.

The results of the tests were evaluated on the 1–9 rating scale, as described in Test V above.

The following plant pathogens and their corresponding host plants were used in this test.

Cercospora beticola (leaf spot) on sugar beet
Venturia inaequalis (scab) on apple
Podosphaera leucotricha (powdery mildew) on apple
Erysiphe cichoracearum (powdery mildew) on cucumber and squash
Uncinula necator (powdery mildew) on grape The results of the test are shown in Table VI below.

TABLE VI

| EX. NO. | PPM | TIME | CERC SPOR | APPL SCAB | APPL MDEW | CUKE MDEW | GRAP MDEW | SQUA MDEW |
|---|---|---|---|---|---|---|---|---|
| 6 | 400 | 2 | 9.0 |  |  |  |  |  |
|  | 100 | 2 | 8.0 |  |  |  |  |  |
|  | 50 | 2 | 9.0 |  |  |  |  |  |

TABLE VI-continued

| EX. NO. | PPM | TIME | CERC SPOR | APPL SCAB | APPL MDEW | CUKE MDEW | GRAP MDEW | SQUA MDEW |
|---|---|---|---|---|---|---|---|---|
| | 50 | −72 | | 9.0 | | | | |
| | 50 | 2 | | 9.0 | | | | |
| | 40 | −168 | | | 5.0 | | | |
| | 40 | 2 | | | | 1.0 | | |
| | 40 | 48 | | | | 1.0 | | |
| | 40 | −168 | | | | | 8.0 | |
| | 25 | 2 | | 9.0 | | | | |
| | 20 | 2 | | 8.0 | | | | |
| | 20 | 72 | | 4.0 | | | | |
| | 20 | 144 | | 6.0 | | | | |
| | 20 | −168 | | | 1.0 | | | |
| | 20 | 2 | | | | 9.0 | | |
| | 20 | 2 | | | | 1.0 | | |
| | 20 | 48 | | | | 1.0 | | |
| | 20 | 48 | | | | 5.0 | | |
| | 20 | 120 | | | | 5.0 | | |
| | 20 | 168 | | | | 4.0 | | |
| | 20 | −168 | | | | | 3.0 | |
| | 12.5 | −72 | | 9.0 | | | | |
| | 12.5 | 2 | | 8.5 | | | | |
| | 10 | 2 | | 7.0 | | | | |
| | 10 | 72 | | 3.0 | | | | |
| | 10 | 144 | | 1.0 | | | | |
| | 6.2 | −72 | | 9.0 | | | | |
| 13 | 400 | 2 | 9.0 | | | | | |
| | 100 | 2 | 9.0 | | | | | |
| | 50 | 2 | 9.0 | | | | | |
| | 50 | −72 | | 9.0 | | | | |
| | 50 | 2 | | 9.0 | | | | |
| | 40 | −168 | | | 6.0 | | | |
| | 40 | 2 | | | | 6.0 | | |
| | 40 | 48 | | | | 6.0 | | |
| | 40 | −168 | | | | | 8.0 | |
| | 25 | −72 | | 9.0 | | | | |
| | 25 | 2 | | 9.0 | | | | |
| | 20 | 2 | | 5.0 | | | | |
| | 20 | 72 | | 1.0 | | | | |
| | 20 | 144 | | 7.0 | | | | |
| | 20 | −168 | | | 6.0 | | | |
| | 20 | 2 | | | | 9.0 | | |
| | 20 | 2 | | | | 5.0 | | |
| | 20 | 48 | | | | 5.0 | | |
| | 20 | 48 | | | | 1.0 | | |
| | 20 | 120 | | | | 5.0 | | |
| | 20 | 168 | | | | 3.0 | | |
| | 20 | −168 | | | | | 5.0 | |
| | 12.5 | −72 | | 8.0 | | | | |
| | 12.5 | 2 | | 8.5 | | | | |
| | 10 | 2 | | | | | | 8.0 |
| | 10 | 2 | | 5.0 | | | | |
| | 10 | 72 | | 1.0 | | | | |
| | 10 | 144 | | 3.0 | | | | |
| | 6.2 | −72 | | 8.0 | | | | |
| | 5 | 2 | | | | | | 8.0 |
| | 2.5 | 2 | | | | | | 8.0 |
| 20 | 400 | 2 | 9.0 | | | | | |
| | 100 | 2 | 9.0 | | | | | |
| | 50 | 2 | 9.0 | | | | | |
| | 50 | −72 | | 9.0 | | | | |
| | 50 | 2 | | 5.5 | | | | |
| | 40 | −168 | | | 5.0 | | | |
| | 40 | 2 | | | | 1.0 | | |
| | 40 | 48 | | | | 1.0 | | |
| | 40 | −168 | | | | | 2.0 | |
| | 25 | −72 | | 8.0 | | | | |
| | 25 | 2 | | 7.0 | | | | |
| | 20 | 2 | | 1.0 | | | | |
| | 20 | 72 | | 1.0 | | | | |
| | 20 | 144 | | 1.0 | | | | |
| | 20 | −168 | | | 5.0 | | | |
| | 20 | 2 | | | | 9.0 | | |
| | 20 | 2 | | | | 1.0 | | |
| | 20 | 48 | | | | 4.0 | | |
| | 20 | 48 | | | | 1.0 | | |
| | 20 | 120 | | | | 3.0 | | |
| | 20 | 168 | | | | 2.0 | | |
| | 20 | −168 | | | | | 1.0 | |
| | 12.5 | −72 | | 8.0 | | | | |
| | 12.5 | 2 | | 5.0 | | | | |
| | 10 | 2 | | 1.0 | | | | |

TABLE VI-continued

| EX. NO. | PPM | TIME | CERC SPOR | APPL SCAB | APPL MDEW | CUKE MDEW | GRAP MDEW | SQUA MDEW |
|---|---|---|---|---|---|---|---|---|
| | 10 | 72 | | 1.0 | | | | |
| | 10 | 144 | | 1.0 | | | | |
| | 6.2 | −72 | | 3.0 | | | | |
| 23 | 50 | −72 | | 9.0 | | | | |
| | 50 | 2 | | 8.0 | | | | |
| | 40 | −168 | | | 8.0 | | | |
| | 40 | 2 | | | | 1.0 | | |
| | 40 | 48 | | | | 1.0 | | |
| | 40 | −168 | | | | | 7.0 | |
| | 25 | −72 | | 8.0 | | | | |
| | 25 | 2 | | 6.0 | | | | |
| | 20 | 2 | | 5.0 | | | | |
| | 20 | 72 | | 4.0 | | | | |
| | 20 | 144 | | 5.0 | | | | |
| | 20 | −168 | | | 7.0 | | | |
| | 20 | 2 | | | | 6.0 | | |
| | 20 | 2 | | | | 1.0 | | |
| | 20 | 48 | | | | 1.0 | | |
| | 20 | 48 | | | | 1.0 | | |
| | 20 | 120 | | | | 1.0 | | |
| | 20 | 168 | | | | 1.0 | | |
| | 20 | −168 | | | | | 7.0 | |
| | 12.5 | −72 | | 8.0 | | | | |
| | 12.5 | 2 | | 5.0 | | | | |
| | 10 | 2 | | 1.0 | | | | |
| | 10 | 72 | | 1.0 | | | | |
| | 10 | 144 | | 1.0 | | | | |
| | 6.2 | −72 | | 8.0 | | | | |
| 25 | 400 | 2 | 9.0 | | | | | |
| | 100 | 2 | 8.0 | | | | | |
| | 50 | 2 | 9.0 | | | | | |
| | 50 | −72 | | 9.0 | | | | |
| | 50 | 2 | | 8.0 | | | | |
| | 40 | −168 | | | 6.0 | | | |
| | 40 | 2 | | | | 8.0 | | |
| | 40 | 48 | | | | 3.0 | | |
| | 40 | −168 | | | | | 7.0 | |
| | 25 | −72 | | 8.0 | | | | |
| | 25 | 2 | | 6.0 | | | | |
| | 20 | 2 | | 8.0 | | | | |
| | 20 | 72 | | 7.0 | | | | |
| | 20 | 144 | | 1.0 | | | | |
| | 20 | −168 | | | 5.0 | | | |
| | 20 | 2 | | | | 9.0 | | |
| | 20 | 2 | | | | 5.0 | | |
| 25 | 20 | 48 | | | | 5.0 | | |
| | 20 | 48 | | | | 1.0 | | |
| | 20 | 120 | | | | 4.0 | | |
| | 20 | 168 | | | | 3.0 | | |
| | 20 | −168 | | | | | 5.0 | |
| | 12.5 | −72 | | 4.0 | | | | |
| | 12.5 | 2 | | 5.5 | | | | |
| | 10 | 2 | | 7.0 | | | | |
| | 10 | 72 | | 4.0 | | | | |
| | 10 | 144 | | 4.0 | | | | |
| | 62 | −72 | | 4.0 | | | | |
| 44 | 400 | 2 | 9.0 | | | | | |
| | 100 | 2 | 9.0 | | | | | |
| | 50 | 2 | 9.0 | | | | | |
| | 50 | −72 | | 9.0 | | | | |
| | 50 | 2 | | 7.0 | | | | |
| | 40 | −168 | | | 8.0 | | | |
| | 40 | 2 | | | | 7.0 | | |
| | 40 | 48 | | | | 7.0 | | |
| | 40 | −168 | | | | | 5.0 | |
| | 25 | −72 | | 9.0 | | | | |
| | 25 | 2 | | 7.5 | | | | |
| | 20 | 2 | | 6.0 | | | | |
| | 20 | 72 | | 5.0 | | | | |
| | 20 | 144 | | 1.0 | | | | |
| | 20 | −168 | | | 7.0 | | | |
| | 20 | 2 | | | | 9.0 | | |
| | 20 | 2 | | | | 5.0 | | |
| | 20 | 48 | | | | 1.0 | | |
| | 20 | 48 | | | | 1.0 | | |
| | 20 | 120 | | | | 5.0 | | |
| | 20 | 168 | | | | 4.0 | | |
| | 20 | −168 | | | | | 1.0 | |
| | 12.5 | −72 | | 9.0 | | | | |
| | 12.5 | 2 | | 1.0 | | | | |

TABLE VI-continued

| EX. NO. | PPM | TIME | CERC SPOR | APPL SCAB | APPL MDEW | CUKE MDEW | GRAP MDEW | SQUA MDEW |
|---|---|---|---|---|---|---|---|---|
|  | 10 | 2 |  | 8.0 |  |  |  |  |
|  | 10 | 72 |  | 7.0 |  |  |  |  |
|  | 10 | 144 |  | 1.0 |  |  |  |  |
|  | 6.2 | −72 |  | 7.0 |  |  |  |  |
| 59 | 400 | 2 | 9.0 |  |  |  |  |  |
|  | 100 | 2 | 9.0 |  |  |  |  |  |
|  | 50 | 2 | 7.0 |  |  |  |  |  |
|  | 50 | −72 |  | 9.0 |  |  |  |  |
|  | 50 | 2 |  | 6.0 |  |  |  |  |
|  | 40 | −168 |  |  | 8.0 |  |  |  |
|  | 40 | 2 |  |  |  | 8.0 |  |  |
|  | 40 | 48 |  |  |  | 7.0 |  |  |
|  | 40 | −168 |  |  |  |  | 1.0 |  |
|  | 25 | −72 |  | 8.0 |  |  |  |  |
|  | 25 | 2 |  | 3.5 |  |  |  |  |
|  | 20 | 2 |  | 5.0 |  |  |  |  |
|  | 20 | 72 |  | 4.0 |  |  |  |  |
|  | 20 | 144 |  | 1.0 |  |  |  |  |
|  | 20 | −168 |  |  | 7.0 |  |  |  |
|  | 20 | 2 |  |  |  | 8.5 |  |  |
|  | 20 | 2 |  |  |  | 5.0 |  |  |
|  | 20 | 48 |  |  |  | 5.0 |  |  |
|  | 20 | 48 |  |  |  | 5.0 |  |  |
|  | 20 | 120 |  |  |  | 6.0 |  |  |
|  | 20 | 168 |  |  |  | 6.0 |  |  |
|  | 20 | −168 |  |  |  |  | 1.0 |  |
|  | 12.5 | −72 |  | 6.0 |  |  |  |  |
|  | 12.5 | 2 |  | 5.0 |  |  |  |  |
|  | 10 | 2 |  | 6.0 |  |  |  |  |
|  | 10 | 72 |  | 1.0 |  |  |  |  |
|  | 10 | 144 |  | 1.0 |  |  |  |  |
|  | 6.2 | −72 |  | 8.0 |  |  |  |  |
| 60 | 400 | 2 | 9.0 |  |  |  |  |  |
|  | 100 | 2 | 9.0 |  |  |  |  |  |
|  | 50 | 2 | 1.0 |  |  |  |  |  |
|  | 50 | −72 |  | 7.0 |  |  |  |  |
|  | 50 | 2 |  | 8.5 |  |  |  |  |
|  | 40 | −168 |  |  | 5.0 |  |  |  |
|  | 40 | −168 |  |  |  |  | 5.0 |  |
|  | 25 | −72 |  | 9.0 |  |  |  |  |
|  | 25 | 2 |  | 2.0 |  |  |  |  |
|  | 20 | −168 |  |  | 5.0 |  |  |  |
|  | 20 | 2 |  |  |  | 1.0 |  |  |
|  | 20 | 48 |  |  |  | 1.0 |  |  |
|  | 20 | 120 |  |  |  | 2.0 |  |  |
|  | 20 | 168 |  |  |  | 1.0 |  |  |
|  | 20 | −168 |  |  |  |  | 1.0 |  |
|  | 12.5 | −72 |  | 5.0 |  |  |  |  |
|  | 12.5 | 2 |  | 4.0 |  |  |  |  |
|  | 6.2 | −72 |  | 1.0 |  |  |  |  |

Test VII

Representative compounds of the invention were tested further for apple scab control at low rates. The compounds were formulated and applied to the foliage of apple seedlings as described in Test II. Treated plants were inoculated by spraying a suspension of spores of the pathogen over them a few hours after treatment.

When the disease was well established on untreated control plants, the disease control provided by the compounds was observed and rated on a 0–10 scale, which is a slightly expanded version of the 1–9 scale explained above in Test V, wherein 0 indicates no control and 10 indicates complete control.

TABLE VII

| EX. NO. | PPM | CONTROL RATING |
|---|---|---|
| 3 | 6.25 | 4 |
| 3 | 12.5 | 5 |
| 3 | 25 | 8 |
| 3 | 50 | 9.5 |
| 6 | 6.25 | 9 |
| 6 | 12.5 | 8 |
| 6 | 25 | 10 |
| 6 | 50 | 10 |
| 13 | 6.25 | 0 |
| 13 | 12.5 | 4 |
| 13 | 25 | 4 |
| 13 | 50 | 9.5 |
| 43 | 6.25 | 0 |
| 43 | 12.5 | 0 |
| 43 | 25 | 10 |
| 43 | 50 | 9.5 |
| 56 | 6.25 | 0 |
| 56 | 12.5 | 0 |
| 56 | 25 | 0 |
| 56 | 50 | 0 |

Test VIII

Compounds of the invention were tested against five typical diseases of small grains in the greenhouse. The test was carried out substantially according to the method of Test II above, except that the pathogens and their respective hosts were as follows.

*Erysiphe graminis tritici* (powdery mildew) on wheat

*Erysiphe graminis hordei* (powdery mildew) on barley
*Puccinia recondita tritici* (leaf rust) on wheat
*Helminthosporium sativum* (leaf spot) on wheat
*Septoria tritici* (leaf blotch) on wheat The results of the tests were evaluated on the 1–9 scale, and reported as follows. The following results are the means of from 1 to 5 trials with the various pathogens.

TABLE VIII
CONTROL OF WHEAT AND BARLEY DISEASES FROM PROTECTIVE FOLIAR APPLICATIONS

| EX. NO. | PPM | WHET MDEW | BARL MDEW | LEAF RUST | HELM SPOR | SEPT ORIA |
|---|---|---|---|---|---|---|
| 6 | 6.25 | 6.3 | 6.5 | 3 | 6 | 1 |
|  | 12.5 | 7 | 8 | 1 | 8 | 6 |
|  | 25 | 8 | 8.5 | 3.7 | 9 | 9 |
|  | 50 | 9 |  | 6 | 9 | 9 |
|  | 100 | 8.7 |  | 7.2 | 9 | 9 |
| 13 | 6.25 | 4 | 7.5 | 1 | 1 | 1 |
|  | 12.5 | 5.1 | 7.5 | 1 | 2 | 1 |
|  | 25 | 6.5 | 8 | 1 | 7.3 | 3 |
|  | 50 | 8 |  | 1.3 | 8.7 | 7 |
|  | 100 | 9 |  | 3.8 | 9 | 9 |
| 20 | 6.25 | 2.3 | 1 | 1 | 4 | 1 |
|  | 12.5 | 3.2 | 1 | 1 | 5 | 1 |
|  | 25 | 4.2 | 3.5 | 1 | 5.7 | 1 |
|  | 50 | 5 |  | 1.3 | 8 | 1 |
|  | 100 | 6.3 |  | 3.3 | 8.3 | 4 |
| 23 | 2.5 | 1.2 | 1 | 2 | 4 |  |
|  | 12.5 | 4.8 | 4 | 1 | 5 | 6 |
|  | 25 | 5.8 | 5.5 | 1 | 3.5 | 6 |
|  | 50 | 7.7 |  | 1.5 | 7.8 | 8.5 |
|  | 100 | 8.2 |  | 3 | 7.8 | 8.5 |
| 25 | 6.25 | 4 | 6.5 | 1 | 5 | 1 |
|  | 12.5 | 6.2 | 6.5 | 1 | 6 | 4 |
|  | 25 | 7 | 8 | 2 | 7.8 | 8 |
|  | 50 | 8 |  | 5 | 9 | 9 |
|  | 100 | 8.2 | 6.7 | 8.5 | 9 |  |
| 44 | 6.25 | 6.5 | 6 | 1 | 8 | 9 |
|  | 12.5 | 6.5 | 7 | 1 | 9 | 9 |
|  | 25 | 7.2 | 7.5 | 3 | 8.7 | 9 |
|  | 50 | 8 |  | 5 | 8 | 8.5 |
|  | 100 | 8 |  | 7 | 8 | 8.5 |
| 59 | 6.25 | 3.3 | 7 | 1 | 1 | 1 |
|  | 12.5 | 5.2 | 8 | 1 | 1 | 1 |
|  | 25 | 6.2 | 8 | 1 | 3.7 | 3 |
|  | 50 | 5.5 |  | 1.7 | 6.7 | 8 |
|  | 100 | 7.7 |  | 3.3 | 8.3 | 9 |

Test IX

A number of the compounds were tested against wheat powdery mildew, applied at such times as to evaluate both the curative and protective effect of the compounds at very low application rates. The method was as described in Test II above, except that the curative applications were made on the second day following the inoculation of wheat seedlings with powdery mildew, and the protective applications were made before the inoculation, only enough time being allowed to let the spray dry. The results of the experiments were evaluated on the 1–9 scale, and are reported as the means of two trials.

TABLE IX

| EX. NO. | PPM | 2 Day Curative | 0 Day Protective |
|---|---|---|---|
| 6 | 3.125 | 7 | 5 |
|  | 6.25 | 8 | 6.5 |
|  | 12.5 | 8.5 | 7 |
| 13 | 3.125 | 1.5 | 1.5 |
|  | 6.25 | 4.5 | 2 |
|  | 12.5 | 5.5 | 4 |
| 20 | 3.125 | 1 | 1 |
|  | 6.25 | 1 | 1.5 |
|  | 12.5 | 1 | 2 |

TABLE IX-continued

| EX. NO. | PPM | 2 Day Curative | 0 Day Protective |
|---|---|---|---|
| 23 | 3.125 | 1 | 1 |
|  | 6.25 | 1 | 1 |
|  | 12.5 | 3.5 | 3.5 |
| 25 | 3.125 | 3 | 1.5 |
|  | 6.25 | 6.5 | 4 |
|  | 12.5 | 8 | 6 |
| 44 | 3.125 | 8 | 5.5 |
|  | 6.25 | 8 | 7 |
|  | 12.5 | 8 | 7 |
| 59 | 3.125 | 1 | 1 |
|  | 6.25 | 1.5 | 2.5 |
|  | 12.5 | 5.5 | 4.5 |
| 60 | 3.125 | 3 | 2.5 |
|  | 6.25 | 7 | 4.5 |
|  | 12.5 | 7.5 | 7 |
| Control | 0 | 1 | 1 |

Table X

The experiments reported here were carried out to evaluate protective and curative control of wheat leaf rust. The experiments were carried out in the same manner used in Test IX above.

TABLE X

| EX. NO. | PPM | 2 Day Curative | 0 Day Protective |
|---|---|---|---|
| 6 | 25 | 3 | 3 |
|  | 50 | 7 | 4 |
|  | 100 | 8 | 6.5 |
| 13 | 25 | 5 | 1 |
|  | 50 | 5 | 1.5 |
|  | 100 | 7.5 | 4 |
| 20 | 25 | 1 | 1 |
|  | 50 | 3.5 | 1.5 |
|  | 100 | 3 | 1.5 |
| 23 | 25 | 4 | 1 |
|  | 50 | 4.5 | 1 |
|  | 100 | 7 | 3 |
| 25 | 25 | 6 | 2.5 |
|  | 50 | 7.5 | 4.5 |
|  | 100 | 9 | 6 |
| 44 | 25 | 4.5 | 1 |
|  | 50 | 5.5 | 3.5 |
|  | 100 | 8 | 6 |
| 59 | 25 | 2 | 1 |
|  | 50 | 4.5 | 2 |
|  | 100 | 4 | 3 |
| 60 | 25 | 2.5 | 1 |
|  | 50 | 1 | 1 |
|  | 100 | 1 | 1 |
| Control | 0 | 1 | 1 |

Text XI

Further protective and curative applications of compounds were carried out against wheat leaf rust, as described in Test X, except that the period between inoculation and curative treatment was varied from 1 to 3 days. The results are from one trial.

TABLE XI

| EX. NO. | PPM | Curative Control | | | Protective |
|---|---|---|---|---|---|
|  |  | 3 Days | 2 Days | 1 Day | 0 Day |
| 6 | 12.5 | 5 | 1 | 1 | 1 |
|  | 25 | 7 | 1 | 3 | 1 |
|  | 50 | 9 | 7 | 7 | 5 |
|  | 100 | 9 | 8 | 8 | 6 |
| 13 | 12.5 | 1 | 1 | 1 | 1 |
|  | 25 | 4 | 1 | 1 | 1 |
|  | 50 | 7 | 3 | 2 | 2 |
|  | 100 | 9 | 6 | 6 | 5 |
| 20 | 12.5 | 1 | 1 | 1 | 1 |
|  | 25 | 2 | 1 | 1 | 1 |
|  | 50 | 4 | 1 | 1 | 1 |

TABLE XI-continued

| EX. NO. | PPM | Curative Control 3 Days | 2 Days | 1 Day | Protective 0 Day |
|---|---|---|---|---|---|
|  | 100 | 6 | 2 | 2 | 2 |
| 23 | 12.5 | 1 | 1 | 1 | 1 |
|  | 25 | 2 | 1 | 1 | 1 |
|  | 50 | 5 | 1 | 1 | 1 |
|  | 100 | 7 | 5 | 1 | 3 |
| 25 | 12.5 | 6 | 3 | 1 | 1 |
|  | 25 | 7 | 4 | 1 | 2 |
|  | 50 | 8 | 6 | 1 | 4 |
|  | 100 | 9 | 9 | 6 | 6 |
| 44 | 12.5 | 4 | 2 | 1 | 1 |
|  | 25 | 5 | 3 | 2 | 1 |
|  | 50 | 6 | 4 | 3 | 3 |
|  | 100 | 9 | 7 | 6 | 6 |
| 59 | 12.5 | 1 | 1 | 1 | 1 |
|  | 25 | 2 | 1 | 1 | 1 |
|  | 50 | 6 | 3 | 1 | 3 |
|  | 100 | 7 | 5 | 4 | 5 |
| 60 | 12.5 | 1 | 1 | 1 | 1 |
|  | 25 | 1 | 1 | 1 | 1 |
|  | 50 | 1 | 1 | 1 | 1 |
|  | 100 | 3 | 1 | 1 | 1 |
| Control | 0 | 1 | 1 | 1 | 1 |

Test 12

The ability of compounds of the present invention to enter a plant and provide systemic control of pathogens was experimentally measured. The experiment was carried out by choosing 14 to 21-day-old wheat and barley plants, having leaves about 30 cm. long. The compounds were formulated as in Test I above, but at 100 ppm. concentration, and were sprayed on a 5-cm. transverse band near the center of a leaf. The plants were infected 24 hours later with powdery mildew, and were maintained under conditions favorable to the growth of the pathogen. When mildew was well established in untreated control plants, the distance from the treated band to the nearest infection of powdery mildew on the same leaf was measured, in both the proximal and distal directions. For each compound, ten replicate leaves were sprayed and measured, and the results were averaged to prepare the following table.

TABLE XII

| EX. NO. | Barley Distance to 1st PM Distal | Proximal | Wheat Distance to 1st PM Distal | Proximal |
|---|---|---|---|---|
| Sol. Blank | 0 cm | 0 cm | 0.2 cm | 0 cm |
| 6 | >12 | 1.3 | 1.4 | 0.1 |
| 13 | 7 | 1.7 | 0 | 0 |
| 20 | 0 | 0 | 0 | 0 |
| 23 | 0 | 0 | 0 | 0 |
| 25 | 2.4 | 0.4 | 0 | 0 |
| 44 | >11 | 1.4 | 10 | 0.3 |
| 59 | 10.4 | 1.4 | 0.6 | 0 |
| 60 | 2 | 0.2 | 0.1 | 0 |
| Control | 0 | 0 | 0 | 0 |

Test XIII

The experiments reported here were carried out to determine the ability of representative compounds to be absorbed by the roots of wheat and to translocate into the foliage of the plant and protect it from pathogens. The compounds were formulated as described in Test II above, and the formulations were uniformly syringed on the soil surface of pots in which 6-day-old wheat seedlings were growing, in amounts to provide the dosage rates described in the table below. The treated plants were inoculated with the pathogens 24 hours after treatment. When the diseases were well established on untreated control plants, the treated plants were rated for disease control on the 1–9 scale as described above. Phytotoxicity is indicated in the table by "*".

TABLE XIII
SYSTEMIC DISEASE CONTROL THROUGH SOIL DRENCH APPLICATION TO WHEAT

| EX. NO. | Rate (lb/A) | Powdery mildew | Leaf rust | Helminth-osporium | Septoria leaf blotch |
|---|---|---|---|---|---|
| 6 | 0.625 | 1 | 1 | 1 | 4 |
|  | 1.25 | 4 | 1 | 1 | 6 |
|  | 2.5 | 6 | 1 | 1 | 8 |
| 13 | 0.625 | 1 | 1 | 1 | 5* |
|  | 1.25 | 1 | 1 | 1 | 9* |
|  | 2.5 | 3 | 5 | 2 | 9* |
| 20 | 0.625 | 1 | 1 | 1 | 4 |
|  | 1.25 | 4 | 1 | 1 | 8* |
|  | 2.5 | 5 | 5 | 1 | 8* |
| 23 | 0.625 | 8 | 4 | 1 | 9 |
|  | 1.25 | 9 | 6 | 1 | 9 |
|  | 2.5 | 9* | 8.5* | 6.5 | 9* |
| 25 | 0.625 | 5 | 1 | 1 | 9 |
|  | 1.25 | 6 | 5 | 1 | 9* |
|  | 2.5 | 7* | 6.5* | 1 | 9* |
| 44 | 0.625 | 1 | 1 | 1 | 9 |
|  | 1.25 | 3 | 1 | 1 | 9 |
|  | 2.5 | 7.5* | 3.5 | 1 | 9* |
| 59 | 0.625 | 1 | 1 | 1 | 7 |
|  | 1.25 | 2 | 1 | 1 | 7 |
|  | 2.5 | 3 | 1 | 1 | 9 |
| 60 | 0.625 | 1 | 1 | 1 | 1 |
|  | 1.25 | 1 | 1 | 1 | 6 |
|  | 2.5 | 3 | 1 | 1 | 9* |
| Control | 0 | 1 | 1 | 1 | 1 |

Test XIV

This test was carried out to evaluate the disease control produced by coating seed with compounds of the present invention. The compounds were applied to healthy wheat and smut-infected (*Ustilago nuda*) barley seed by dissolving the proper amount of compound to treat 10 g. of seed in 2 ml. of 1:1 acetone:ethanol, and spraying the solution onto the seed in a small tumbling drum. When the solvents had evaporated, twenty-five seeds were planted in a 6-inch plastic pot containing sterilized greenhouse soil. Four pots were planted of each treatment. The wheat seeds were allowed to grow out in the greenhouse for 7 days, and was then infected with powdery mildew. The barley seed was naturally infected with loose smut. Control of wheat powdery mildew was rated 16 days after planting, and control of barley loose smut was rated 80 days after planting. The 1–9 scale was used to rate disease control. The results of the replicate treatments were averaged to prepare the table below.

TABLE XIV
DISEASE CONTROL FROM SEED COAT TREATMENT

| EX. NO | Rate (g./kg.) | Wheat Powdery Mildew (16 Days After Planting) | Barley Loose Smut (80 Days After Planting) |
|---|---|---|---|
| 6 | 0.125 | 1 | 9 |
|  | 0.25 | 1 | 9 |
|  | 0.5 | 1 | 9 |
| 13 | 0.125 | 2.2 | 6 |
|  | 0.25 | 4 | 6 |
|  | 0.5 | 6.8 | 9 |
| 20 | 0.125 | 1 | 9 |
|  | 0.25 | 1 | 9 |
|  | 0.5 | 1 | 9 |
| 23 | 0.125 | 7.2 | 5 |
|  | 0.25 | 8.8 | 9 |

TABLE XIV-continued
DISEASE CONTROL FROM SEED COAT TREATMENT

| EX. NO | Rate (g./kg.) | Wheat Powdery Mildew (16 Days After Planting) | Barley Loose Smut (80 Days After Planting) |
|---|---|---|---|
|  | 0.5 | 9 | 9 |
| 25 | 0.125 | 1 | 9 |
|  | 0.25 | 1 | 9 |
|  | 0.5 | 1 | 9 |
| 44 | 0.125 | 1 | 5 |
|  | 0.25 | 1 | 9 |
|  | 0.5 | 1 | 9 |
| 59 | 0.125 | 1 | 1 |
|  | 0.25 | 1 | 6 |
|  | 0.5 | 1 | 9 |
| 60 | 0.125 | 1 | 1 |
|  | 0.25 | 4.5 | 1 |
|  | 0.5 | 7.2 | 2 |
| Control | 0 | 1 | 1 |

Test XV

Representative compounds of the invention were tested against eyespot disease (*Pseudocercosporella herpotrichoides*) of wheat in the greenhouse, by applying the compounds to the foliage of wheat plants. The compounds were formulated as described in Test II above, and were sprayed on 14-day-old wheat plants growing in plastic pots. When the applications of spray had dried, the plants were inoculated with the pathogen. When the disease was well established on untreated control plants, the disease control provided by the test compounds was rated on the 1–9 scale, and injury caused by the compounds was rated on the 0–10 scale. Replicate treatments were averaged to prepare the following table of results.

TABLE XV
FOLIAR APPLICATION FOR CONTROL OF WHEAT EYESPOT

| EX. NO | Rate (ppm) | Disease Control (1–9) | Crop Injury (0–10) |
|---|---|---|---|
| 6 | 25 | 9 | 0 |
|  | 100 | 9 | 2 |
|  | 400 | 9 | 3 |
| 13 | 25 | 3 | 0 |
|  | 100 | 8.5 | 2 |
|  | 400 | 9 | 4 |
| 20 | 25 | 1.5 | 0 |
|  | 100 | 9 | 1 |
|  | 400 | 9 | 3 |
| 23 | 25 | 1 | 0 |
|  | 100 | 1.5 | 0 |
|  | 400 | 3 | 0 |
| 25 | 25 | 4 | 0 |
|  | 100 | 7.5 | 0 |
|  | 400 | 9 | 4 |
| 44 | 25 | 8.5 | 0 |
|  | 100 | 9 | 1 |
|  | 400 | 9 | 4 |
| 59 | 25 | 1.5 | 0 |
|  | 100 | 2 | 1 |
|  | 400 | 9 | 2 |
| 60 | 25 | 1 | 0 |
|  | 100 | 5.5 | 0 |
|  | 400 | 8.5 | 4 |
| Control | 0 | 1.5 | 0 |

Test XVI

Compounds of the invention were tested against *Pyrenophora teres* (net blotch) and *Rhynchosporium secalis* (leaf scald) of barley in the greenhouse. The compounds were formulated substantially as described in Test II above, and were applied to young barley plants. The compounds were tested for protective control against both of the diseases by applying the compounds before inoculation with the pathogen, on the same day, and were also tested for curative control of leaf scald by inoculating the plants one day before application of the compounds. In these tests, the disease control was measured as a percent control, and the replicates were averaged to prepare the following table.

TABLE XVI
BARLEY DISEASE CONTROL

| EX. NO. | Rate (ppm) | Net Blotch Control | Leaf Scald Control Protect. | Leaf Scald Control Curative |
|---|---|---|---|---|
| 6 | 12.5 | 28% | 83% | 100% |
|  | 25 | 52 | 81 | 100 |
|  | 50 | 60 | 90 | 100 |
|  | 100 | 74 | 95 | 100 |
| 13 | 12.5 | 42 | 89 | 95 |
|  | 25 | 64 | 95 | 96 |
|  | 50 | 72 | 97 | 100 |
|  | 100 | 81 | 99 | 100 |
| 20 | 12.5 | 42 | 12 | 0 |
|  | 25 | 52 | 2 | 0 |
|  | 50 | 62 | 29 | 0 |
|  | 100 | 87 | 63 | 22 |
| 23 | 12.5 | 31 | 60 | — |
|  | 25 | 8 | 30 | — |
|  | 50 | 31 | 48 | — |
|  | 100 | 43 | 58 | — |
| 25 | 12.5 | 51 | 84 | 81 |
|  | 25 | 69 | 79 | 100 |
|  | 50 | 78 | 98 | 100 |
|  | 100 | 84 | 99 | 100 |
| 44 | 12.5 | 40 | 91 | 100 |
|  | 25 | 60 | 94 | 100 |
|  | 50 | 62 | 99 | 100 |
|  | 100 | 74 | 100 | 100 |
| 59 | 12.5 | 34 | 13 | 0 |
|  | 25 | 29 | 42 | 57 |
|  | 50 | 42 | 89 | 98 |
|  | 100 | 74 | 95 | 100 |
| 60 | 12.5 | 26 | 27 | 8 |
|  | 25 | 16 | 81 | 94 |
|  | 50 | 26 | 87 | 99 |
|  | 100 | 52 | 87 | 100 |

Test XVII

The ability of compounds of the invention to control *Cercospora arachicola* (leaf spot) of peanut and *C. beticola* (leaf spot) of sugar beet was evaluated in these tests. The compounds, formulated as described in Test II above, were applied to the foliage of young peanut and sugar beet plants, growing in individual plastic pots in the greenhouse. In some tests, the compound was applied and allowed to dry before inoculating the plants with disease, and in other cases the plants were inoculated 5 days before the application of the compounds, to test the compounds' curative activity. The effect of the compounds was evaluated, on the 1–9 scale, when the disease was well established on untreated control plants. Two or three replicate trials were made and averaged to prepare the following table.

TABLE XVII
CONTROL OF CERCOSPORA LEAF SPOT BY PROTECTIVE AND CURATIVE FOLIAR APPLICATIONS

| EX. NO | Rate (ppm) | Peanut Protective | Peanut Curative | Sugar Beet Protective | Sugar Beet Curative |
|---|---|---|---|---|---|
| 6 | 12.5 | 7.5 |  | 7 | 6 |
|  | 25 | 7.3 | 9 | 7.4 | 6.5 |
|  | 50 | 9 | 7 | 8.4 | 8 |
|  | 100 | 9 | 8.5 | 9 | 7.5 |
| 13 | 12.5 | 3 |  | 4.8 | 3 |

TABLE XVII-continued

CONTROL OF CERCOSPORA LEAF SPOT BY
PROTECTIVE AND CURATIVE FOLIAR APPLICATIONS

| EX. NO | Rate (ppm) | Peanut Protective | Peanut Curative | Sugar Beet Protective | Sugar Beet Curative |
|---|---|---|---|---|---|
|  | 25 | 3 | 1 | 8 | 6 |
|  | 50 | 6.7 | 7 | 8.8 | 7.5 |
|  | 100 | 6.7 | 5 | 8.5 | 8.5 |
| 20 | 12.5 | 3 |  | 5.4 | 2 |
|  | 25 | 1.3 | 2.5 | 5 | 1 |
|  | 50 | 2.5 | 2 | 5.6 | 2.5 |
|  | 100 | 3.7 | 4.7 | 7.5 | 5.5 |
| 23 | 12.5 | 6 |  | 4.8 | 1 |
|  | 25 | 2.7 | 1 | 4 | 1 |
|  | 50 | 5.5 | 8 | 5.8 | 1 |
|  | 100 | 2.3 | 2.7 | 7 | 4 |
| 25 | 12.5 | 5 |  | 5.4 | 2 |
|  | 25 | 6 | 6 | 6.4 | 7 |
|  | 50 | 8.7 | 7 | 8 | 7 |
|  | 100 | 7 | 8.5 | 9 | 7 |
| 44 | 12.5 | 7.5 |  | 7 | 1.5 |
|  | 25 | 5 | 1 | 7 | 4 |
|  | 50 | 8 | 7 | 7.4 | 7.5 |
|  | 100 | 8.5 | 8.5 | 9 | 7 |
| 59 | 12.5 | 6.5 |  | 3.3 | 2 |
|  | 25 | 5.7 | 1 | 4.4 | 5 |
|  | 50 | 7 | 7 | 6.4 | 2 |
|  | 100 | 6.5 | 6.5 | 6.6 | 6.5 |
| 60 | 12.5 | 7 |  | 4.8 | 1 |
|  | 25 | 4 | 1 | 4.2 | 3.5 |
|  | 50 | 3 | 5 | 5.8 | 4 |
|  | 100 | 2.3 | 3.5 | 7 | 3.5 |

Test XVIII

The compound of Example 13 was tested against four isolates of cucumber powdery mildew (*Sphaerotheca fuliginea*). Three of the isolates were resistant to the known fungicide fenarimol, and the other isolate was sensitive to that fungicide. The test compound was formulated and applied to seedling cucumber plants, and the plants were inoculated with the pathogen when the spray of compound had dried on the foliage. When the disease was well established in control plants, 12 days after application of the compounds, the disease control was rated as percent control by experienced observers. The results are reported in Table XVIII below. In the table, isolate 1 is the pathogen which is sensitive to fenarimol, and isolates 2, 3 and 4 are resistant to that fungicide.

TABLE XVIII

| % DISEASE CONTROL FOR ISOLATE (12 DAT) | | | | |
|---|---|---|---|---|
| PPM. | 1 | 2 | 3 | 4 |
| 1 | 30 |  | 0 | 0 |
| 2 | 62 | — | — |  |
| 5 | 85 |  | 0 | 0 |
| 10 | 91 | 0 | 0 | 22 |
| 20 | 96 | 1 | 29 | 0 |
| 50 | 98 | 10 | 50 | 27 |
| 100 | 100 | 43 | 83 | 82 |
| 250 | 100 | 99 | 82 | 87 |
| 350 | 100 | 100 | — | — |

Test XIX

The compound of Example 13 was field-tested on strawberry plants for the control of strawberry leaf spot (*Mycosphaerella fragariae*). The plots contained established strawberry plants, in 2-foot-wide rows, and each test plot consisted of five feet of one row. The compound was formulated as an aqueous suspension containing 1 pound of compound per gallon, and the spray compositions were prepared by dispersing a sufficient amount of the suspension in water to give the desired concentrations of 40, 80 and 160 ppm. of compound. Applications of the compound were made by spraying at the volume rate of 75 gallons of spray composition per acre, at the pre-bloom, full bloom, berry-set, fruiting, and mature fruit stages of the strawberry crop. The plants were observed and the crop injury control produced by the compound were rated, as percent injury or control, on various dates as listed below.

In no instance was crop injury observed, and so that data is omitted from the table.

Each treatment was replicated three times, and the results were averaged to prepare the following table.

| | Disease Control | | |
|---|---|---|---|
| PPM | June 11 | June 19 | July 9 |
| 40 | 80% | 63% | 53% |
| 80 | 90 | 63 | 53 |
| 160 | 95 | 73 | 77 |

Test XX

The compound of Example 13, formulated as a 1 pound per gallon aqueous suspension, was tested against apple scab on Rome apple trees. Spray compositions were made by diluting the aqueous suspension to provide the desired concentrations of compound, and were applied to the trees at the rate of 2 liters of dilute composition per tree, using a fog nozzle. Two trees constitute a treatment unit.

No crop injury was observed at any time during the experiment. The applications were made every 7 days from the green tip stage to second cover, and every 35 days thereafter.

Control of apple scab, powdery mildew and cedar rust was observed on various dates and rated as percent control. The results were as follows.

TABLE XX

| Apple Scab Control | |
|---|---|
| PPM | June 7 |
| 40 | 85% |
| 80 | 90 |
| 160 | 98 |
| Powdery Mildew Control | |
| PPM | June 26 |
| 40 | 82% |
| 80 | 95 |
| 160 | 97 |
| Cedar Rust Control | |
| PPM | June 26 |
| 40 | 100% |
| 80 | 100 |
| 160 | 100 |

Test XXI

The compound of Example 13, formulated as a 0.75 pound per gallon aqueous suspension, was tested against Cercospora leaf spot of sugar beets in field plots. The beets were planted in rows, and each test plot consisted of 10 feet of one row. Three replicate plots per treatment were used. Spray compositions were applied at the rate of 2 liters for the three replicate plots, and the concentrations of the spray compositions were adjusted to supply the desired amount of compound, calculated in grams of compound per acre of plot. The compound was applied 4 times, on August 16, August 23, August 30 and September 6. Control of leaf spot was observed on certain dates as noted in the table below, and reported as percent control of the disease. Crop injury was also observed, but is not reported because no crop injury resulted from any treatment.

TABLE XXI

| Gm./A. | Sept. 4 | Sept. 11 | Oct. 4 | Oct. 18 |
|---|---|---|---|---|
| 30 | 96% | 94% | 92% | 89% |
| 40 | 96 | 95 | 94 | 93 |
| 60 | 98 | 97 | 96 | 96 |
| 80 | 98 | 97 | 94 | 93 |

Test XXII

The compound of Example 13, formulated as a pound per gallon aqueous suspension, was tested on established grape plants for the control of powdery mildew and black rot (*Guignardia bidnellii*). The compound was applied, diluted to the concentrations stated below, on June 29, July 13, July 19, August 2 and August 14. The spray compositions were applied at the volume rate of 2 liters per 3 replicates, each replicate consisting of 5 feet of one row of grapes. The control of diseases and crop injury were observed at various dates named below; the crop injury results are not stated because no crop injury was ever observed in any treatment.

TABLE XXII

| | Powdery Mildew Control | |
|---|---|---|
| PPM | Aug. 3 | Aug. 29 |
| 40 | 95% | 93% |
| 80 | 98 | 97 |
| 160 | 99 | 98 |

| | Black Rot Control | |
|---|---|---|
| PPM | | Aug. 29 |
| 40 | | 0% |
| 80 | | 0 |
| 160 | | 0 |

Test XXIII

The compound of Example 13, formulated as a 1 pound per gallon aqueous suspension, was tested for control of leaf scald in barley in field plots. Each plot was five by ten feet, and each treatment was used in three such plots. Two liters of spray composition was applied to the 3 replicates. The spray compositions were prepared at a concentration which would provide the desired application rate, measured in pounds per acre.

The compound was applied twice, at the jointing and late booting stages of the crop, and the crop was observed two weeks and four weeks after the second application.

No crop injury was observed in any treatment, and the yields of barley and the weight of the barley seed produced by the test plots were the same as that from control plots. The disease control results were as follows.

TABLE XXIII

| Lb./A. | May 30 | June 11 |
|---|---|---|
| 0.125 | 60% | 66% |
| 0.25 | 63 | 80 |
| 0.5 | 73 | 90 |

Test XXIV

The compound of Example 13 was tested against Septoria leaf blotch and powdery mildew of wheat in field plots. The method was substantially the same as that used in Test XXIII, except that the compound was applied at the jointing and early heading stages of the crop. Control of the diseases was rated 16 days after the second application. There was no crop injury in any treatment, and the yield of the treated plots was not significantly different from that of untreated control plots. The results were as follows.

TABLE XXIV

| LB./A. | Powdery Mildew Control | Leaf Blotch Control |
|---|---|---|
| 0.125 | 50% | 50% |
| 0.25 | 68 | 78 |
| 0.5 | 82 | 90 |

Test XXV

The compound of Example 13 was tested against leaf rust and Septoria leaf blotch of wheat in field plots in a test carried out substantially as that of Test XXIV, except that the leaf rust disease was inoculated on the test plots on May 3. Applications of the compound were made on May 10 and May 23, and disease control was observed on June 1 and June 14. No crop injury was observed, and the yields of wheat from the treated plots ranged from 97% to 100% of the yield of untreated control plots.

TABLE XXV

| | Leaf Rust Control | | Leaf Blotch Control |
|---|---|---|---|
| Lb./A | June 1 | June 14 | June 14 |
| 0.125 | 21% | 21% | 0% |
| 0.25 | 53 | 25 | 12 |
| 0.5 | 68 | 31 | 52 |

Test XXVI

The compound of Example 3 was tested against leaf rust and Septoria leaf blotch of wheat in field plots, in a method carried out substantially as that of Test XXIV. The compound was applied twice on May 12 and May 25, and disease control was rated on June 9. There was no crop injury from the treatments.

TABLE XXVI

| LB./A. | Leaf Rust Control | Leaf Blotch Control |
|---|---|---|
| 0.25 | 37% | 14 |
| 0.5 | 21 | 0 |
| 1.0 | 80 | 0 |
| 2.0 | 82 | 0 |

Test XXVII

The compound of Example 3 was tested against Cercospora leaf spot and powdery mildew (*Erysiphe polygoni*) of sugar beet, in a field plot test carried out substantially as was that of Test XXI above. The compound was applied three times, on August 17, September 3 and September 17, and disease control was rated on October 19. No crop injury was observed.

TABLE XXVII

| PPM. | Leaf Spot Control | Powdery Mildew Control |
| --- | --- | --- |
| 600 | 80% | 100% |
| 1200 | 100 | 100 |
| 2400 | 90 | 100 |

Test XXVIII

The compound of Example 3 was tested against powdery mildew of zinnia, in a test where the compound was applied on September 3 and September 16, and the control of powdery mildew was observed and rated on September 21 and October 8. The compound was formulated as a two pound per gallon emulsifiable concentrate, and diluted to the desired concentrations. No crop injury was observed in any treatment.

TABLE XXVIII

| PPM. | September 21 | October 8 |
| --- | --- | --- |
| 300 | 87% | 92% |
| 600 | 98 | 97 |
| 1200 | 99 | 99 |

Representative compounds of this invention have been tested in herbicidal test systems to determine the range of their efficacy. In the tests described below, the compound application rates are expressed in kilograms of the compound per hectare of land (kg./ha.), except where otherwise stated.

Blank spaces in the tables below indicate that the compound was not tested against the named species.

Untreated control plants or pots were included in all tests. Ratings of the control produced by the compounds were made by comparison of the treated plants or plots with the controls.

In the tests below, the plants were rated on a 1–5 scale, on which 1 indicates normal plants and indicates dead plants or no emergence.

Test XXIX

Plastic pots were filled with a sterilized sandy loam soil and were planted to seeds of tomato, large crabgrass and pigweed. Each pot was individually fertilized.

The test compound was applied preemergence to some plants and postemergence to others. Postemergence applications of the compound were sprayed over the emerged plants about 12 days after the seeds were planted. Preemergence applications were sprayed on the soil the day after the seeds were planted.

Each test compound was dissolved in 1:1 acetone:ethanol at the rate of 2 g. per 100 ml. The solution also contained about 2 g. per 100 ml of an anionic-nonionic surfactant blend. One ml. of the solution was diluted to 4 ml. with deionized water, and 1.5 ml. of the resulting solution was applied to each pot, providing an application rate of 16.8 kg./ha. of test compound.

After the compounds were applied, the pots were moved to the greenhouse, watered as necessary, and observed and rated 10–13 days after application of the compounds.

The table below reports results of testing several compounds of the invention.

TABLE XXIX

| Compound of Example No. | Preemergence | | | Postemergence | | |
| --- | --- | --- | --- | --- | --- | --- |
| | Tomato | Large Crab-Grass | Pig-weed | Tomato | Large Crab-grass | Pig-weed |
| 1 | 1 | 3 | 1 | 2 | 1 | 2 |
| 3 | 1 | 4 | 3 | 4 | 5 | 4 |
| 4 | 1 | 3 | 2 | 2 | 1 | 2 |
| 5 | 1 | 3 | 1 | 1 | 2 | 1 |
| 6 | 1 | 4 | 4 | 2 | 3 | 2 |
| 7 | 1 | 1 | 1 | 1 | 1 | 1 |
| 8 | 1 | 1 | 1 | 2 | 3 | 1 |
| 9 | 1 | 5 | 2 | 1 | 1 | 1 |
| 10 | 1 | 2 | 1 | 2 | 2 | 1 |
| 12 | 1 | 2 | 1 | 1 | 2 | 1 |
| 13 | 1 | 1 | 1 | 1 | 1 | 1 |

Test XXX

The test was conducted in general like that described in Test XXIX, except that in this test the seeds were planted in flat metal trays, rather than in pots. The compounds were formulated according to the procedure described in Test XXIX, except that about 6 g./100 ml. of the compound was dissolved in the surfactant-containing solvent, and about 1 part of the organic solution was diluted with 12 parts of water before application to the trays. The compounds were applied at the rate of 8 lb./A., and at lower rates as shown in the table, and the results of testing representative compounds against the species named below were as follows. Preemergence tests are reported in Table A, and postemergence tests in Table B.

The species of plants are identified in the tables by letters, according to the following code.

| | |
| --- | --- |
| A | Corn |
| B | Cotton |
| C | Soybean |
| D | Wheat |
| E | Alfalfa |
| F | Sugar Beet |
| G | Rice |
| H | Cucumber |
| I | Tomato |
| J | Barley |
| K | Barnyard Grass |
| L | Lambsquarter |
| M | Cocklebur |
| N | Large Crabgrass |
| O | Mustard |
| P | Pigweed |
| Q | Ryegrass |
| R | Small Crabgrass |
| S | Foxtail |
| T | Bindweed |
| U | Wildoat |
| V | Nutgrass |
| W | Velvetleaf |
| X | Jimson Weed |
| Y | Smartweed |
| Z | Morningglory |
| a | Zinnia |

TABLE A

| EX. NO. | Rate lbs/A | Pre-emergence | | | | | | | | | | | | | | | | | | | | | | | | | |
| --- | --- | --- | --- | --- | --- | --- | --- | --- | --- | --- | --- | --- | --- | --- | --- | --- | --- | --- | --- | --- | --- | --- | --- | --- | --- | --- | --- |
| | | A | B | C | D | E | F | G | H | I | J | K | L | M | N | O | P | Q | R | S | T | U | V | W | X | Y | Z | a |
| 3 | 8 | | | | | | | | | 2 | | 4 | | | 4 | 2 | 2 | | 1 | 1 | 3 | | | 1 | | 1 | | |
| | 4 | 1 | 1 | 1 | 2 | 2 | 1 | 2 | 3 | 1 | | 3 | 4 | | 4 | 1 | 3 | | 4 | 2 | | 2 | 1 | | | 2 | 2 | |
| | 2 | 1 | 1 | 1 | 1 | 1 | 1 | 1 | 2 | 2 | | 1 | 4 | | 4 | 1 | 2 | | 4 | 2 | | 1 | 1 | | | 2 | 1 | |

TABLE A-continued

| EX. NO. | Rate lbs/A | Pre-emergence | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | | A | B | C | D | E | F | G | H | I | J | K | L | M | N | O | P | Q | R | S | T | U | V | W | X | Y | Z | a |
| | 1 | 1 | 1 | 1 | 1 | 1 | 3 | 1 | 1 | 2 | | 1 | 2 | | 4 | 1 | 2 | | | 3 | 1 | | 2 | 1 | | 1 | 1 |
| 6 | .5 | 1 | 1 | 1 | 1 | | 1 | 1 | | 1 | 1 | | 1 | | 4 | 1 | 2 | | | 5 | 1 | | 1 | 1 | | 1 | |
| | | 1 | | | | | | | | | | | | | 4 | | 3 | | | 3 | | | 1 | | | 2 | 2 |
| | 8 | | | 1 | | | | | | 1 | 1 | | | | 5 | 2 | 5 | | | 5 | | | | | | 1 | |
| | 4 | 2 | 1 | 1 | 1 | | 4 | 4 | | 2 | 1 | | 4 | | 5 | 1 | 4 | | | 5 | | 4 | 3 | 3 | | 2 | |
| | 2 | 1 | 1 | 1 | 1 | | 3 | 2 | | 2 | 1 | | 4 | | 5 | 1 | 4 | | | 5 | | 3 | 3 | 2 | | 4 | |
| | 1 | 1 | 1 | 1 | 1 | | 1 | 1 | | 1 | 1 | | 4 | | 5 | 1 | 4 | | | 5 | 1 | | 2 | 1 | | 3 | |
| 16 | 8 | | | | | | | | | 1 | | 1 | | | 4 | 1 | 3 | | | 2 | 1 | | 1 | | | 2 | 2 |
| 17 | 8 | | | | | | | | | 1 | | 4 | | | 4 | 1 | 3 | | | 4 | 1 | | 2 | | | 2 | 2 |
| | 4 | 1 | 1 | 1 | 1 | 1 | 1 | 1 | 1 | 1 | | 1 | 1 | | 4 | 1 | 2 | | | 4 | 1 | | 1 | 1 | | 1 | 1 |
| | 2 | 1 | 1 | 1 | 1 | 1 | 1 | 1 | 1 | 1 | | 1 | 1 | | 3 | 1 | 2 | | | 1 | 1 | | 1 | 1 | | 1 | 1 |
| | 1 | 1 | 1 | 1 | 1 | 1 | 1 | 1 | 1 | 1 | | 1 | 1 | | 1 | 1 | 1 | | | 1 | 1 | | 1 | 1 | | 1 | 1 |
| 18 | 8 | | | | | | | | | 1 | | 1 | | | 3 | 1 | 4 | | | 1 | 1 | | 1 | | | 1 | 1 |
| 20 | 5 | 1 | | 1 | 1 | | 3 | 3 | | 1 | 1 | | 5 | | 5 | 1 | 4 | | | 5 | 2 | | 1 | 1 | | 3 | |
| | 8 | | 4 | | | | | | | 3 | 1 | | | | 5 | 3 | 4 | | | 5 | | | | | | | |
| | 4 | 3 | 1 | 1 | 1 | | 4 | 4 | | 2 | 1 | | 5 | | 5 | 3 | 4 | | | 5 | 4 | | 4 | 2 | | 4 | |
| | 2 | 2 | 1 | 1 | 1 | | 4 | 4 | | 1 | 1 | | 5 | | 5 | 2 | 4 | | | 5 | 4 | | 3 | 1 | | 3 | |
| | 1 | 1 | 1 | 1 | 1 | | 3 | 3 | | 1 | 1 | | 5 | | 5 | 2 | 4 | | | 5 | 3 | | 3 | 1 | | 3 | |
| 23 | 8 | | | 2 | | | | | | 1 | 1 | | | | 3 | 2 | 4 | | | 2 | | | | | | 2 | |
| | 8 | | | 2 | | | | | | 1 | 1 | | | | 4 | 1 | 4 | | | 4 | | | | | | 1 | |
| | 4 | 1 | 1 | 1 | 1 | | 3 | 1 | | 1 | 1 | | 1 | | 1 | 1 | 1 | | | 1 | 1 | | 1 | 1 | | 1 | |
| | 2 | 1 | 1 | 1 | 1 | | 2 | 1 | | 1 | 1 | | 1 | | 1 | 1 | 1 | | | 1 | 1 | | 1 | 1 | | 1 | |
| | 1 | 1 | 1 | 1 | 1 | | 1 | 1 | | 1 | 1 | | 1 | | 1 | 1 | 1 | | | 1 | 1 | | 1 | 1 | | 1 | |
| 25 | .5 | 1 | 1 | 1 | 1 | 3 | 2 | | 1 | 2 | | 3 | 4 | | 5 | 1 | 3 | | | 5 | 1 | | 3 | 1 | | 3 | 2 |
| | .2 | 1 | 1 | 1 | 1 | 3 | 1 | 1 | 1 | 2 | | 2 | 3 | | 3 | 1 | 3 | | | 3 | 1 | | 3 | 1 | | 1 | 2 |
| | 8 | | | | | | | | | 4 | | 4 | | | 5 | 4 | 5 | | | 5 | 4 | | 4 | | | 4 | 4 |
| | 4 | 3 | 5 | 3 | 4 | 4 | 4 | 5 | 4 | 4 | | 4 | 5 | | 5 | 4 | 5 | | | 5 | 4 | | 4 | 4 | | 5 | 5 |
| | 2 | 2 | 5 | 2 | 3 | 4 | 3 | 5 | 4 | 3 | | 4 | 5 | | 5 | 3 | 5 | | | 5 | 3 | | 3 | 2 | | 3 | 4 |
| | 1 | 3 | 3 | 2 | 2 | 4 | 4 | 4 | 5 | 3 | | 4 | 5 | | 5 | 3 | 4 | | | 1 | 1 | | 2 | 5 | | 1 | 1 |
| | 1 | 1 | 1 | 1 | 2 | 4 | 3 | | 2 | 3 | | 4 | 4 | | 5 | 1 | 4 | | | 5 | 3 | | 4 | 1 | | 2 | 3 |
| 26 | 8 | | | 1 | | | | | | 4 | 1 | | | | 4 | 1 | 5 | | | 3 | | | | | | 1 | |
| | 4 | 1 | 1 | 1 | 1 | | 3 | 1 | | 1 | 1 | | 1 | | 3 | 1 | 2 | | | 1 | 1 | | 3 | 1 | | 1 | |
| | 2 | 1 | 1 | 1 | 1 | | 1 | 1 | | 1 | 1 | | 1 | | 1 | 1 | 1 | | | 1 | 1 | | 1 | 1 | | 1 | |
| 27 | 8 | | | | | | | | | 2 | | 5 | | | 5 | 1 | 3 | | | 4 | 2 | | 1 | | | 1 | 1 |
| | 4 | 1 | 1 | 1 | 1 | | 1 | 1 | | 1 | 1 | | 1 | | 1 | 1 | 1 | | | 1 | 1 | | 1 | 1 | | 1 | |
| 29 | 8 | | | | | | | | | 1 | | 3 | | | 4 | 1 | 3 | | 4 | | 1 | | 1 | | 1 | 2 | |
| | 4 | 1 | 1 | 1 | 1 | | 2 | 1 | | 1 | 1 | | 1 | | 3 | 1 | 2 | | | 2 | 1 | | 1 | 1 | | 1 | |
| | 2 | 1 | 1 | 1 | 1 | | 1 | 1 | | 1 | 1 | | 1 | | 1 | 1 | 1 | | | 1 | 1 | | 1 | 1 | | 1 | |
| 33 | 8 | | | | | | | | | 3 | | 4 | | | 5 | 1 | | | | 5 | 1 | | 3 | | | 2 | 1 |
| | 4 | 1 | 1 | 1 | 1 | | 2 | 3 | 1 | 2 | 2 | | 5 | 3 | | 5 | 1 | 3 | | | 5 | 1 | | 2 | 3 | | 2 | 2 |
| | 2 | 1 | 1 | 1 | 1 | | 3 | 3 | 1 | 3 | 3 | | 5 | 3 | | 5 | 1 | 3 | | | 4 | 1 | | 1 | 1 | | 1 | 1 |
| | 1 | 1 | 1 | 1 | 1 | | 2 | 1 | 1 | 2 | 2 | | 4 | 1 | | 4 | 1 | 2 | | | 4 | 1 | | 1 | 1 | | 1 | 1 |
| 38 | 8 | | | | | | | | | 1 | | 2 | | | 5 | 1 | 3 | | | 4 | 1 | | 3 | | | 3 | 3 |
| | 4 | 2 | 2 | 2 | 2 | 2 | 1 | 1 | 3 | 1 | | 1 | 1 | | 3 | 1 | 2 | | | 4 | 1 | | 2 | 1 | | 1 | 3 |
| | 2 | 2 | 1 | 1 | 1 | 1 | 1 | 1 | 1 | 1 | | 1 | | | 1 | | | | | 2 | 1 | | 2 | 1 | | 1 | 1 |
| | 1 | 1 | 1 | 1 | 1 | 2 | 1 | 1 | 1 | 1 | | 1 | 1 | | | 2 | 1 | | | 1 | 1 | | 1 | 1 | | 2 | 1 |
| 40 | 8 | | | | | | | | | 2 | | 1 | | | 4 | 1 | 4 | | | 3 | 1 | | 1 | | | 2 | 1 |
| | 2 | 1 | 1 | 1 | 1 | 3 | 1 | 1 | 1 | 1 | | 1 | 1 | | 1 | 1 | 1 | | | 1 | 1 | | 1 | 1 | | 1 | 1 |
| | 1 | 1 | 1 | 1 | 1 | 1 | 1 | 1 | 1 | 1 | | 1 | 1 | | 1 | 1 | 1 | | | 1 | 1 | | 1 | 1 | | 1 | 1 |
| 43 | 8 | | | | | | | | | 4 | | 4 | | | 5 | 2 | 5 | | | 5 | 4 | | 4 | | | 4 | 4 |
| | 4 | 1 | 1 | 1 | 1 | 4 | 3 | 4 | 3 | 2 | | 4 | 3 | | 4 | 1 | 4 | | | 5 | 3 | | 2 | 1 | | 3 | 4 |
| | 2 | 1 | 1 | 1 | 1 | 1 | 2 | 3 | 1 | 1 | | 3 | 3 | | 4 | 1 | 3 | | | 4 | 1 | | 1 | 1 | | 2 | 3 |
| | 1 | 1 | 1 | 1 | 1 | 1 | 1 | 1 | 1 | 1 | | 3 | 1 | | 3 | 1 | 3 | | | 2 | 1 | | 1 | 1 | | 1 | 1 |
| 44 | .5 | 1 | 1 | 1 | 1 | | 1 | 1 | | 1 | 1 | | 4 | | 5 | 1 | 3 | | | 4 | 1 | | 2 | 1 | | 1 | |
| | 8 | | | | | | | | | 4 | | 4 | | | 5 | 3 | 5 | | | 5 | 5 | | 4 | | | 4 | 3 |
| | 4 | 1 | 1 | 1 | 1 | | 4 | 3 | | 1 | 1 | | 5 | | 5 | 2 | 4 | | | 5 | 4 | | 3 | 1 | | 1 | |
| | 2 | 1 | 1 | 1 | 1 | | 4 | 2 | | 1 | 1 | | 5 | | 5 | 1 | 4 | | | 5 | 3 | | 3 | 1 | | 1 | |
| | 1 | 1 | 1 | 1 | 1 | | 3 | 1 | | 1 | 1 | | 4 | | 5 | 1 | 3 | | | 5 | 1 | | 0 | 1 | | 1 | |
| 45 | 8 | | | | | | | | | 3 | | 3 | | | 5 | 1 | 4 | | | 5 | 2 | | 1 | | | 1 | 2 |
| | 4 | 1 | 1 | 1 | 1 | | 3 | 1 | | 1 | 1 | | 1 | | 1 | 3 | 1 | | | 3 | 1 | | 1 | 1 | | 1 | |
| | 2 | 1 | 1 | 1 | 1 | | 2 | 1 | | 1 | 1 | | 1 | | 1 | 3 | 1 | | | 2 | 1 | | 1 | 1 | | 1 | |
| | 1 | 1 | 1 | 1 | 1 | | 1 | 1 | | 1 | 1 | | 1 | | 1 | 1 | 1 | | | 1 | 1 | | 1 | 1 | | 1 | |
| 47 | .5 | 1 | 1 | 1 | 1 | | 1 | 1 | | 1 | 1 | | 2 | | 4 | 1 | 2 | | | 3 | 1 | | 1 | 1 | | 1 | |
| | 8 | | | | | | | | | 3 | | 4 | | | 5 | 1 | 3 | | | 4 | 2 | | 3 | | | 2 | 3 |
| | 4 | 1 | 2 | 1 | 1 | | 3 | 1 | | 1 | 1 | | 4 | | 5 | 1 | 4 | | | 5 | 1 | | 1 | 1 | | 1 | |
| | 2 | 1 | 1 | 1 | 1 | | 3 | 1 | | 1 | 1 | | 4 | | 5 | 1 | 3 | | | 4 | 1 | | 1 | 1 | | 1 | |
| | 1 | 1 | 1 | 1 | 1 | | 2 | 1 | | 1 | 1 | | 2 | | 4 | 1 | 3 | | | 4 | 1 | | 1 | 1 | | 1 | |
| 49 | 8 | | | | | | | | | 3 | 1 | | | | 2 | 4 | 3 | | | 3 | | | 3 | | | 2 | 2 |
| 51 | 8 | | | | | | | | | 1 | 3 | | | | 4 | 1 | | | | 4 | | | 2 | | | 1 | 1 |
| | 4 | 1 | 1 | 1 | 1 | 1 | 1 | 1 | 1 | 1 | | 2 | 1 | | 3 | 1 | 2 | | | 2 | 1 | | 1 | 1 | | 1 | 1 |
| | 2 | 1 | 1 | 1 | 1 | 1 | 1 | 2 | 1 | 1 | | 3 | 1 | | 3 | 1 | 2 | | | 2 | 1 | | 1 | 1 | | 1 | 1 |
| | 1 | 1 | 1 | 1 | 1 | 1 | 1 | 1 | 1 | 1 | | 2 | 1 | | 2 | 1 | 1 | | | 2 | 1 | | 1 | 1 | | 1 | 1 |
| 52 | 8 | | | | | | | | | 3 | | 1 | | | 2 | 1 | 1 | | | 1 | 1 | | 1 | | | 1 | 1 |
| 53 | 8 | | | | | | | | | 1 | | 1 | | | 4 | 1 | 4 | | | 3 | 1 | | 1 | | | 1 | 1 |
| | 4 | 1 | 1 | 1 | 1 | 1 | 1 | 1 | 1 | 1 | | 1 | 1 | | 1 | 1 | 2 | | | 1 | 1 | | 1 | 1 | | 1 | 1 |
| | 2 | 1 | 1 | 1 | 1 | 1 | 1 | 1 | 1 | 1 | | 1 | 1 | | 2 | 1 | 2 | | | 1 | 1 | | 1 | 1 | | 1 | 1 |
| | 1 | 1 | 1 | 1 | 1 | 1 | 1 | 1 | 1 | 1 | | 1 | 1 | | 1 | 1 | 1 | | | 1 | 1 | | 1 | 1 | | 1 | 1 |
| 54 | 8 | | | | | | | | | 1 | | 1 | | | 4 | 2 | 4 | | | 3 | 2 | | 1 | | | 1 | 1 |
| | 4 | 1 | 1 | 1 | 1 | 1 | 1 | 1 | 1 | 1 | | 1 | 1 | | 3 | 1 | 1 | | | 2 | 1 | | 1 | 1 | | 1 | 1 |
| | 2 | 1 | 1 | 1 | 1 | 1 | 1 | 1 | 1 | 1 | | 1 | 1 | | 1 | 1 | 1 | | | 1 | 1 | | 1 | 1 | | 1 | 1 |

TABLE A-continued

| EX. NO. | Rate lbs/A | Pre-emergence |||||||||||||||||||||||||||
|---|---|---|---|---|---|---|---|---|---|---|---|---|---|---|---|---|---|---|---|---|---|---|---|---|---|---|---|
| | | A | B | C | D | E | F | G | H | I | J | K | L | M | N | O | P | Q | R | S | T | U | V | W | X | Y | Z | a |
| 57 | 8 | | | | | | | | | 2 | | 1 | | | 3 | 2 | 3 | | 1 | | 1 | 2 | | | | 1 | 1 |
| 58 | 8 | | | | | | | | | 1 | | 2 | | | 4 | 1 | 3 | | 4 | | 1 | 3 | | | | 3 | 2 |
| | 4 | 1 | 1 | 1 | 1 | 1 | 3 | 1 | 2 | 1 | | 1 | 2 | | 3 | 1 | 3 | | 3 | | 1 | 2 | 1 | | | 1 | 1 |
| | 2 | 1 | 1 | 1 | 1 | 1 | 2 | 1 | 1 | 1 | | 1 | 2 | | 3 | 1 | 2 | | 1 | | 1 | 1 | 1 | | | 1 | 1 |
| | 1 | 1 | 1 | 1 | 1 | 1 | 1 | 1 | 1 | 1 | | 1 | 1 | | 1 | 1 | 1 | | 1 | | 1 | 1 | 1 | | | 1 | 1 |
| 59 | 8 | | | | | | | | | 1 | | 1 | | | 3 | 1 | 3 | | 4 | | 1 | 1 | | | | 1 | 1 |
| 60 | 8 | | | | | | | | | 2 | | 3 | | | 4 | 1 | 3 | | 4 | | 2 | 2 | | | | 2 | 1 |
| | 4 | 1 | 1 | 1 | 1 | 1 | 2 | 3 | 1 | 2 | | 2 | 3 | | 4 | 2 | 3 | | 4 | | 1 | 2 | 1 | | | 2 | 2 |
| | 2 | 1 | 1 | 1 | 1 | 1 | 1 | 2 | 1 | 1 | | 2 | 1 | | 4 | 1 | 2 | | 3 | | 1 | 2 | 1 | | | 1 | 1 |
| | 1 | 1 | 1 | 1 | 1 | 1 | 1 | 1 | 1 | 1 | | 1 | 1 | | 2 | 1 | 2 | | 2 | | 1 | 2 | 1 | | | 1 | 1 |
| 61 | 8 | | | | 1 | | | | | 2 | 1 | | | | 4 | 2 | 3 | | 4 | | | | | | | 2 | |
| 63 | 8 | | | | 1 | | | | | 2 | 1 | | | | 2 | 1 | 1 | | 3 | | | | | | | 2 | |
| 64 | 8 | | | | 1 | | | | | 2 | 2 | | | | 4 | 2 | 3 | | 4 | | | | | | | 2 | |
| 65 | .5 | 1 | 1 | 1 | 1 | | 1 | 1 | | 1 | 1 | | 1 | | 1 | 1 | 1 | | 1 | | 1 | 1 | 1 | | | 1 | |
| | 8 | | | | 1 | | | | | 3 | 1 | | | | 5 | 2 | 4 | | 5 | | | | | | | 3 | |
| | 4 | 1 | 1 | 1 | 1 | | 3 | 1 | | 3 | 1 | | 1 | | 5 | 1 | 0 | | 4 | | 2 | 1 | 1 | | | 3 | |
| | 2 | 1 | 1 | 1 | 1 | | 3 | 1 | | 2 | 1 | | 1 | | 4 | 1 | 2 | | 2 | | 1 | 1 | 1 | | | 2 | |
| | 1 | 1 | 1 | 1 | 1 | | 2 | 1 | | 2 | 1 | | 1 | | 4 | 1 | 2 | | 2 | | 1 | 1 | 1 | | | 1 | |

TABLE B

| EX. NO. | Rate lbs/A | Pre-emergence |||||||||||||||||||||||||||
|---|---|---|---|---|---|---|---|---|---|---|---|---|---|---|---|---|---|---|---|---|---|---|---|---|---|---|---|
| | | A | B | C | D | E | F | G | H | I | J | K | L | M | N | O | P | Q | R | S | T | U | V | W | X | Y | Z | a |
| 3 | 8 | | | | | | | | | 2 | | 1 | | 2 | 2 | 2 | | | 2 | | 2 | 3 | | | | 3 | 3 |
| 6 | .5 | 1 | 3 | 3 | 1 | | 3 | 1 | | | 1 | | | | | | | | | | | | | | | | |
| | 8 | | | 3 | | | | | | 3 | 2 | | | | 1 | 3 | 4 | | 3 | | | | | | | 3 | |
| | 4 | 2 | 3 | 4 | 1 | | 4 | 1 | | | 1 | | | | | | | | | | | | | | | | |
| | 2 | 1 | 3 | 3 | 1 | | 4 | 1 | | | 1 | | | | | | | | | | | | | | | | |
| | 1 | 1 | 3 | 3 | 1 | | 3 | 1 | | | 1 | | | | | | | | | | | | | | | | |
| 16 | 8 | | | | | | | | | 2 | | 1 | | | 2 | 2 | 4 | | 2 | | 1 | 3 | | | 3 | 2 | |
| 18 | 8 | | | | | | | | | 2 | | 2 | | | 3 | 4 | 3 | | 2 | | 2 | 2 | | | 2 | 3 | |
| 20 | .5 | 1 | 2 | 2 | 1 | | 2 | 1 | | | 1 | | | | | | | | | | | | | | | | |
| | 8 | | | 3 | | | | | | 3 | 2 | | | | 3 | 3 | 4 | | 3 | | | | | | | 3 | |
| | 4 | 3 | 3 | 3 | 1 | | 3 | 1 | | | 1 | | | | | | | | | | | | | | | | |
| | 2 | 1 | 3 | 3 | 1 | | 3 | 1 | | | 1 | | | | | | | | | | | | | | | | |
| | 1 | 1 | 2 | 2 | 1 | | 2 | 1 | | | 1 | | | | | | | | | | | | | | | | |
| 23 | 8 | | | 2 | | | | | | 1 | 1 | | | | 1 | 1 | 3 | | 1 | | | | | | | 3 | |
| 25 | 8 | | | | | | | | | 4 | 4 | | | | 4 | 4 | 4 | | 4 | | 2 | 4 | | | | 4 | 4 |
| | 4 | | | | | | | | | 4 | 4 | | | | 2 | 2 | 3 | | 4 | | 1 | 3 | | | | 3 | 3 |
| | 2 | | | | | | | | | 3 | 2 | | | | 3 | 2 | 3 | | 4 | | 1 | 3 | | | | 3 | 2 |
| | 1 | | | | | | | | | 3 | 2 | | | | 1 | 1 | 2 | | 3 | | 1 | 2 | | | | 3 | 1 |
| 29 | 8 | | | | | | | | | 2 | 1 | | | | 1 | 1 | 3 | | 1 | | 1 | 2 | | | | 3 | 2 |
| 38 | 8 | | | | | | | | | 1 | 1 | | | | 1 | 1 | 2 | | 1 | | 1 | 1 | | | | 2 | 2 |
| 40 | 8 | | | | | | | | | 1 | 1 | | | | 1 | 2 | 3 | | 1 | | 1 | 1 | | | | 2 | 2 |
| 43 | 8 | | | | | | | | | 3 | 4 | | | | 3 | 3 | 4 | | 3 | | 2 | 3 | | | | 3 | 3 |
| | 4 | | | | | | | | | 1 | 1 | | | | 1 | 1 | 3 | | 2 | | 1 | 1 | | | | 3 | 2 |
| | 2 | | | | | | | | | 1 | 1 | | | | 1 | 1 | 1 | | 1 | | 1 | 1 | | | | 2 | 1 |
| | 1 | | | | | | | | | 1 | 1 | | | | 1 | 1 | 1 | | 1 | | 1 | 1 | | | | 2 | 1 |
| 44 | .5 | 1 | 3 | 3 | 1 | | 2 | 1 | | 2 | 1 | | 2 | | 1 | 1 | 1 | | 3 | | 1 | 2 | 1 | | | 3 | |
| | 8 | | | | | | | | | 4 | | 4 | | | 4 | 4 | 4 | | 4 | | 2 | 3 | | | | 3 | 4 |
| | 4 | 1 | 3 | 2 | 1 | | 3 | 1 | | 4 | 1 | | 3 | | 1 | 1 | 3 | | 3 | | 1 | 3 | 3 | | | 4 | |
| | 2 | 1 | 3 | 3 | 1 | | 3 | 1 | | 3 | 1 | | 2 | | 1 | 1 | 2 | | 3 | | 1 | 3 | 2 | | | 3 | |
| | 1 | 1 | 3 | 2 | 1 | | 2 | 1 | | 2 | 1 | | 2 | | 1 | 1 | 1 | | 2 | | 1 | 2 | 2 | | | 3 | |
| 47 | .5 | 1 | 1 | 1 | 1 | | 2 | 1 | | 1 | 1 | | 1 | | 1 | 1 | 1 | | 2 | | 1 | 1 | 1 | | | 1 | |
| | 8 | | | | | | | | | 4 | | 4 | | | 4 | 3 | 3 | | 4 | | 2 | 3 | | | | 3 | 3 |
| | 4 | 1 | 2 | 3 | 1 | | 3 | 1 | | 4 | 1 | | 3 | | 1 | 2 | 3 | | 3 | | 1 | 4 | 3 | | | 4 | |
| | 2 | 1 | 2 | 3 | 1 | | 2 | 1 | | 2 | 1 | | 2 | | 1 | 2 | 1 | | 3 | | 1 | 4 | 1 | | | 2 | |
| | 1 | 1 | 1 | 2 | 1 | | 2 | 1 | | 2 | 1 | | 2 | | 1 | 2 | 1 | | 3 | | 1 | 3 | 1 | | | 2 | |
| 49 | 8 | | | | | | | | | 1 | | 1 | | | 1 | 2 | 2 | | 1 | | 1 | 1 | | | | 2 | 2 |
| 51 | 8 | | | | | | | | | 1 | | 1 | | | 1 | 1 | 1 | | 1 | | 1 | 1 | | | | 1 | 1 |
| 52 | 8 | | | | | | | | | 1 | | 1 | | | 1 | 1 | 1 | | 1 | | 1 | 1 | | | | 1 | 1 |
| 53 | 8 | | | | | | | | | 1 | | 1 | | | 1 | 3 | 3 | | 1 | | 1 | 1 | | | | 2 | 2 |
| 54 | 8 | | | | | | | | | 1 | | 1 | | | 1 | 1 | 1 | | 1 | | 1 | 1 | | | | 1 | 1 |
| 57 | 8 | | | | | | | | | 1 | | 1 | | | 1 | 2 | 4 | | 1 | | 1 | 1 | | | | 2 | 2 |
| 58 | 8 | | | | | | | | | 1 | | 1 | | | 1 | 1 | 1 | | 2 | | 1 | 1 | | | | 1 | 1 |
| 59 | 8 | | | | | | | | | 1 | | 1 | | | 1 | 1 | 1 | | 1 | | 1 | 1 | | | | 2 | 2 |
| 60 | 8 | | | | | | | | | 2 | | 2 | | | 3 | 2 | 3 | | 2 | | 1 | 2 | | | | 2 | 3 |
| 61 | 8 | | | 2 | | | | | | 3 | 1 | | | | 1 | 3 | 3 | | 1 | | | | | | | 4 | |
| 63 | 8 | | | 2 | | | | | | 1 | 1 | | | | 1 | 2 | 3 | | 1 | | | | | | | 2 | |
| 64 | 8 | | | 2 | | | | | | 2 | 2 | | | | 2 | 2 | 3 | | 2 | | | | | | | 3 | |
| 65 | .5 | 1 | 2 | 2 | 1 | | 3 | 1 | | 1 | 1 | | 3 | | 1 | 1 | 1 | | 1 | | 1 | 1 | 1 | | | 2 | |
| | 8 | | | 2 | | | | | | 3 | 1 | | | | 2 | 2 | 4 | | 4 | | | | | | | 4 | |
| | 4 | 1 | 2 | 2 | 1 | | 3 | 1 | | 3 | 1 | | 3 | | 2 | 2 | 3 | | 1 | | 1 | 3 | 2 | | | 3 | |
| | 2 | 1 | 2 | 2 | 1 | | 3 | 1 | | 2 | 1 | | 2 | | 1 | 2 | 2 | | 1 | | 1 | 2 | 1 | | | 2 | |
| | 1 | 1 | 2 | 2 | 1 | | 3 | 1 | | 2 | 1 | | 3 | | 1 | 2 | 1 | | 1 | | 1 | 2 | 2 | | | 2 | |

The tests discussed above show that the compounds of this invention are useful for the protection of plants Practice of the method does not necessarily kill the phytopathogens. As the data above show, application of a phytopathogen-inhibiting amount of a compound reduces the adverse effects of the disease, even though only a part of the phytopathogen population may be killed by the compound. The term "phytopathogen-inhibiting amount" is used here to describe an amount which is sufficient to reduce the adverse effects of a phytopathogen. The term "reducing the adverse effects" refers to weakening the pathogen sufficiently that its reproduction rate and its vigor are decreased, with the result that the express signs of the disease, and the concomitant injury to the host plant, are decreased as compared with untreated plants.

As is usual in the plant protection art, best results are obtained by applying the compound several times during the growing season at intervals of from a few days to a few weeks, depending on the weather and the severity of the disease. The compounds may effectively be applied either before or after the outbreak of an infestation of a phytopathogen.

It is preferred to use the compounds against fungal phytopathogens. Some particularly preferred crops on which the compounds are effectively used are grapes, cucumbers, wheat, barley, peanuts and sugar beets. Particularly important phytopathogens, against which the compounds are particularly preferably used, include leaf rust, Septoria leaf spot, and Helminthosporium leaf spot of wheat, powdery mildew of wheat, cucurbits, sugar beet or grape, apple scab and Cercospora leaf spot of sugar beet and peanut.

It is usual to measure a foliar application of a plant protectant by the concentration of the dispersion in which it is applied. It is measured in this way because it is customary to apply a sufficient amount of the dispersion to cover the foliage with a thin film, and the amount of dispersion applied is thus dependent on the foliar area of the plant being treated. In general, compound concentrations in the range of from about 5 parts per million to about 500 parts per million are used in the practice of this invention, preferably concentrations from about 10 parts per million to about 100 parts per million. The concentration to be used in a given instance, of course, varies with the intensity of the infection to be combatted, as well as with the identity of the compound and the weather, and the characteristics of the foliage to which the compound is applied.

However, in other instances, it is preferable to measure the amount of the compound by the amount applied per unit area of land. When the compound is applied to the soil, it is obviously preferable to measure it in that way. It is also preferred, in dealing with a low-spreading crop, such as cucumber, to measure the application by the unit of area to be covered. In such cases, amounts of compound from about 0.1 pound per acre to about 10 pounds per acre are effectively used, depending on the pathogen, the crop and the environmental factors.

Since many of the compounds are selectively herbicidal, as shown by the tests above, they are also useful in a method of reducing the vigor of weeds which comprises the application of an herbicidally-effective amount of a compound of the invention to the weed or the soil in which it grows. It will be observed in the test results above that many of the compounds are safe to crops and that the compounds can therefore be used in cropland to protect the crop from the competition of weeds. In the context of this invention, weed seeds are included in the term "weeds".

It will be observed that the compounds are effective in reducing the vigor of weeds when applied both preemergence and postemergence. Thus, they can be applied to the soil to affect weeds by soil contact when the weeds are germinating and emerging, and can also be used against emerged weeds by direct contact with the exposed portions of the weed. It is preferred but not necessary to incorporate the compounds in the soil when they are applied preemergence.

The term "reduce the vigor of" is used here to refer to both killing and injuring the weeds which are contacted with a compound. In some instances, as is clear from the test results, the whole population the weed is killed. In other instances, part of the weeds are killed and part of them are injured, and in still other instances, none of the weeds are killed but are merely injured by application of the compound. It will be understood that reducing the vigor of the weed population by injuring part of them is beneficial, even though part of the population survives application of the compound. The weeds, the vigor of which has been reduced, are unusually susceptible to the normal stresses which afflict plants, such as disease, drought, lack of nutrients and so forth.

In general, application rates range from about 1.0 lb./acre to about 20 lb./acre. The optimum rates will usually be found to be within the preferred range of from about 2.0 lb./acre to about 10 lb./acre. It will be understood that many factors affect the choice of application rate against a given weed, including the method of compound application, weather, soil type, organic matter content of the soil and the hardness and suspended organic matter content of the water.

The time when the compounds should be applied to the soil or weeds is widely variable, since the compounds are effective both preemergence and postemergence. At least some control of weeds will result from application of the compounds at any time when weeds are growing or germinating. They may also be applied to the soil during a dormant season to control weeds germinating during the following warm season.

The compounds of this invention are applied, whether for fungicidal or herbicidal purposes, in the form of compositions which are important embodiments of the invention, and which comprise a compound of this invention and an agriculturally-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids usually known as wettable powders, or liquids usually known as emulsifiable concentrates or aqueous suspensions. Wettable powders, which may be compacted to form wettable granules, comprise an intimate mixture of the active compound, an inert carrier and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenol.

Emulsifiable concentrates of the compounds comprise a convenient concentration of compound, such as from about 10% to about 50% by weight of liquid, dissolved in an inert carrier which is a mixture of water-immiscible organic solvent and emulsifiers. Useful organic solvents include the aromatics, especially the xylenes, and the petroleum fractions, especially the high-boiling napthalenic and olefinic portions of petroleum such as heavy aromatic naphtha. Other organic solvents may also be used, such as the terpenic solvents including rosin derivatives, and complex alcohols such as 2-ethoxyethanol. Suitable emulsifiers for emulsifiable concentrates are chosen from the same types of surfactants discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts, may also be added, to increase the density of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent, and applying it to a granular carrier which has been preformed to the appropriate particle size, in the range of from about 0.5 to about 3 ml. Such compositions may also be formulated by making a dough or paste of the carrier and compound, and crushing and drying to obtain the desired granular particle size.

Dusts containing the compounds are prepared simply by intimately mixing the compound in powdered form with a suitable dusty agricultural carrier, such as kaolin clay, ground volcanic rock and the like. Dusts can suitably contain from about 1% to about 10% of the compound.

The following exemplary formulations are described, to illustrate further the manner in which compositions of the invention are made. It will be understood that any desired compound of the invention may be formulated in any manner.

| Emulsifiable Concentrate | |
|---|---|
| Compound of Example 3 | 24.5 |
| Sponto 1003 (surfactant blend) | 10.0% |
| Ethylene glycol, methyl ether | 20% |
| Xylene | 45.5% |
| Emulsifiable Concentrate | |
| Compound of Example 3 | 33.3% |
| Sponto 1003 (surfactant blend) | 10.0% |
| Xylene | 56.7% |
| Aqueous Suspension | |
| Compound of Example 13 | 9.4% |
| Tergitol TMN-6 (non-ionic surfactant) | 10.0% |
| Purified Silicate | 1.0% |
| 2% Xanthan Solution | 10.0% |
| Antifoam | 0.2% |
| Lignin Sulfonate | 0.3% |
| Water | 69.1% |

The product was ground for 2.5 hours in an attrition mill, until 50% of the particles of the compound were less than 3 microns in diameter.

| Emulsifiable Concentrate | |
|---|---|
| Compound of Example 13 | 12.5% |
| Non-ionic surfactant | 16.0% |
| Sponto 714T (surfactant blend) | 4.0% |
| Dimethylformamide | 50.0% |
| Aromatic Naphtha | 17.5% |
| Aqueous Suspension | |
| Compound of Example 13 | 12.5% |
| Tertigol TMN-6 (non-ionic surfactant) | 10.0% |
| Purified silicate | 1.0% |
| 2% Xanthan solution | 10.0% |
| Antifoam | 0.2% |
| Water | 66.3% |

The product was ground in an attrition mill for 4 hours, until 50% of the particles of compound were less than 2.8 microns in diameter.

| Emulsifiable Concentrate | |
|---|---|
| Compound of Example 44 | 12.5% |
| Toximul D (surfactant blend) | 2.0% |
| Sponto AD6-29 (non-ionic surfactant) | 2.0% |
| Aromatic Naphtha | 83.5% |
| Emulsifiable Concentrate | |
| Compound of Example 6 | 37.5% |
| Toximul D (surfactant blend) | 2.5% |
| Toximul H (non-ionic surfactant) | 2.5% |
| Aromatic Naphtha | 57.5% |
| Emulsifiable Concentrate | |
| Compound of Example 44 | 12.5% |
| Propylene glycol, methyl ether | 57.6% |
| Toximul D (surfactant blend) | 2.0% |
| Sponto AD-29 (non-ionic surfactant) | 2.0% |
| Aromatic Naphtha | 25.9% |
| Emulsifiable Concentrate | |
| Compound of Example 6 | 37.5% |
| Propylene glycol, methyl ether | 39.7% |
| Toximul D (surfactant blend) | 2.5% |
| Sponto AD6-29 | 2.5% |
| Aromatic Naphtha | 17.8% |
| Emulsifiable Concentrate | |
| Compound of Example 6 | 25.0% |
| Toximul D (surfactant blend) | 3.0% |
| Sponto AD6-29 (non-ionic) | 3.0% |
| Aromatic Naphtha | 69.0% |

Test XXXI

Representative compounds were tested against fungi which infect humans, *Aspergillus flavus*, *Candida albicans*, and *Trichophyton mentagrophytes*. The fungi were grown on agar plates, and the compounds were contacted with the fungi in the form of 7-mm. paper discs impregnated with known amounts of the compounds. Activity was indicated by a zone of inhibited growth of the fungus around the paper disc. Results are reported below as the smallest amount of compound which produced activity. The highest amount tested was 20 mcg./disc; lack of activity at that rate is shown by "N".

TABLE XXI

| Compound of Example No. | A. flavus | C. albicans | T. ment. |
|---|---|---|---|
| 3 | 10 mcg. | 10 mcg. | 5 mcg. |
| 4 | 20 | 20 | 5 |
| 5 | N | 0.62 | N |
| 6 | 2.5 | 0.16 | 5 |
| 9 | N | N | 20 |
| 10 | N | N | 10 |
| 12 | 2.5 | 0.08 | 2.5 |
| 13 | 5 | 5 | 5 |
| 14 | N | 1.2 | N |
| 17 | N | 0.31 | 20 |
| 20 | 20 | 0.04 | 0.62 |
| 23 | N | 5 | N |
| 25 | 1.2 | 2.5 | 2.5 |
| 29 | N | 1.2 | N |
| 33 | N | 0.08 | 2.5 |
| 40 | N | 10 | 5 |
| 41 | N | N | N |
| 44 | N | 0.31 | 20 |
| 50 | 10 | 1.2 | 10 |
| 51 | N | 10 | N |
| 53 | N | N | 5 |
| 59 | N | N | 20 |
| 61 | N | 0.08 | 1.2 |
| 65 | N | 0.16 | 2.5 |

Four of the compounds were tested against a *C. albicans* infection in mice by injecting the compounds intraperitoneally at 25, 50 and 100 mg./kg. Control of the infection was achieved only by the 50 mg./kg. rate of Example 6 and the 100 mg./kg. rate of Example 25.

Thus, the compounds are also useful for control of fungal pathogens of animals, including humans. The compounds may particularly be used topically for control of infections of the skin or mucous membranes, such as athlete's foot, vaginal infections and the like. They are also used for sterilizing surfaces and substances contaminated with fungal pathogens, particularly when formulated with detergents, soaps or other antimicrobials effective against pathogens other than fungi.

We claim:

1. A compound of the formula

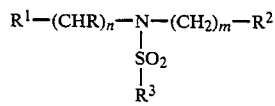

wherein
n is 1;
m is 0, 1 or 2;
R is hydrogen; $C_1$–$C_4$ alkyl; phenyl; or phenyl monosubstituted with fluoro, chloro, bromo or iodo;
$R^1$ is pyridinyl; pyridinyl oxide; or 5-pyrimidinyl;
$R^2$ is $C_3$–$C_8$ cycloalkyl; $C_4$–$C_{10}$ alkyl; cyano; phenyl mono- or disubstituted with fluoro, chloro, bromo, iodo, $C_1$–$C_3$ alkyl, $C_1$–$C_3$ (fluoro, chloro or bromo)alkyl, $C_1$–$C_3$ alkoxy, $C_1$–$C_3$ (fluoro, chloro or bromo)alkoxy, $C_1$–$C_3$ alkylthio, hydroxy, nitro, or cyano; or phenyl monosubstituted with $C_3$–$C_8$ cycloalkylmethoxy or phenoxy;
$R^3$ is $C_1$–$C_6$ alkyl; $C_1$–$C_3$ alkylamino; di($C_1$–$C_3$ alkyl)amino; $C_1$–$C_3$ (fluoro, chloro or bromo)alkyl; phenyl; or phenyl mono- or disubstituted with fluoro, chloro, bromo, iodo, $C_1$–$C_3$ alkyl, or $C_1$–$C_3$ (fluoro, chloro or bromo)alkyl;
provided that $R_2$ is cyano only when m is 1 or 2; or an acid addition salt of compounds wherein $R^1$ is pyridinyl or 5-pyrimidinyl; provided that salts of compounds wherein $R^1$ is 5-pyrimidinyl are only hydrohalides.

2. A compound of claim 1 wherein R is hydrogen or methyl.

3. A compound of claim 2 wherein $R^1$ is pyridinyl or pyridinyl oxide.

4. A compound of claim 3 wherein $R^2$ is substituted phenyl.

5. A compound of claim 4 wherein $R^2$ is phenyl substituted with fluoro, chloro, bromo, iodo, $C_1$–$C_3$ alkyl, $C_1$–$C_3$ (fluoro, chloro, or bromo)alkyl or $C_1$–$C_3$ (fluoro, chloro, or bromo)alkoxy.

6. A compound of claim 5 wherein $R^1$ is 3-pyridinyl or 3-pyridinyl oxide.

7. A compound of claim 4 wherein $R^3$ is $C_1$–$C_4$ alkyl, methylamino, dimethylamino or substituted phenyl.

8. A method of claim 6 wherein $R^3$ is $C_1$–$C_4$ alkyl, methylamino, dimethylamino or substituted phenyl.

9. A compound of claim 5 wherein $R^3$ is methyl, methylamino, dimethylamino, or phenyl substituted with fluoro, chloro, bromo, iodo, methyl, or (fluoro, chloro or bromo)methyl.

10. A compound of claim 8 wherein $R^3$ is methyl, methylamino, dimethylamino, or phenyl substituted with fluoro, chloro, bromo, iodo, methyl, or (fluoro, chloro or bromo)methyl.

11. The compound of claim 1 which is N-(2,4-dichlorophenyl)-N-(pyridin-3-ylmethyl)-methanesulfonamide.

12. The compound of claim 1 which is N-(2,4-difluorophenyl)-N-(pyridin-3-ylmethyl)-methanesulfonamide.

13. The compound of claim 1 which is N-(4-chloro-2-methylphenyl)-N-(pyridin-3-ylmethyl)-methanesulfonamide.

14. The compound of claim 1 which is N-(4-fluorophenyl)-N-(pyridin-3-ylmethyl)-methanesulfonamide.

15. The compound of claim 1 which is N-(2,4-dimethylphenyl)-N-(pyridin-3-ylmethyl)-methanesulfonamide.

16. A method of reducing the adverse effects of phytopathogens on plants which comprises applying a phytopathogen-inhibiting amount of a compound of claim 1 to the plant or to the soil in which the plant grows.

17. A method of reducing the adverse effects of phytopathogens on plants which comprises applying a phytopathogen-inhibiting amount of a compound of claim 2 to the plant or to the soil in which the plant grows.

18. A method of reducing the adverse effects of phytopathogens on plants which comprises applying a phytopathogen-inhibiting amount of a compound of claim 4 to the plant or to the soil in which the plant grows.

19. A method of reducing the adverse effects of phytopathogens on plants which comprises applying a phytopathogen-inhibiting amount of a compound of claim 6 to the plant or to the soil in which the plant grows.

20. A method of reducing the adverse effects of phytopathogens on plants which comprises applying a phytopathogen-inhibiting amount of a compound of claim 9 to the plant or to the soil in which the plant grows.

21. A method of claim 16 wherein the compound is N-(2,4-dichlorophenyl)-N-(pyridin-3-ylmethyl)-methanesulfonamide.

22. A method of claim 16 wherein the compound is N-(2,4-difluorophenyl)-N-(pyridin-3-ylmethyl)-methanesulfonamide.

23. A method of claim 16 wherein the compound is N-(4-chloro-2-methylphenyl)-N-(pyridin-3-ylmethyl)-methanesulfonamide.

24. A method of claim 16 wherein the compound is N-(4-fluorophenyl)-N-(pyridin-3-ylmethyl)-methanesulfonamide.

25. A method of claim 16 wherein the compound is N-(2,4-dimethylphenyl)-N-(pyridin-3-ylmethyl)-methanesulfonamide.

26. An agricultural composition comprising an agriculturally-acceptable inert carrier and a compound of claim 1.

27. An agricultural composition comprising an agriculturally-acceptable inert carrier and a compound of claim 2.

28. An agricultural composition comprising an agriculturally-acceptable inert carrier and a compound of claim 4.

29. An agricultural composition comprising an agriculturally-acceptable inert carrier and a compound of claim 6.

30. An agricultural composition comprising an agriculturally-acceptable inert carrier and a compound of claim 10.

31. A composition of claim 26 wherein the compound is N-(2,4-dichlorophenyl)-N-(pyridin-3-ylmethyl)-methanesulfonamide.

32. A composition of claim 26 wherein the compound is N-(2,4-difluorophenyl)-N-(pyridin-3-ylmethyl)-methanesulfonamide.

33. A composition of claim 26 wherein the compound is N-(4-chloro-2-methylphenyl)-N-(pyridin-3-ylmethyl)-methanesulfonamide.

34. A composition of claim 26 wherein the compound is N-(4-fluorophenyl)-N-(pyridin-3-ylmethyl)methanesulfonamide.

35. A composition of claim 26 wherein the compound is N-(2,4-dimethylphenyl)-N-(pyridin-3-ylmethyl)-methanesulfonamide.

* * * * *